US005596071A

United States Patent [19]

Payne et al.

[11] Patent Number: 5,596,071
[45] Date of Patent: Jan. 21, 1997

[54] *BACILLUS THURINGIENSIS* TOXINS ACTIVE AGAINST HYMENOPTERAN PESTS

[75] Inventors: Jewel M. Payne, Davis, Calif.; M. Keith Kennedy, Racine, Wis.; John B. Randall, Racine, Wis.; Henry Meier, Racine, Wis.; Heidi J. Uick, Racine, Wis.; Luis Foncerrada; H. Ernest Schnepf, both of San Diego, Calif.; George E. Schwab, Encinitas, Calif.; Jenny Fu, San Diego, Calif.

[73] Assignee: Mycogen Corporation, San Diego, Calif.

[21] Appl. No.: 158,232

[22] Filed: Nov. 24, 1993

Related U.S. Application Data

[63] Continuation-in-part of Ser. No. 797,645, Nov. 25, 1991, Pat. No. 5,268,297, and Ser. No. 887,980, May 22, 1992, abandoned, which is a continuation-in-part of Ser. No. 703,977, May 22, 1991, Pat. No. 5,260,058.

[51] Int. Cl.$^6$ .......................... C07K 14/325; C12N 1/20
[52] U.S. Cl. ......................... 530/350; 435/252.5
[58] Field of Search .................. 435/69.1, 71.1, 435/71.2, 252.5; 530/350

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,771,131 | 9/1988 | Hernnstadt et al. | 536/23.71 |
| 4,797,276 | 1/1989 | Hernnstadt et al. | 424/84 |
| 4,849,217 | 6/1989 | Soares et al. | 424/93.461 |
| 4,853,331 | 8/1989 | Hernnstadt et al. | 435/252.3 |
| 4,918,006 | 4/1990 | Ellar et al. | 435/69.1 |
| 4,948,734 | 8/1990 | Edwards et al. | 435/252.5 |
| 5,151,363 | 9/1992 | Payne | 435/252.5 |
| 5,196,342 | 3/1993 | Donovan | 435/320.1 |
| 5,208,077 | 5/1993 | Proctor et al. | 427/461 |
| 5,229,112 | 7/1993 | Obukowicz et al. | 435/252.5 |
| 5,260,058 | 11/1993 | Payne et al. | 435/252.5 |
| 5,268,297 | 12/1993 | Payne et al. | 435/252.5 |

FOREIGN PATENT DOCUMENTS 200344  12/1986  European Pat. Off. .

OTHER PUBLICATIONS

Wahl et al. (1987) Methods in Enzymology, vol. 152, pp. 399–407.

Maniatis et al. (1982) Molecular Cloning: A Laboratory Manual (Cold Spring Harbor Laboratory, Cold Spring Harbor), pp. 324–325.

George et al. (1988) in Macromolecular Sequencing and Synthesis (Alan R. Liss, N.Y.) pp. 127–149.

Vobrazkova et al. (1976) Angew. Parasitol., vol. 17, pp. 94–99.

Prefontaine et al. (1987) Applied and Environmental Microbiology vol. 53, pp. 2808–2814.

Haider et al. (1987) Gene, vol. 52, pp. 285–290.

Gaertner, F. L. Kim (1988) "Current Applied Recombinant DNA Projects" TIBTECH 6:S4–S7.

Gaertner, F. (1989) "Cellular Delivery Systems for Insecticidal Proteins: Living and Non–Living Microorganisms" in Controlled Deliver of Crop–Protection Agents, pp. 245–255.

Couch, T. L. (1980) "Mosquito Pathogenicity of *Bacillus thuringiensis* var. israelensis" Developments in Industrial Microbiology 22:61–76.

Beegle, C. C. (1978) "Use of Entomogenous Bacteria in Agroecosystems" Developments in Industrial Microbiology 20:97–104.

Krieg, V. A. et al. (1983) "*Bacillus thuringiensis* var. tenebrionis: ein neuer, gegenuber Larven von Coleopteren wirksamer Pathotyp" Z. ang. Ent. 96:500–508.

Hofte, H., H. R. Whiteley (1989) "Insecticidal Crystal Proteins of *Bacillus thuringiensis*" Microbiological Reviews 52(2):242–255.

Feitelson, J. S. et al. (1992) "*Bacillus thuringiensis:* Insects and Beyond" Bio/Technology 10:271–275.

Schnepf, H. E., H. R. Whiteley (1981) "Cloning and expression of the *Bacillus thuringiensis* crystal protein gene in *Escherichia coli*" Proc. Natl. Acad. Sci. USA 78(5):2893–2897.

Holldobler, B., E. O. Wilson (1990) "The Harvesting Ants" in the Ants, pp. 609–617.

Habermehl, G. G. (1981) "Formicinae (Ants)" in Venomous Animals and Their Toxins, pp. 81–83.

Akre, R. D. et al. (1989) "Carpenter Ants: Their Biology and Control" Ext. Bull. Washington State Univ. Coop. Ext. Serv., No. EB 0818, pp. 1–6.

Beatson, S. H. (1972) "Pharoah's Ants as Pathogen Vectors in Hospitals" The Lacent 1:425–427.

Ebeling, W. (1978) Urban Entomology, UC Press, Berkeley, CA, (**not included) pp. 267–269.

*Primary Examiner*—Mindy Fleisher
*Assistant Examiner*—Philip W. Carter
*Attorney, Agent, or Firm*—Saliwanchik & Saliwanchik

[57] ABSTRACT

Novel *Bacillus thuringiensis* toxins with hymenopteran activity are described.

1 Claim, 5 Drawing Sheets

Fig. 1

1. *Bacillus thuringiensis* PS140E2
2. *Bacillus thuringiensis* PS86Q3

Fig. 2

A. *Bacillus thuringiensis* PS211B2
B. Protein Standard

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 4155 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( B ) STRAIN: PS17
( C ) INDIVIDUAL ISOLATE: PS17a ( v i i ) IMMEDIATE SOURCE:
( B ) CLONE: E. coli NM522(pMYC1627) NRRL B-18651

( x i ) SEQUENCE DESCRIPTION: SEQ ID NO:1:

```
ATGGCAATTT TAAATGAATT ATATCCATCT GTACCTTATA ATGTATTGGC GTATACGCCA     60
CCCTCTTTTT TACCTGATGC GGGTACACAA GCTACACCTG CTGACTTAAC AGCTTATGAA    120
CAATTGTTGA AAAATTTAGA AAAAGGGATA AATGCTGGAA CTTATTCGAA AGCAATAGCT    180
GATGTACTTA AAGGTATTTT TATAGATGAT ACAATAAATT ATCAAACATA TGTAAATATT    240
GGTTTAAGTT TAATTACATT AGCTGTACCG GAAATTGGTA TTTTTACACC TTTCATCGGT    300
TTGTTTTTTG CTGCATTGAA TAAACATGAT GCTCCACCTC CTCCTAATGC AAAAGATATA    360
TTTGAGGCTA TGAAACCAGC GATTCAAGAG ATGATTGATA GAACTTTAAC TGCGGATGAG    420
CAAACATTTT TAAATGGGGA AATAAGTGGT TTACAAAATT TAGCAGCAAG ATACCAGTCT    480
ACAATGGATG ATATTCAAAG CCATGGAGGA TTTAATAAGG TAGATTCTGG ATTAATTAAA    540
AAGTTTACAG ATGAGGTACT ATCTTTAAAT AGTTTTTATA CAGATCGTTT ACCTGTATTT    600
ATTACAGATA ATACAGCGGA TCGAACTTTG TTAGGTCTTC CTTATTATGC TATACTTGCG    660
AGCATGCATC TTATGTTATT AAGAGATATC ATTACTAAGG GTCCGACATG GGATTCTAAA    720
ATTAATTTCA CACCAGATGC AATTGATTCC TTTAAAACCG ATATTAAAAA TAATATAAAG    780
CTTTACTCTA AAACTATTTA TGACGTATTT CAGAAGGGAC TTGCTTCATA CGGAACGCCT    840
TCTGATTTAG AGTCCTTTGC AAAAAAACAA AAATATATTG AAATTATGAC AACACATTGT    900
TTAGATTTTG CAAGATTGTT TCCTACTTTT GATCCAGATC TTTATCCAAC AGGATCAGGT    960
GATATAAGTT TACAAAAAAC ACGTAGAATT CTTTCTCCTT TTATCCCTAT ACGTACTGCA   1020
GATGGGTTAA CATTAAATAA TACTTCAATT GATACTTCAA ATTGGCCTAA TTATGAAAAT   1080
GGGAATGGCG CGTTTCCAAA CCCAAAAGAA AGAATATTAA AACAATTCAA ACTGTATCCT   1140
AGTTGGAGAG CGGGACAGTA CGGTGGGCTT TTACAACCTT ATTTATGGGC AATAGAAGTC   1200
CAAGATTCTG TAGAGACTCG TTTGTATGGG CAGCTTCCAG CTGTAGATCC ACAGGCAGGG   1260
CCTAATTATG TTTCCATAGA TTCTTCTAAT CCAATCATAC AAATAAATAT GGATACTTGG   1320
```

```
AAAACACCAC CACAAGGTGC GAGTGGGTGG AATACAAATT TAATGAGAGG AAGTGTAAGC    1380
GGGTTAAGTT TTTTACAACG AGATGGTACG AGACTTAGTG CTGGTATGGG TGGTGGTTTT    1440
GCTGATACAA TATATAGTCT CCCTGCAACT CATTATCTTT CTTATCTCTA TGGAACTCCT    1500
TATCAAACTT CTGATAACTA TTCTGGTCAC GTTGGTGCAT TGGTAGGTGT GAGTACGCCT    1560
CAAGAGGCTA CTCTTCCTAA TATTATAGGT CAACCAGATG AACAGGGAAA TGTATCTACA    1620
ATGGGATTTC CGTTTGAAAA AGCTTCTTAT GGAGGTACAG TTGTTAAAGA ATGGTAAAT     1680
GGTGCGAATG CGATGAAGCT TTCTCCTGGG CAATCTATAG GTATTCCTAT TACAAATGTA    1740
ACAAGTGGAG AATATCAAAT TCGTTGTCGT TATGCAAGTA ATGATAATAC TAACGTTTTC    1800
TTTAATGTAG ATACTGGTGG AGCAAATCCA ATTTTCCAAC AGATAAACTT TGCATCTACT    1860
GTAGATAATA ATACGGGAGT ACAAGGAGCA AATGGTGTCT ATGTAGTCAA ATCTATTGCT    1920
ACAACTGATA ATTCTTTTAC AGAAATTCCT GCGAAGACGA TTAATGTTCA TTTAACCAAC    1980
CAAGGTTCTT CTGATGTCTT TTTAGACCGT ATTGAATTTA TACCTTTTTC TCTACCTCTT    2040
ATATATCATG GAAGTTATAA TACTTCATCA GGTGCAGATG ATGTTTTATG GTCTTCTTCA    2100
AATATGAATT ACTACGATAT AATAGTAAAT GGTCAGGCCA ATAGTAGTAG TATCGCTAGT    2160
TCTATGCATT TGCTTAATAA AGGAAAAGTG ATAAAAACAA TTGATATTCC AGGGCATTCG    2220
GAAACCTTCT TTGCTACGTT CCCAGTTCCA GAAGGATTTA ATGAAGTTAG AATTCTTGCT    2280
GGCCTTCCAG AAGTTAGTGG AAATATTACC GTACAATCTA ATAATCCGCC TCAACCTAGT    2340
AATAATGGTG GTGGTGATGG TGGTGGTAAT GGTGGTGGTG ATGGTGGTCA ATACAATTTT    2400
TCTTTAAGCG GATCTGATCA TACGACTATT TATCATGGAA AACTTGAAAC TGGGATTCAT    2460
GTACAAGGTA ATTATACCTA TACAGGTACT CCCGTATTAA TACTGAATGC TTACAGAAAT    2520
AATACTGTAG TATCAAGCAT TCCAGTATAT TCTCCTTTTG ATATAACTAT ACAGACAGAA    2580
GCTGATAGCC TTGAGCTTGA ACTACAACCT AGATATGGTT TTGCCACAGT GAATGGTACT    2640
GCAACAGTAA AAAGTCCTAA TGTAAATTAC GATAGATCAT TTAAACTCCC AATAGACTTA    2700
CAAAATATCA ACACAAGT AAATGCATTA TTCGCATCTG GAACACAAAA TATGCTTGCT     2760
CATAATGTAA GTGATCATGA TATTGAAGAA GTTGTATTAA AAGTGGATGC CTTATCAGAT    2820
GAAGTATTTG GAGATGAGAA GAAGGCTTTA CGTAAATTGG TGAATCAAGC AAAACGTTTG    2880
AGTAGAGCAA GAAATCTTCT GATAGGTGGG AGTTTTGAAA ATTGGGATGC ATGGTATAAA    2940
GGAAGAAATG TAGTAACTGT ATCTGATCAT GAACTATTTA AGAGTGATCA TGTATTATTA    3000
CCACCACCAG GATTGTCTCC ATCTTATATT TTCCAAAAAG TGGAGGAATC TAAATTAAAA    3060
CCAAATACAC GTTATATTGT TTCTGGATTC ATCGCACATG GAAAAGACCT AGAAATTGTT    3120
GTTTCACGTT ATGGGCAAGA AGTGCAAAAG GTCGTGCAAG TTCCTTATGG AGAAGCATTC    3180
CCGTTAACAT CAAATGGACC AGTTTGTTGT CCCCCACGTT CTACAAGTAA TGGAACCTTA    3240
GGAGATCCAC ATTTCTTTAG TTACAGTATC GATGTAGGTG CACTAGATTT ACAAGCAAAC    3300
CCTGGTATTG AATTTGGTCT TCGTATTGTA AATCCAACTG GAATGGCACG CGTAAGCAAT    3360
TTGGAAATTC GTGAAGATCG TCCATTAGCA GCAAATGAAA TACGACAAGT ACAACGTGTC    3420
GCAAGAAATT GGAGAACCGA GTATGAGAAA GAACGTGCGG AAGTAACAAG TTTAATTCAA    3480
CCTGTTATCA ATCGAATCAA CGGATTGTAT GAAAATGGAA ATTGGACGG TTCTATTCGT     3540
TCAGATATTT CGTATCAGAA TATAGACGCG ATTGTATTAC CAACGTTACC AAAGTTACGC    3600
CATTGGTTTA TGTCAGATAG ATTCAGTGAA CAAGGAGATA TAATGGCTAA ATTCCAAGGT    3660
GCATTAAATC GTGCGTATGC ACAACTGGAA CAAAGTACGC TTCTGCATAA TGGTCATTTT    3720
```

```
ACAAAAGATG    CAGCTAATTG    GACAATAGAA    GGCGATGCAC    ATCAGATAAC    ACTAGAAGAT    3780

GGTAGACGTG    TATTGCGACT    TCCAGATTGG    TCTTCGAGTG    TATCTCAAAT    GATTGAAATC    3840

GAGAATTTTA    ATCCAGATAA    AGAATACAAC    TTAGTATTCC    ATGGGCAAGG    AGAAGGAACG    3900

GTTACGTTGG    AGCATGGAGA    AGAAACAAAA    TATATAGAAA    CGCATACACA    TCATTTTGCG    3960

AATTTTACAA    CTTCTCAACG    TCAAGGACTC    ACGTTTGAAT    CAAATAAAGT    GACAGTGACC    4020

ATTTCTTCAG    AAGATGGAGA    ATTCTTAGTG    GATAATATTG    CGCTTGTGGA    AGCTCCTCTT    4080

CCTACAGATG    ACCAAAATTC    TGAGGGAAAT    ACGGCTTCCA    GTACGAATAG    CGATACAAGT    4140

ATGAACAACA    ATCAA                                                                4155
```

( 2 ) INFORMATION FOR SEQ ID NO:2:

( i ) SEQUENCE CHARACTERISTICS:
        ( A ) LENGTH: 1385 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: BACILLUS THURINGIENSIS
        ( B ) STRAIN: PS17
        ( C ) INDIVIDUAL ISOLATE: PS17a ( v i i ) IMMEDIATE SOURCE:
( B ) CLONE: E. coli NM522(pMYC1627) NRRL B-18651

( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ala | Ile | Leu | Asn | Glu | Leu | Tyr | Pro | Ser | Val | Pro | Tyr | Asn | Val | Leu |
| 1 | | | | 5 | | | | | 10 | | | | | 15 | |
| Ala | Tyr | Thr | Pro | Pro | Ser | Phe | Leu | Pro | Asp | Ala | Gly | Thr | Gln | Ala | Thr |
| | | | 20 | | | | | 25 | | | | | 30 | | |
| Pro | Ala | Asp | Leu | Thr | Ala | Tyr | Glu | Gln | Leu | Leu | Lys | Asn | Leu | Glu | Lys |
| | | 35 | | | | | 40 | | | | | 45 | | | |
| Gly | Ile | Asn | Ala | Gly | Thr | Tyr | Ser | Lys | Ala | Ile | Ala | Asp | Val | Leu | Lys |
| | 50 | | | | | 55 | | | | | 60 | | | | |
| Gly | Ile | Phe | Ile | Asp | Asp | Thr | Ile | Asn | Tyr | Gln | Thr | Tyr | Val | Asn | Ile |
| 65 | | | | | 70 | | | | | 75 | | | | | 80 |
| Gly | Leu | Ser | Leu | Ile | Thr | Leu | Ala | Val | Pro | Glu | Ile | Gly | Ile | Phe | Thr |
| | | | | 85 | | | | | 90 | | | | | 95 | |
| Pro | Phe | Ile | Gly | Leu | Phe | Phe | Ala | Ala | Leu | Asn | Lys | His | Asp | Ala | Pro |
| | | | 100 | | | | | 105 | | | | | 110 | | |
| Pro | Pro | Pro | Asn | Ala | Lys | Asp | Ile | Phe | Glu | Ala | Met | Lys | Pro | Ala | Ile |
| | | 115 | | | | | 120 | | | | | 125 | | | |
| Gln | Glu | Met | Ile | Asp | Arg | Thr | Leu | Thr | Ala | Asp | Glu | Gln | Thr | Phe | Leu |
| | 130 | | | | | 135 | | | | | 140 | | | | |
| Asn | Gly | Glu | Ile | Ser | Gly | Leu | Gln | Asn | Leu | Ala | Ala | Arg | Tyr | Gln | Ser |
| 145 | | | | | 150 | | | | | 155 | | | | | 160 |
| Thr | Met | Asp | Asp | Ile | Gln | Ser | His | Gly | Gly | Phe | Asn | Lys | Val | Asp | Ser |
| | | | | 165 | | | | | 170 | | | | | 175 | |
| Gly | Leu | Ile | Lys | Lys | Phe | Thr | Asp | Glu | Val | Leu | Ser | Leu | Asn | Ser | Phe |
| | | | 180 | | | | | 185 | | | | | 190 | | |
| Tyr | Thr | Asp | Arg | Leu | Pro | Val | Phe | Ile | Thr | Asp | Asn | Thr | Ala | Asp | Arg |
| | | 195 | | | | | 200 | | | | | 205 | | | |

```
Thr  Leu  Leu  Gly  Leu  Pro  Tyr  Tyr  Ala  Ile  Leu  Ala  Ser  Met  His  Leu
     210                 215                 220
Met  Leu  Leu  Arg  Asp  Ile  Ile  Thr  Lys  Gly  Pro  Thr  Trp  Asp  Ser  Lys
225                      230                 235                           240
Ile  Asn  Phe  Thr  Pro  Asp  Ala  Ile  Asp  Ser  Phe  Lys  Thr  Asp  Ile  Lys
               245                 250                           255
Asn  Asn  Ile  Lys  Leu  Tyr  Ser  Lys  Thr  Ile  Tyr  Asp  Val  Phe  Gln  Lys
          260                 265                      270
Gly  Leu  Ala  Ser  Tyr  Gly  Thr  Pro  Ser  Asp  Leu  Glu  Ser  Phe  Ala  Lys
          275                 280                      285
Lys  Gln  Lys  Tyr  Ile  Glu  Ile  Met  Thr  Thr  His  Cys  Leu  Asp  Phe  Ala
290                      295                      300
Arg  Leu  Phe  Pro  Thr  Phe  Asp  Pro  Asp  Leu  Tyr  Pro  Thr  Gly  Ser  Gly
305                      310                 315                           320
Asp  Ile  Ser  Leu  Gln  Lys  Thr  Arg  Arg  Ile  Leu  Ser  Pro  Phe  Ile  Pro
               325                 330                           335
Ile  Arg  Thr  Ala  Asp  Gly  Leu  Thr  Leu  Asn  Asn  Thr  Ser  Ile  Asp  Thr
               340                 345                      350
Ser  Asn  Trp  Pro  Asn  Tyr  Glu  Asn  Gly  Asn  Gly  Ala  Phe  Pro  Asn  Pro
          355                      360                      365
Lys  Glu  Arg  Ile  Leu  Lys  Gln  Phe  Lys  Leu  Tyr  Pro  Ser  Trp  Arg  Ala
370                      375                      380
Gly  Gln  Tyr  Gly  Gly  Leu  Leu  Gln  Pro  Tyr  Leu  Trp  Ala  Ile  Glu  Val
385                      390                      395                      400
Gln  Asp  Ser  Val  Glu  Thr  Arg  Leu  Tyr  Gly  Leu  Pro  Ala  Val  Asp
                    405                      410                      415
Pro  Gln  Ala  Gly  Pro  Asn  Tyr  Val  Ser  Ile  Asp  Ser  Ser  Asn  Pro  Ile
               420                      425                      430
Ile  Gln  Ile  Asn  Met  Asp  Thr  Trp  Lys  Thr  Pro  Pro  Gln  Gly  Ala  Ser
          435                      440                      445
Gly  Trp  Asn  Thr  Asn  Leu  Met  Arg  Gly  Ser  Val  Ser  Gly  Leu  Ser  Phe
     450                      455                 460
Leu  Gln  Arg  Asp  Gly  Thr  Arg  Leu  Ser  Ala  Gly  Met  Gly  Gly  Gly  Phe
465                      470                 475                           480
Ala  Asp  Thr  Ile  Tyr  Ser  Leu  Pro  Ala  Thr  His  Tyr  Leu  Ser  Tyr  Leu
               485                 490                      495
Tyr  Gly  Thr  Pro  Tyr  Gln  Thr  Ser  Asp  Asn  Tyr  Ser  Gly  His  Val  Gly
               500                 505                      510
Ala  Leu  Val  Gly  Val  Ser  Thr  Pro  Gln  Glu  Ala  Thr  Leu  Pro  Asn  Ile
          515                 520                      525
Ile  Gly  Gln  Pro  Asp  Glu  Gln  Gly  Asn  Val  Ser  Thr  Met  Gly  Phe  Pro
     530                 535                      540
Phe  Glu  Lys  Ala  Ser  Tyr  Gly  Gly  Thr  Val  Val  Lys  Glu  Trp  Leu  Asn
545                 550                      555                           560
Gly  Ala  Asn  Ala  Met  Lys  Leu  Ser  Pro  Gly  Gln  Ser  Ile  Gly  Ile  Pro
               565                      570                      575
Ile  Thr  Asn  Val  Thr  Ser  Gly  Glu  Tyr  Gln  Ile  Arg  Cys  Arg  Tyr  Ala
               580                 585                      590
Ser  Asn  Asp  Asn  Thr  Asn  Val  Phe  Phe  Asn  Val  Asp  Thr  Gly  Gly  Ala
          595                      600                      605
Asn  Pro  Ile  Phe  Gln  Gln  Ile  Asn  Phe  Ala  Ser  Thr  Val  Asp  Asn  Asn
     610                 615                      620
Thr  Gly  Val  Gln  Gly  Ala  Asn  Gly  Val  Tyr  Val  Val  Lys  Ser  Ile  Ala
625                 630                      635                           640
```

```
Thr Thr Asp Asn Ser Phe Thr Glu Ile Pro Ala Lys Thr Ile Asn Val
            645             650             655
His Leu Thr Asn Gln Gly Ser Ser Asp Val Phe Leu Asp Arg Ile Glu
            660             665             670
Phe Ile Pro Phe Ser Leu Pro Leu Ile Tyr His Gly Ser Tyr Asn Thr
            675             680             685
Ser Ser Gly Ala Asp Asp Val Leu Trp Ser Ser Ser Asn Met Asn Tyr
            690             695             700
Tyr Asp Ile Ile Val Asn Gly Gln Ala Asn Ser Ser Ile Ala Ser
705             710             715             720
Ser Met His Leu Leu Asn Lys Gly Lys Val Ile Lys Thr Ile Asp Ile
            725             730             735
Pro Gly His Ser Glu Thr Phe Phe Ala Thr Phe Pro Val Pro Glu Gly
            740             745             750
Phe Asn Glu Val Arg Ile Leu Ala Gly Leu Pro Glu Val Ser Gly Asn
            755             760             765
Ile Thr Val Gln Ser Asn Asn Pro Pro Gln Pro Ser Asn Asn Gly Gly
            770             775             780
Gly Asp Gly Gly Gly Asn Gly Gly Asp Gly Gly Gln Tyr Asn Phe
785             790             795             800
Ser Leu Ser Gly Ser Asp His Thr Thr Ile Tyr His Gly Lys Leu Glu
            805             810             815
Thr Gly Ile His Val Gln Gly Asn Tyr Thr Tyr Thr Gly Thr Pro Val
            820             825             830
Leu Ile Leu Asn Ala Tyr Arg Asn Asn Thr Val Val Ser Ser Ile Pro
            835             840             845
Val Tyr Ser Pro Phe Asp Ile Thr Ile Gln Thr Glu Ala Asp Ser Leu
850             855             860
Glu Leu Glu Leu Gln Pro Arg Tyr Gly Phe Ala Thr Val Asn Gly Thr
865             870             875             880
Ala Thr Val Lys Ser Pro Asn Val Asn Tyr Asp Arg Ser Phe Lys Leu
            885             890             895
Pro Ile Asp Leu Gln Asn Ile Thr Thr Gln Val Asn Ala Leu Phe Ala
            900             905             910
Ser Gly Thr Gln Asn Met Leu Ala His Asn Val Ser Asp His Asp Ile
            915             920             925
Glu Glu Val Val Leu Lys Val Asp Ala Leu Ser Asp Glu Val Phe Gly
            930             935             940
Asp Glu Lys Lys Ala Leu Arg Lys Leu Val Asn Gln Ala Lys Arg Leu
945             950             955             960
Ser Arg Ala Arg Asn Leu Leu Ile Gly Gly Ser Phe Glu Asn Trp Asp
            965             970             975
Ala Trp Tyr Lys Gly Arg Asn Val Val Thr Val Ser Asp His Glu Leu
            980             985             990
Phe Lys Ser Asp His Val Leu Leu Pro Pro Pro Gly Leu Ser Pro Ser
            995             1000            1005
Tyr Ile Phe Gln Lys Val Glu Glu Ser Lys Leu Lys Pro Asn Thr Arg
            1010            1015            1020
Tyr Ile Val Ser Gly Phe Ile Ala His Gly Lys Asp Leu Glu Ile Val
            1025            1030            1035            1040
Val Ser Arg Tyr Gly Gln Glu Val Gln Lys Val Val Gln Val Pro Tyr
            1045            1050            1055
Gly Glu Ala Phe Pro Leu Thr Ser Asn Gly Pro Val Cys Cys Pro Pro
```

```
                           1060                    1065                      1070
     Arg  Ser  Thr  Ser  Asn  Gly  Thr  Leu  Gly  Asp  Pro  His  Phe  Phe  Ser  Tyr
                    1075                    1080                      1085

Ser  Ile  Asp  Val  Gly  Ala  Leu  Asp  Leu  Gln  Ala  Asn  Pro  Gly  Ile  Glu
                    1090                    1095                      1100

Phe  Gly  Leu  Arg  Ile  Val  Asn  Pro  Thr  Gly  Met  Ala  Arg  Val  Ser  Asn
     1105                     1110                     1115                     1120

Leu  Glu  Ile  Arg  Glu  Asp  Arg  Pro  Leu  Ala  Ala  Asn  Glu  Ile  Arg  Gln
                         1125                     1130                     1135

Val  Gln  Arg  Val  Ala  Arg  Asn  Trp  Arg  Thr  Glu  Tyr  Glu  Lys  Glu  Arg
                    1140                    1145                      1150

Ala  Glu  Val  Thr  Ser  Leu  Ile  Gln  Pro  Val  Ile  Asn  Arg  Ile  Asn  Gly
                    1155                    1160                      1165

Leu  Tyr  Glu  Asn  Gly  Asn  Trp  Asn  Gly  Ser  Ile  Arg  Ser  Asp  Ile  Ser
          1170                     1175                     1180

Tyr  Gln  Asn  Ile  Asp  Ala  Ile  Val  Leu  Pro  Thr  Leu  Pro  Lys  Leu  Arg
     1185                     1190                     1195                     1200

His  Trp  Phe  Met  Ser  Asp  Arg  Phe  Ser  Glu  Gln  Gly  Asp  Ile  Met  Ala
                         1205                     1210                     1215

Lys  Phe  Gln  Gly  Ala  Leu  Asn  Arg  Ala  Tyr  Ala  Gln  Leu  Glu  Gln  Ser
                    1220                    1225                      1230

Thr  Leu  Leu  His  Asn  Gly  His  Phe  Thr  Lys  Asp  Ala  Ala  Asn  Trp  Thr
                    1235                    1240                      1245

Ile  Glu  Gly  Asp  Ala  His  Gln  Ile  Thr  Leu  Glu  Asp  Gly  Arg  Arg  Val
          1250                     1255                     1260

Leu  Arg  Leu  Pro  Asp  Trp  Ser  Ser  Ser  Val  Ser  Gln  Met  Ile  Glu  Ile
     1265                     1270                     1275                     1280

Glu  Asn  Phe  Asn  Pro  Asp  Lys  Glu  Tyr  Asn  Leu  Val  Phe  His  Gly  Gln
                         1285                     1290                     1295

Gly  Glu  Gly  Thr  Val  Thr  Leu  Glu  His  Gly  Glu  Glu  Thr  Lys  Tyr  Ile
                    1300                    1305                      1310

Glu  Thr  His  Thr  His  His  Phe  Ala  Asn  Phe  Thr  Thr  Ser  Gln  Arg  Gln
                    1315                    1320                      1325

Gly  Leu  Thr  Phe  Glu  Ser  Asn  Lys  Val  Thr  Val  Thr  Ile  Ser  Ser  Glu
                    1330                    1335                      1340

Asp  Gly  Glu  Phe  Leu  Val  Asp  Asn  Ile  Ala  Leu  Val  Glu  Ala  Pro  Leu
     1345                     1350                     1355                     1360

Pro  Thr  Asp  Asp  Gln  Asn  Ser  Glu  Gly  Asn  Thr  Ala  Ser  Ser  Thr  Asn
                         1365                     1370                     1375

Ser  Asp  Thr  Ser  Met  Asn  Asn  Asn  Gln
                    1380                    1385
```

( 2 ) INFORMATION FOR SEQ ID NO:3:

( i ) SEQUENCE CHARACTERISTICS:
        ( A ) LENGTH: 3867 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( B ) STRAIN: P (C) INDIVIDUAL ISOLATE: PS17b (vii) IMMEDIATE SOURCE:
    (B) CLONE: E. coli NM522(pMYC1628) NRRL B-18652

(xi) SEQUENCE DESCRIPTION: SEQ ID NO:3:

```
ATGGCAATTT TAAATGAATT ATATCCATCT GTACCTTATA ATGTATTGGC GTATACGCCA      60
CCCTCTTTTT TACCTGATGC GGGTACACAA GCTACACCTG CTGACTTAAC AGCTTATGAA     120
CAATTGTTGA AAAATTTAGA AAAAGGGATA AATGCTGGAA CTTATTCGAA AGCAATAGCT     180
GATGTACTTA AAGGTATTTT TATAGATGAT ACAATAAATT ATCAAACATA TGTAAATATT     240
GGTTTAAGTT TAATTACATT AGCTGTACCG GAAATTGGTA TTTTACACC  TTTCATCGGT     300
TTGTTTTTTG CTGCATTGAA TAAACATGAT GCTCCACCTC CTCCTAATGC AAAAGATATA     360
TTTGAGGCTA TGAAACCAGC GATTCAAGAG ATGATTGATA GAACTTTAAC TGCGGATGAG     420
CAAACATTTT TAAATGGGGA AATAAGTGGT TTACAAAATT TAGCAGCAAG ATACCAGTCT     480
ACAATGGATG ATATTCAAAG CCATGGAGGA TTTAATAAGG TAGATTCTGG ATTAATTAAA     540
AAGTTTACAG ATGAGGTACT ATCTTTAAAT AGTTTTTATA CAGATCGTTT ACCTGTATTT     600
ATTACAGATA ATACAGCGGA TCGAACTTTG TTAGGTCTTC CTTATTATGC TATACTTGCG     660
AGCATGCATC TTATGTTATT AAGAGATATC ATTACTAAGG GTCGACATG  GGATTCTAAA     720
ATTAATTTCA CACCAGATGC AATTGATTCC TTTAAAACCG ATATTAAAAA TAATATAAAG     780
CTTTACTCTA AAACTATTTA TGACGTATTT CAGAAGGGAC TTGCTTCATA CGGAACGCCT     840
TCTGATTTAG AGTCCTTTGC AAAAAAACAA AAATATATTG AAATTATGAC AACACATTGT     900
TTAGATTTTG CAAGATTGTT TCCTACTTTT GATCCAGATC TTTATCCAAC AGGATCAGGT     960
GATATAAGTT TACAAAAAAC ACGTAGAATT CTTTCTCCTT TTATCCCTAT ACGTACTGCA    1020
GATGGGTTAA CATTAAATAA TACTTCAATT GATACTTCAA ATTGGCCTAA TTATGAAAAT    1080
GGGAATGGCG CGTTTCCAAA CCCAAAAGAA AGAATATTAA AACAATTCAA ACTGTATCCT    1140
AGTTGGAGAG CGGCACAGTA CGGTGGGCTT TTACAACCTT ATTTATGGGC AATAGAAGTC    1200
CAAGATTCTG TAGAGACTCG TTTGTATGGG CAGCTTCCAG CTGTAGATCC ACAGGCAGGG    1260
CCTAATTATG TTTCCATAGA TTCTTCTAAT CCAATCATAC AAATAAATAT GGATACTTGG    1320
AAAACACCAC CACAAGGTGC GAGTGGGTGG AATACAAATT TAATGAGAGG AAGTGTAAGC    1380
GGGTTAAGTT TTTTACAACG AGATGGTACG AGACTTAGTG CTGGTATGGG TGGTGGTTTT    1440
GCTGATACAA TATATAGTCT CCCTGCAACT CATTATCTTT CTTATCTCTA TGGAACTCCT    1500
TATCAAACTT CTGATAACTA TTCTGGTCAC GTTGGTGCAT TGGTAGGTGT GAGTACGCCT    1560
CAAGAGGCTA CTCTTCCTAA TATTATAGGT CAACCAGATG AACAGGGAAA TGTATCTACA    1620
ATGGGATTTC CGTTTGAAAA AGCTTCTTAT GGAGGTACAG TTGTTAAAGA ATGGTTAAAT    1680
GGTGCGAATG CGATGAAGCT TTCTCCTGGG CAATCTATAG GTATTCCTAT TACAAATGTA    1740
ACAAGTGGAG AATATCAAAT TCGTTGTCGT TATGCAAGTA ATGATAATAC TAACGTTTTC    1800
TTTAATGTAG ATACTGGTGG AGCAAATCCA ATTTTCCAAC AGATAAACTT TGCATCTACT    1860
GTAGATAATA ATACGGGAGT ACAAGGAGCA ATGGTGTCT  ATGTAGTCAA ATCTATTGCT    1920
ACAACTGATA ATTCTTTTAC AGTAAAAATT CCTGCGAAGA CGATTAATGT TCATTTAACC    1980
AACCAAGGTT CTTCTGATGT CTTTTTAGAT CGTATTGAGT TTGTTCCAAT TCTAGAATCA    2040
AATACTGTAA CTATATTCAA CAATTCATAT ACTACAGGTT CAGCAAATCT TATACCAGCA    2100
ATAGCTCCTC TTTGGAGTAC TAGTTCAGAT AAAGCCCTTA CAGGTTCTAT GTCAATAACA    2160
GGTCGAACTA CCCCTAACAG TGATGATGCT TTGCTTCGAT TTTTAAAAAC TAATTATGAT    2220
```

| | | | | | | |
|---|---|---|---|---|---|---|
| ACACAAACCA | TTCCTATTCC | GGGTTCCGGA | AAAGATTTTA | CAAATACTCT | AGAAATACAA | 2280 |
| GACATAGTTT | CTATTGATAT | TTTTGTCGGA | TCTGGTCTAC | ATGGATCCGA | TGGATCTATA | 2340 |
| AAATTAGATT | TTACCAATAA | TAATAGTGGT | AGTGGTGGCT | CTCCAAAGAG | TTTCACCGAG | 2400 |
| CAAATGATT | TAGAGAATAT | CACAACACAA | GTGAATGCTC | TATTCACATC | TAATACACAA | 2460 |
| GATGCACTTG | CAACAGATGT | GAGTGATCAT | GATATTGAAG | AAGTGGTTCT | AAAAGTAGAT | 2520 |
| GCATTATCTG | ATGAAGTGTT | TGGAAAAGAG | AAAAAAACAT | TGCGTAAATT | TGTAAATCAA | 2580 |
| GCGAAGCGCT | TAAGCAAGGC | GCGTAATCTC | CTGGTAGGAG | GCAATTTTGA | TAACTTGGAT | 2640 |
| GCTTGGTATA | GAGGAAGAAA | TGTAGTAAAC | GTATCTAATC | ACGAACTGTT | GAAGAGTGAT | 2700 |
| CATGTATTAT | TACCACCACC | AGGATTGTCT | CCATCTTATA | TTTTCCAAAA | AGTGGAGGAA | 2760 |
| TCTAAATTAA | AACGAAATAC | ACGTTATACG | GTTTCTGGAT | TTATTGCGCA | TGCAACAGAT | 2820 |
| TTAGAAATTG | TGGTTTCTCG | TTATGGGCAA | GAAATAAAGA | AAGTGGTGCA | AGTTCCTTAT | 2880 |
| GGAGAAGCAT | TCCCATTAAC | ATCAAGTGGA | CCAGTTTGTT | GTATCCCACA | TTCTACAAGT | 2940 |
| AATGGAACTT | TAGGCAATCC | ACATTTCTTT | AGTTACAGTA | TTGATGTAGG | TGCATTAGAT | 3000 |
| GTAGACACAA | ACCCTGGTAT | TGAATTCGGT | CTTCGTATTG | TAAATCCAAC | TGGAATGGCA | 3060 |
| CGCGTAAGCA | ATTTGGAAAT | TCGTGAAGAT | CGTCCATTAG | CAGCAAATGA | AATACGACAA | 3120 |
| GTACAACGTG | TCGCAAGAAA | TTGGAGAACC | GAGTATGAGA | AGAACGTGC | GGAAGTAACA | 3180 |
| AGTTTAATTC | AACCTGTTAT | CAATCGAATC | AATGGATTGT | ATGACAATGG | AAATTGGAAC | 3240 |
| GGTTCTATTC | GTTCAGATAT | TTCGTATCAG | AATATAGACG | CGATTGTATT | ACCAACGTTA | 3300 |
| CCAAAGTTAC | GCCATTGGTT | TATGTCAGAT | AGATTTAGTG | AACAAGGAGA | TATCATGGCT | 3360 |
| AAATTCCAAG | GTGCATTAAA | TCGTGCGTAT | GCACAACTGG | AACAAATAC | GCTTCTGCAT | 3420 |
| AATGGTCATT | TTACAAAAGA | TGCAGCCAAT | TGGACGGTAG | AAGGCGATGC | ACATCAGGTA | 3480 |
| GTATTAGAAG | ATGGTAAACG | TGTATTACGA | TTGCCAGATT | GGTCTTCGAG | TGTGTCTCAA | 3540 |
| ACGATTGAAA | TCGAGAATTT | TGATCCAGAT | AAAGAATATC | AATTAGTATT | TCATGGGCAA | 3600 |
| GGAGAAGGAA | CGGTTACGTT | GGAGCATGGA | GAAGAAACAA | AATATATAGA | AACGCATACA | 3660 |
| CATCATTTTG | CGAATTTTAC | AACTTCTCAA | CGTCAAGGAC | TCACGTTTGA | ATCAAATAAA | 3720 |
| GTGACAGTGA | CCATTCTTC | AGAAGATGGA | GAATTCTTAG | TGGATAATAT | TGCGCTTGTG | 3780 |
| GAAGCTCCTC | TTCCTACAGA | TGACCAAAAT | TCTGAGGGAA | ATACGGCTTC | CAGTACGAAT | 3840 |
| AGCGATACAA | GTATGAACAA | CAATCAA | | | | 3867 |

( 2 ) INFORMATION FOR SEQ ID NO:4:

( i ) SEQUENCE CHARACTERISTICS:
        ( A ) LENGTH: 1289 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: BACILLUS THURINGIENSIS
        ( B ) STRAIN: PS17
( C ) INDIVIDUAL ISOLATE: PS17b ( v i i ) IMMEDIATE SOURCE:
( B ) CLONE: E. coli NM522(pMYC1628) NRRL B-18652

( x i ) SEQUENCE DESCRIPTION: SEQ ID NO:4:

| Met | Ala | Ile | Leu | Asn | Glu | Leu | Tyr | Pro | Ser | Val | Pro | Tyr | Asn | Val | Leu |
| --- | --- | --- | --- | --- | --- | --- | --- | --- | --- | --- | --- | --- | --- | --- | --- |
| 1 | | | | 5 | | | | | 10 | | | | | 15 | |
| Ala | Tyr | Thr | Pro | Pro | Ser | Phe | Leu | Pro | Asp | Ala | Gly | Thr | Gln | Ala | Thr |
| | | | 20 | | | | | 25 | | | | | 30 | | |
| Pro | Ala | Asp | Leu | Thr | Ala | Tyr | Glu | Gln | Leu | Leu | Lys | Asn | Leu | Glu | Lys |
| | | | 35 | | | | | 40 | | | | | 45 | | |
| Gly | Ile | Asn | Ala | Gly | Thr | Tyr | Ser | Lys | Ala | Ile | Ala | Asp | Val | Leu | Lys |
| | | 50 | | | | | 55 | | | | | 60 | | | |
| Gly | Ile | Phe | Ile | Asp | Asp | Thr | Ile | Asn | Tyr | Gln | Thr | Tyr | Val | Asn | Ile |
| 65 | | | | | 70 | | | | | 75 | | | | | 80 |
| Gly | Leu | Ser | Leu | Ile | Thr | Leu | Ala | Val | Pro | Glu | Ile | Gly | Ile | Phe | Thr |
| | | | | 85 | | | | | 90 | | | | | 95 | |
| Pro | Phe | Ile | Gly | Leu | Phe | Phe | Ala | Ala | Leu | Asn | Lys | His | Asp | Ala | Pro |
| | | | 100 | | | | | 105 | | | | | 110 | | |
| Pro | Pro | Pro | Asn | Ala | Lys | Asp | Ile | Phe | Glu | Ala | Met | Lys | Pro | Ala | Ile |
| | | 115 | | | | | 120 | | | | | 125 | | | |
| Gln | Glu | Met | Ile | Asp | Arg | Thr | Leu | Thr | Ala | Asp | Glu | Gln | Thr | Phe | Leu |
| | 130 | | | | | 135 | | | | | 140 | | | | |
| Asn | Gly | Glu | Ile | Ser | Gly | Leu | Gln | Asn | Leu | Ala | Ala | Arg | Tyr | Gln | Ser |
| 145 | | | | | 150 | | | | | 155 | | | | | 160 |
| Thr | Met | Asp | Asp | Ile | Gln | Ser | His | Gly | Gly | Phe | Asn | Lys | Val | Asp | Ser |
| | | | | 165 | | | | | 170 | | | | | 175 | |
| Gly | Leu | Ile | Lys | Lys | Phe | Thr | Asp | Glu | Val | Leu | Ser | Leu | Asn | Ser | Phe |
| | | | 180 | | | | | 185 | | | | | 190 | | |
| Tyr | Thr | Asp | Arg | Leu | Pro | Val | Phe | Ile | Thr | Asp | Asn | Thr | Ala | Asp | Arg |
| | | 195 | | | | | 200 | | | | | 205 | | | |
| Thr | Leu | Leu | Gly | Leu | Pro | Tyr | Tyr | Ala | Ile | Leu | Ala | Ser | Met | His | Leu |
| | 210 | | | | | 215 | | | | | 220 | | | | |
| Met | Leu | Leu | Arg | Asp | Ile | Ile | Thr | Lys | Gly | Pro | Thr | Trp | Asp | Ser | Lys |
| 225 | | | | | 230 | | | | | 235 | | | | | 240 |
| Ile | Asn | Phe | Thr | Pro | Asp | Ala | Ile | Asp | Ser | Phe | Lys | Thr | Asp | Ile | Lys |
| | | | | 245 | | | | | 250 | | | | | 255 | |
| Asn | Asn | Ile | Lys | Leu | Tyr | Ser | Lys | Thr | Ile | Tyr | Asp | Val | Phe | Gln | Lys |
| | | | 260 | | | | | 265 | | | | | 270 | | |
| Gly | Leu | Ala | Ser | Tyr | Gly | Thr | Pro | Ser | Asp | Leu | Glu | Ser | Phe | Ala | Lys |
| | | 275 | | | | | 280 | | | | | 285 | | | |
| Lys | Gln | Lys | Tyr | Ile | Glu | Ile | Met | Thr | Thr | His | Cys | Leu | Asp | Phe | Ala |
| | 290 | | | | | 295 | | | | | 300 | | | | |
| Arg | Leu | Phe | Pro | Thr | Phe | Asp | Pro | Asp | Leu | Tyr | Pro | Thr | Gly | Ser | Gly |
| 305 | | | | | 310 | | | | | 315 | | | | | 320 |
| Asp | Ile | Ser | Leu | Gln | Lys | Thr | Arg | Arg | Ile | Leu | Ser | Pro | Phe | Ile | Pro |
| | | | | 325 | | | | | 330 | | | | | 335 | |
| Ile | Arg | Thr | Ala | Asp | Gly | Leu | Thr | Leu | Asn | Asn | Thr | Ser | Ile | Asp | Thr |
| | | | 340 | | | | | 345 | | | | | 350 | | |
| Ser | Asn | Trp | Pro | Asn | Tyr | Glu | Asn | Gly | Asn | Gly | Ala | Phe | Pro | Asn | Pro |
| | | 355 | | | | | 360 | | | | | 365 | | | |
| Lys | Glu | Arg | Ile | Leu | Lys | Gln | Phe | Lys | Leu | Tyr | Pro | Ser | Trp | Arg | Ala |
| | 370 | | | | | 375 | | | | | 380 | | | | |
| Ala | Gln | Tyr | Gly | Gly | Leu | Leu | Gln | Pro | Tyr | Leu | Trp | Ala | Ile | Glu | Val |
| 385 | | | | | 390 | | | | | 395 | | | | | 400 |
| Gln | Asp | Ser | Val | Glu | Thr | Arg | Leu | Tyr | Gly | Gln | Leu | Pro | Ala | Val | Asp |
| | | | | 405 | | | | | 410 | | | | | 415 | |

```
Pro  Gln  Ala  Gly  Pro  Asn  Tyr  Val  Ser  Ile  Asp  Ser  Ser  Asn  Pro  Ile
          420                 425                      430

Ile  Gln  Ile  Asn  Met  Asp  Thr  Trp  Lys  Thr  Pro  Pro  Gln  Gly  Ala  Ser
          435                 440                      445

Gly  Trp  Asn  Thr  Asn  Leu  Met  Arg  Gly  Ser  Val  Ser  Gly  Leu  Ser  Phe
     450                 455                 460

Leu  Gln  Arg  Asp  Gly  Thr  Arg  Leu  Ser  Ala  Gly  Met  Gly  Gly  Gly  Phe
465                      470                 475                           480

Ala  Asp  Thr  Ile  Tyr  Ser  Leu  Pro  Ala  Thr  His  Tyr  Leu  Ser  Tyr  Leu
               485                      490                           495

Tyr  Gly  Thr  Pro  Tyr  Gln  Thr  Ser  Asp  Asn  Tyr  Ser  Gly  His  Val  Gly
               500                 505                      510

Ala  Leu  Val  Gly  Val  Ser  Thr  Pro  Gln  Glu  Ala  Thr  Leu  Pro  Asn  Ile
          515                      520                 525

Ile  Gly  Gln  Pro  Asp  Glu  Gln  Gly  Asn  Val  Ser  Thr  Met  Gly  Phe  Pro
     530                      535                      540

Phe  Glu  Lys  Ala  Ser  Tyr  Gly  Gly  Thr  Val  Val  Lys  Glu  Trp  Leu  Asn
545                      550                      555                      560

Gly  Ala  Asn  Ala  Met  Lys  Leu  Ser  Pro  Gly  Gln  Ser  Ile  Gly  Ile  Pro
               565                      570                      575

Ile  Thr  Asn  Val  Thr  Ser  Gly  Glu  Tyr  Gln  Ile  Arg  Cys  Arg  Tyr  Ala
               580                      585                 590

Ser  Asn  Asp  Asn  Thr  Asn  Val  Phe  Phe  Asn  Val  Asp  Thr  Gly  Gly  Ala
          595                      600                      605

Asn  Pro  Ile  Phe  Gln  Gln  Ile  Asn  Phe  Ala  Ser  Thr  Val  Asp  Asn  Asn
     610                      615                      620

Thr  Gly  Val  Gln  Gly  Ala  Asn  Gly  Val  Tyr  Val  Val  Lys  Ser  Ile  Ala
625                      630                      635                      640

Thr  Thr  Asp  Asn  Ser  Phe  Thr  Val  Lys  Ile  Pro  Ala  Lys  Thr  Ile  Asn
                    645                      650                      655

Val  His  Leu  Thr  Asn  Gln  Gly  Ser  Ser  Asp  Val  Phe  Leu  Asp  Arg  Ile
               660                      665                      670

Glu  Phe  Val  Pro  Ile  Leu  Glu  Ser  Asn  Thr  Val  Thr  Ile  Phe  Asn  Asn
          675                      680                      685

Ser  Tyr  Thr  Thr  Gly  Ser  Ala  Asn  Leu  Ile  Pro  Ala  Ile  Ala  Pro  Leu
     690                      695                      700

Trp  Ser  Thr  Ser  Ser  Asp  Lys  Ala  Leu  Thr  Gly  Ser  Met  Ser  Ile  Thr
705                      710                      715                      720

Gly  Arg  Thr  Thr  Pro  Asn  Ser  Asp  Asp  Ala  Leu  Leu  Arg  Phe  Phe  Lys
                    725                      730                      735

Thr  Asn  Tyr  Asp  Thr  Gln  Thr  Ile  Pro  Ile  Pro  Gly  Ser  Gly  Lys  Asp
               740                      745                      750

Phe  Thr  Asn  Thr  Leu  Glu  Ile  Gln  Asp  Ile  Val  Ser  Ile  Asp  Ile  Phe
          755                      760                      765

Val  Gly  Ser  Gly  Leu  His  Gly  Ser  Asp  Gly  Ser  Ile  Lys  Leu  Asp  Phe
     770                      775                      780

Thr  Asn  Asn  Asn  Ser  Gly  Ser  Gly  Gly  Ser  Pro  Lys  Ser  Phe  Thr  Glu
785                      790                      795                      800

Gln  Asn  Asp  Leu  Glu  Asn  Ile  Thr  Thr  Gln  Val  Asn  Ala  Leu  Phe  Thr
               805                      810                      815

Ser  Asn  Thr  Gln  Asp  Ala  Leu  Ala  Thr  Asp  Val  Ser  Asp  His  Asp  Ile
          820                      825                      830

Glu  Glu  Val  Val  Leu  Lys  Val  Asp  Ala  Leu  Ser  Asp  Glu  Val  Phe  Gly
          835                      840                      845
```

```
Lys Glu Lys Lys Thr Leu Arg Lys Phe Val Asn Gln Ala Lys Arg Leu
    850             855             860
Ser Lys Ala Arg Asn Leu Val Gly Gly Asn Phe Asp Asn Leu Asp
865         870             875                     880
Ala Trp Tyr Arg Gly Arg Asn Val Val Asn Val Ser Asn His Glu Leu
            885             890                 895
Leu Lys Ser Asp His Val Leu Leu Pro Pro Gly Leu Ser Pro Ser
            900             905             910
Tyr Ile Phe Gln Lys Val Glu Glu Ser Lys Leu Lys Arg Asn Thr Arg
        915             920             925
Tyr Thr Val Ser Gly Phe Ile Ala His Ala Thr Asp Leu Glu Ile Val
    930             935                 940
Val Ser Arg Tyr Gly Gln Glu Ile Lys Lys Val Gln Val Pro Tyr
945             950             955                     960
Gly Glu Ala Phe Pro Leu Thr Ser Ser Gly Pro Val Cys Cys Ile Pro
            965             970                 975
His Ser Thr Ser Asn Gly Thr Leu Gly Asn Pro His Phe Phe Ser Tyr
            980             985                 990
Ser Ile Asp Val Gly Ala Leu Asp Val Asp Thr Asn Pro Gly Ile Glu
        995             1000            1005
Phe Gly Leu Arg Ile Val Asn Pro Thr Gly Met Ala Arg Val Ser Asn
1010                1015                1020
Leu Glu Ile Arg Glu Asp Arg Pro Leu Ala Ala Asn Glu Ile Arg Gln
1025                1030                1035                1040
Val Gln Arg Val Ala Arg Asn Trp Arg Thr Glu Tyr Glu Lys Glu Arg
                1045                1050                1055
Ala Glu Val Thr Ser Leu Ile Gln Pro Val Ile Asn Arg Ile Asn Gly
            1060                1065                1070
Leu Tyr Asp Asn Gly Asn Trp Asn Gly Ser Ile Arg Ser Asp Ile Ser
        1075                1080                1085
Tyr Gln Asn Ile Asp Ala Ile Val Leu Pro Thr Leu Pro Lys Leu Arg
        1090                1095                1100
His Trp Phe Met Ser Asp Arg Phe Ser Glu Gln Gly Asp Ile Met Ala
1105                1110                1115                1120
Lys Phe Gln Gly Ala Leu Asn Arg Ala Tyr Ala Gln Leu Glu Gln Asn
                1125                1130                1135
Thr Leu Leu His Asn Gly His Phe Thr Lys Asp Ala Ala Asn Trp Thr
            1140                1145                1150
Val Glu Gly Asp Ala His Gln Val Val Leu Glu Asp Gly Lys Arg Val
            1155                1160                1165
Leu Arg Leu Pro Asp Trp Ser Ser Ser Val Ser Gln Thr Ile Glu Ile
    1170                1175                1180
Glu Asn Phe Asp Pro Asp Lys Glu Tyr Gln Leu Val Phe His Gly Gln
1185                1190                1195                1200
Gly Glu Gly Thr Val Thr Leu Glu His Gly Glu Glu Thr Lys Tyr Ile
            1205                1210                1215
Glu Thr His Thr His His Phe Ala Asn Phe Thr Ser Gln Arg Gln
        1220                1225                1230
Gly Leu Thr Phe Glu Ser Asn Lys Val Thr Val Thr Ile Ser Ser Glu
        1235                1240                1245
Asp Gly Glu Phe Leu Val Asp Asn Ile Ala Leu Val Glu Ala Pro Leu
        1250                1255                1260
Pro Thr Asp Asp Gln Asn Ser Glu Gly Asn Thr Ala Ser Ser Thr Asn
```

```
                              1265              1270              1275              1280
                   Ser  Asp  Thr  Ser  Met  Asn  Asn  Asn  Gln
                                            1285
```

( 2 ) INFORMATION FOR SEQ ID NO:5:

( i ) SEQUENCE CHARACTERISTICS:
        ( A ) LENGTH: 3771 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( C ) INDIVIDUAL ISOLATE: 33F2

( v i i ) IMMEDIATE SOURCE:
        ( B ) CLONE: E. coli NM522(pMYC2316) B- 18785

( i x ) FEATURE:
( A ) NAME/KEY: misc_feature
( B ) LOCATION: 4..24
( D ) OTHER INFORMATION: /function="oligonucleotide hybridization probe"
/ product="GCA/T ACA/T TTA AAT GAA GTA/T TAT"
/ standard_name="probe a"
/ note="Probe A"

( i x ) FEATURE:
( A ) NAME/KEY: misc_feature
( B ) LOCATION: 13..33
( D ) OTHER INFORMATION: /function="oligonucleotide hybridization probe"
/ product="AAT GAA GTA/T TAT CCA/T GTA/T AAT"
/ standard_name="Probe B"
/ label=probe-b
/ note="probe b"

( x i ) SEQUENCE DESCRIPTION: SEQ ID NO:5:

ATGGCTACAC TTAATGAAGT ATATCCTGTG AATTATAATG TATTATCTTC TGATGCTTTT 60
CAACAATTAG ATACAACAGG TTTTAAAAGT AAATATGATG AAATGATAAA AGCATTCGAA 120
AAAAAATGGA AAAAAGGGGC AAAAGGAAAA GACCTTTTAG ATGTTGCATG GACTTATATA 180
ACTACAGGAG AAATTGACCC TTTAAATGTA ATTAAAGGTG TTTTATCTGTATTAACTTTA 240
ATTCCTGAAG TTGGTACTGT GGCCTCTGCA GCAAGTACTA TTGTAAGTTT TATTTGGCCT 300
AAAATATTTG GAGATAAACC AAATGCAAAA AATATATTTG AAGAGCTCAA GCCTCAAATT 360
GAAGCATTAA TTCAACAAGA TATAACAAAC TATCAAGATG CAATTAATCA AAAAAAATTT 420
GACAGTCTTC AGAAAACAAT TAATCTATAT ACAGTAGCTA TAGATAACAA TGATTACGTA 480
ACAGCAAAAA CGCAACTCGA AAATCTAAAT TCTATACTTA CCTCAGATAT CTCCATATTT 540
ATTCCAGAAG GATATGAAAC TGGAGGTTTA CCTTATTATG CTATGGTTGC TAATGCTCAT 600
ATATTATTGT TAAGAGACGC TATAGTTAAT GCAGAGAAAT TAGGCTTTAG TGATAAAGAA 660
GTAGACACAC ATAAAAAATA TATCAAAATG ACAATACACA ATCATACTGA AGCAGTAATA 720
AAAGCATTCT TAAATGGACT TGACAAATTT AAGAGTTTAG ATGTAAATAG CTATAATAAA 780
AAAGCAAATT ATATTAAAGG TATGACAGAA ATGGTTCTTG ATCTAGTTGC TCTATGGCCA 840
ACTTTCGATC CAGATCATTA TCAAAAAGAA GTAGAAATTG AATTTACAAG AACTATTTCT 900
TCTCCAATTT ACCAACCTGT ACCTAAAAAC ATGCAAAATA CCTCTAGCTC TATTGTACCT 960

-continued

| | | | | | |
|---|---|---|---|---|---|
| AGCGATCTAT | TTCACTATCA | AGGAGATCTT | GTAAAATTAG | AATTTTCTAC | AAGAACGGAC | 1020 |
| AACGATGGTC | TTGCAAAAAT | TTTTACTGGT | ATTCGAAACA | CATTCTACAA | ATCGCCTAAT | 1080 |
| ACTCATGAAA | CATACCATGT | AGATTTTAGT | TATAATACCC | AATCTAGTGG | TAATATTTCA | 1140 |
| AGAGGCTCTT | CAAATCCGAT | TCCAATTGAT | CTTAATAATC | CCATTATTTC | AACTTGTATT | 1200 |
| AGAAATTCAT | TTTATAAGGC | AATAGCGGGA | TCTTCTGTTT | TAGTTAATTT | TAAAGATGGC | 1260 |
| ACTCAAGGGT | ATGCATTTGC | CCAAGCACCA | ACAGGAGGTG | CCTGGGACCA | TTCTTTTATT | 1320 |
| GAATCTGATG | GTGCCCCAGA | AGGGCATAAA | TTAAACTATA | TTTATACTTC | TCCAGGTGAT | 1380 |
| ACATTAAGAG | ATTTCATCAA | TGTATATACT | CTTATAAGTA | CTCCAACTAT | AAATGAACTA | 1440 |
| TCAACAGAAA | AAATCAAAGG | CTTTCCTGCG | GAAAAGGAT | ATATCAAAAA | TCAAGGGATC | 1500 |
| ATGAAATATT | ACGGTAAACC | AGAATATATT | AATGGAGCTC | AACCAGTTAA | TCTGGAAAAC | 1560 |
| CAGCAAACAT | TAATATTCGA | ATTTCATGCT | TCAAAACAG | CTCAATATAC | CATTCGTATA | 1620 |
| CGTTATGCCA | GTACCCAAGG | AACAAAAGGT | TATTTTCGTT | TAGATAATCA | GGAACTGCAA | 1680 |
| ACGCTTAATA | TACCTACTTC | ACACAACGGT | TATGTAACCG | GTAATATTGG | TGAAAATTAT | 1740 |
| GATTTATATA | CAATAGGTTC | ATATACAATT | ACAGAAGGTA | ACCATACTCT | TCAAATCCAA | 1800 |
| CATAATGATA | AAAATGGAAT | GGTTTTAGAT | CGTATTGAAT | TTGTTCCTAA | AGATTCACTT | 1860 |
| CAAGATTCAC | CTCAAGATTC | ACCTCCAGAA | GTTCACGAAT | CAACAATTAT | TTTTGATAAA | 1920 |
| TCATCTCCAA | CTATATGGTC | TTCTAACAAA | CACTCATATA | GCCATATACA | TTTAGAAGGA | 1980 |
| TCATATACAA | GTCAGGGAAG | TTATCCACAC | AATTTATTAA | TTAATTTATT | TCATCCTACA | 2040 |
| GACCCTAACA | GAAATCATAC | TATTCATGTT | AACAATGGTG | ATATGAATGT | TGATTATGGA | 2100 |
| AAAGATTCTG | TAGCCGATGG | GTTAAATTTT | AATAAAATAA | CTGCTACGAT | ACCAAGTGAT | 2160 |
| GCTTGGTATA | GCGGTACTAT | TACTTCTATG | CACTTATTTA | ATGATAATAA | TTTTAAAACA | 2220 |
| ATAACTCCTA | AATTTGAACT | TTCTAATGAA | TTAGAAAACA | TCACAACTCA | AGTAAATGCT | 2280 |
| TTATTCGCAT | CTAGTGCACA | AGATACTCTC | GCAAGTAATG | TAAGTGATTA | CTGGATTGAA | 2340 |
| CAGGTCGTTA | TGAAAGTCGA | TGCCTTATCA | GATGAAGTAT | TGGAAAAGA | GAAAAAAGCA | 2400 |
| TTACGTAAAT | TGGTAAATCA | AGCAAAACGT | CTCAGTAAAA | TACGAAATCT | TCTCATAGGT | 2460 |
| GGTAATTTTG | ACAATTTAGT | CGCTTGGTAT | ATGGGAAAAG | ATGTAGTAAA | AGAATCGGAT | 2520 |
| CATGAATTAT | TTAAAAGTGA | TCATGTCTTA | CTACCTCCCC | CAACATTCCA | TCCTTCTTAT | 2580 |
| ATTTTCCAAA | AGGTGGAAGA | ATCAAAACTA | AAACCAAATA | CACGTTATAC | TATTTCTGGT | 2640 |
| TTTATCGCAC | ATGGAGAAGA | TGTAGAGCTT | GTTGTCTCTC | GTTATGGGCA | AGAAATACAA | 2700 |
| AAAGTGATGC | AAGTGCCATA | TGAAGAAGCA | CTTCCTCTTA | CATCTGAATC | TAATTCTAGT | 2760 |
| TGTTGTGTTC | CAAATTTAAA | TATAAATGAA | ACACTAGCTG | ATCCACATTT | CTTTAGTTAT | 2820 |
| AGCATCGATG | TTGGTTCTCT | GGAAATGGAA | GCGAATCCTG | GTATTGAATT | TGGTCTCCGT | 2880 |
| ATTGTCAAAC | CAACAGGTAT | GGCACGTGTA | AGTAATTTAG | AAATTCGAGA | AGACCGTCCA | 2940 |
| TTAACAGCAA | AAGAAATTCG | TCAAGTACAA | CGTGCAGCAA | GAGATTGGAA | ACAAAACTAT | 3000 |
| GAACAAGAAC | GAACAGAGAT | CACAGCTATA | ATTCAACCTG | TTCTTAATCA | AATTAATGCG | 3060 |
| TTATACGAAA | ATGAAGATTG | GAATGGTTCT | ATTCGTTCAA | ATGTTTCCTA | TCATGATCTA | 3120 |
| GAGCAAATTA | TGCTTCCTAC | TTTATTAAAA | ACTGAGGAAA | TAAATTGTAA | TTATGATCAT | 3180 |
| CCAGCTTTTT | TATTAAAAGT | ATATCATTGG | TTTATGACAG | ATCGTATAGG | AGAACATGGT | 3240 |
| ACTATTTTAG | CACGTTCCA | AGAAGCATTA | GATCGTGCAT | ATACACAATT | AGAAAGTCGT | 3300 |
| AATCTCCTGC | ATAACGGTCA | TTTTACAACT | GATACAGCGA | ATTGGACAAT | AGAAGGAGAT | 3360 |

-continued

| | | | | | | |
|---|---|---|---|---|---|---|
| GCCCATCATA | CAATCTTAGA | AGATGGTAGA | CGTGTGTTAC | GTTTACCAGA | TTGGTCTTCT | 3420 |
| AATGCAACTC | AAACAATTGA | AATTGAAGAT | TTTGACTTAG | ATCAAGAATA | CCAATTGCTC | 3480 |
| ATTCATGCAA | AAGGAAAAGG | TTCCATTACT | TTACAACATG | GAGAAGAAAA | CGAATATGTG | 3540 |
| GAAACACATA | CTCATCATAC | AAATGATTTT | ATAACATCCC | AAAATATTCC | TTTCACTTTT | 3600 |
| AAAGGAAATC | AAATTGAAGT | CCATATTACT | TCAGAAGATG | GAGAGTTTTT | AATCGATCAC | 3660 |
| ATTACAGTAA | TAGAAGTTTC | TAAAACAGAC | ACAAATACAA | ATATTATTGA | AAATTCACCA | 3720 |
| ATCAATACAA | GTATGAATAG | TAATGTAAGA | GTAGATATAC | CAAGAAGTCT | C | 3771 |

( 2 ) INFORMATION FOR SEQ ID NO:6:

( i ) SEQUENCE CHARACTERISTICS:
( A ) LENGTH: 1257 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( C ) INDIVIDUAL ISOLATE: PS33F2

( v i i ) IMMEDIATE SOURCE:
( B ) CLONE: E. coli NM522(pMYC2316) B- 18785

( i x ) FEATURE:
( A ) NAME/KEY: Protein
( B ) LOCATION: 1..1257

( x i ) SEQUENCE DESCRIPTION: SEQ ID NO:6:

Met Ala Thr Leu Asn Glu Val Tyr Pro Val Asn Tyr Asn Val Leu Ser
1 5 10 15

Ser Asp Ala Phe Gln Gln Leu Asp Thr Thr Gly Phe Lys Ser Lys Tyr
20 25 30

Asp Glu Met Ile Lys Ala Phe Glu Lys Lys Trp Lys Lys Gly Ala Lys
35 40 45

Gly Lys Asp Leu Leu Asp Val Ala Trp Thr Tyr Ile Thr Thr Gly Glu
50 55 60

Ile Asp Pro Leu Asn Val Ile Lys Gly Val Leu Ser Val Leu Thr Leu
65 70 75 80

Ile Pro Glu Val Gly Thr Val Ala Ser Ala Ala Ser Thr Ile Val Ser
85 90 95

Phe Ile Trp Pro Lys Ile Phe Gly Asp Lys Pro Asn Ala Lys Asn Ile
100 105 110

Phe Glu Glu Leu Lys Pro Gln Ile Glu Ala Leu Ile Gln Gln Asp Ile
115 120 125

Thr Asn Tyr Gln Asp Ala Ile Asn Gln Lys Lys Phe Asp Ser Leu Gln
130 135 140

Lys Thr Ile Asn Leu Tyr Thr Val Ala Ile Asp Asn Asn Asp Tyr Val
145 150 155 160

Thr Ala Lys Thr Gln Leu Glu Asn Leu Asn Ser Ile Leu Thr Ser Asp
165 170 175

Ile Ser Ile Phe Ile Pro Glu Gly Tyr Glu Thr Gly Gly Leu Pro Tyr
180 185 190

Tyr Ala Met Val Ala Asn Ala His Ile Leu Leu Leu Arg Asp Ala Ile
195 200 205

```
Val  Asn  Ala  Glu  Lys  Leu  Gly  Phe  Ser  Asp  Lys  Glu  Val  Asp  Thr  His
     210                213                     220

Lys  Lys  Tyr  Ile  Lys  Met  Thr  Ile  His  Asn  His  Thr  Glu  Ala  Val  Ile
225                     230                     235                          240

Lys  Ala  Phe  Leu  Asn  Gly  Leu  Asp  Lys  Phe  Lys  Ser  Leu  Asp  Val  Asn
                245                     250                          255

Ser  Tyr  Asn  Lys  Lys  Ala  Asn  Tyr  Ile  Lys  Gly  Met  Thr  Glu  Met  Val
                260                265                     270

Leu  Asp  Leu  Val  Ala  Leu  Trp  Pro  Thr  Phe  Asp  Pro  His  Tyr  Gln
          275                     280                     285

Lys  Glu  Val  Glu  Ile  Glu  Phe  Thr  Arg  Thr  Ile  Ser  Ser  Pro  Ile  Tyr
     290                     295                     300

Gln  Pro  Val  Pro  Lys  Asn  Met  Gln  Asn  Thr  Ser  Ser  Ser  Ile  Val  Pro
305                     310                     315                          320

Ser  Asp  Leu  Phe  His  Tyr  Gln  Gly  Asp  Leu  Val  Lys  Leu  Glu  Phe  Ser
                     325                     330                          335

Thr  Arg  Thr  Asp  Asn  Asp  Gly  Leu  Ala  Lys  Ile  Phe  Thr  Gly  Ile  Arg
                340                     345                     350

Asn  Thr  Phe  Tyr  Lys  Ser  Pro  Asn  Thr  His  Glu  Thr  Tyr  His  Val  Asp
          355                     360                     365

Phe  Ser  Tyr  Asn  Thr  Gln  Ser  Ser  Gly  Asn  Ile  Ser  Arg  Gly  Ser  Ser
     370                     375                     380

Asn  Pro  Ile  Pro  Ile  Asp  Leu  Asn  Asn  Pro  Ile  Ile  Ser  Thr  Cys  Ile
385                     390                     395                          400

Arg  Asn  Ser  Phe  Tyr  Lys  Ala  Ile  Ala  Gly  Ser  Ser  Val  Leu  Val  Asn
                405                     410                          415

Phe  Lys  Asp  Gly  Thr  Gln  Gly  Tyr  Ala  Phe  Ala  Gln  Ala  Pro  Thr  Gly
                420                     425                     430

Gly  Ala  Trp  Asp  His  Ser  Phe  Ile  Glu  Ser  Asp  Gly  Ala  Pro  Glu  Gly
          435                     440                     445

His  Lys  Leu  Asn  Tyr  Ile  Tyr  Thr  Ser  Pro  Gly  Asp  Thr  Leu  Arg  Asp
     450                     455                     460

Phe  Ile  Asn  Val  Tyr  Thr  Leu  Ile  Ser  Thr  Pro  Thr  Ile  Asn  Glu  Leu
465                     470                     475                          480

Ser  Thr  Glu  Lys  Ile  Lys  Gly  Phe  Pro  Ala  Glu  Lys  Gly  Tyr  Ile  Lys
                     485                     490                          495

Asn  Gln  Gly  Ile  Met  Lys  Tyr  Tyr  Gly  Lys  Pro  Glu  Tyr  Ile  Asn  Gly
               500                     505                     510

Ala  Gln  Pro  Val  Asn  Leu  Glu  Asn  Gln  Thr  Leu  Ile  Phe  Glu  Phe
          515                     520                     525

His  Ala  Ser  Lys  Thr  Ala  Gln  Tyr  Thr  Ile  Arg  Ile  Arg  Tyr  Ala  Ser
     530                     535                     540

Thr  Gln  Gly  Thr  Lys  Gly  Tyr  Phe  Arg  Leu  Asp  Asn  Gln  Glu  Leu  Gln
545                     550                     555                          560

Thr  Leu  Asn  Ile  Pro  Thr  Ser  His  Asn  Gly  Tyr  Val  Thr  Gly  Asn  Ile
                     565                     570                          575

Gly  Glu  Asn  Tyr  Asp  Leu  Tyr  Thr  Ile  Gly  Ser  Tyr  Thr  Ile  Thr  Glu
                580                     585                     590

Gly  Asn  His  Thr  Leu  Gln  Ile  Gln  His  Asn  Asp  Lys  Asn  Gly  Met  Val
          595                     600                     605

Leu  Asp  Arg  Ile  Glu  Phe  Val  Pro  Lys  Asp  Ser  Leu  Gln  Asp  Ser  Pro
610                     615                     620

Gln  Asp  Ser  Pro  Pro  Glu  Val  His  Glu  Ser  Thr  Ile  Ile  Phe  Asp  Lys
```

|  |  |  |  |  |  |  |  |  |  |  |  |  |  |  |
|---|---|---|---|---|---|---|---|---|---|---|---|---|---|---|
| 625 |  |  |  | 630 |  |  |  | 635 |  |  |  |  |  | 640 |
| Ser | Ser | Pro | Thr | Ile | Trp | Ser | Ser | Asn | Lys | His | Ser | Tyr | Ser | His | Ile |
|  |  |  |  | 645 |  |  |  | 650 |  |  |  | 655 |
| His | Leu | Glu | Gly | Ser | Tyr | Thr | Ser | Gln | Gly | Ser | Tyr | Pro | His | Asn | Leu |
|  |  |  | 660 |  |  |  |  | 665 |  |  |  |  | 670 |
| Leu | Ile | Asn | Leu | Phe | His | Pro | Thr | Asp | Pro | Asn | Arg | Asn | His | Thr | Ile |
|  |  | 675 |  |  |  |  | 680 |  |  |  |  | 685 |
| His | Val | Asn | Asn | Gly | Asp | Met | Asn | Val | Asp | Tyr | Gly | Lys | Asp | Ser | Val |
|  | 690 |  |  |  |  | 695 |  |  |  |  | 700 |
| Ala | Asp | Gly | Leu | Asn | Phe | Asn | Lys | Ile | Thr | Ala | Thr | Ile | Pro | Ser | Asp |
| 705 |  |  |  |  | 710 |  |  |  |  | 715 |  |  |  |  | 720 |
| Ala | Trp | Tyr | Ser | Gly | Thr | Ile | Thr | Ser | Met | His | Leu | Phe | Asn | Asp | Asn |
|  |  |  |  | 725 |  |  |  |  | 730 |  |  |  |  | 735 |
| Asn | Phe | Lys | Thr | Ile | Thr | Pro | Lys | Phe | Glu | Leu | Ser | Asn | Glu | Leu | Glu |
|  |  |  | 740 |  |  |  |  | 745 |  |  |  |  | 750 |
| Asn | Ile | Thr | Thr | Gln | Val | Asn | Ala | Leu | Phe | Ala | Ser | Ser | Ala | Gln | Asp |
|  |  | 755 |  |  |  |  | 760 |  |  |  |  | 765 |
| Thr | Leu | Ala | Ser | Asn | Val | Ser | Asp | Tyr | Trp | Ile | Glu | Gln | Val | Val | Met |
|  | 770 |  |  |  |  | 775 |  |  |  |  | 780 |
| Lys | Val | Asp | Ala | Leu | Ser | Asp | Glu | Val | Phe | Gly | Lys | Glu | Lys | Lys | Ala |
| 785 |  |  |  |  | 790 |  |  |  |  | 795 |  |  |  |  | 800 |
| Leu | Arg | Lys | Leu | Val | Asn | Gln | Ala | Lys | Arg | Leu | Ser | Lys | Ile | Arg | Asn |
|  |  |  |  | 805 |  |  |  |  | 810 |  |  |  |  | 815 |
| Leu | Leu | Ile | Gly | Gly | Asn | Phe | Asp | Asn | Leu | Val | Ala | Trp | Tyr | Met | Gly |
|  |  |  | 820 |  |  |  |  | 825 |  |  |  |  | 830 |
| Lys | Asp | Val | Val | Lys | Glu | Ser | Asp | His | Glu | Leu | Phe | Lys | Ser | Asp | His |
|  |  | 835 |  |  |  |  | 840 |  |  |  |  | 845 |
| Val | Leu | Leu | Pro | Pro | Pro | Thr | Phe | His | Pro | Ser | Tyr | Ile | Phe | Gln | Lys |
|  | 850 |  |  |  |  | 855 |  |  |  |  | 860 |
| Val | Glu | Glu | Ser | Lys | Leu | Lys | Pro | Asn | Thr | Arg | Tyr | Thr | Ile | Ser | Gly |
| 865 |  |  |  |  | 870 |  |  |  |  | 875 |  |  |  |  | 880 |
| Phe | Ile | Ala | His | Gly | Glu | Asp | Val | Glu | Leu | Val | Val | Ser | Arg | Tyr | Gly |
|  |  |  |  | 885 |  |  |  |  | 890 |  |  |  |  | 895 |
| Gln | Glu | Ile | Gln | Lys | Val | Met | Gln | Val | Pro | Tyr | Glu | Glu | Ala | Leu | Pro |
|  |  |  | 900 |  |  |  |  | 905 |  |  |  |  | 910 |
| Leu | Thr | Ser | Glu | Ser | Asn | Ser | Ser | Cys | Cys | Val | Pro | Asn | Leu | Asn | Ile |
|  |  | 915 |  |  |  |  | 920 |  |  |  |  | 925 |
| Asn | Glu | Thr | Leu | Ala | Asp | Pro | His | Phe | Phe | Ser | Tyr | Ser | Ile | Asp | Val |
|  | 930 |  |  |  |  | 935 |  |  |  |  | 940 |
| Gly | Ser | Leu | Glu | Met | Glu | Ala | Asn | Pro | Gly | Ile | Glu | Phe | Gly | Leu | Arg |
| 945 |  |  |  |  | 950 |  |  |  |  | 955 |  |  |  |  | 960 |
| Ile | Val | Lys | Pro | Thr | Gly | Met | Ala | Arg | Val | Ser | Asn | Leu | Glu | Ile | Arg |
|  |  |  |  | 965 |  |  |  |  | 970 |  |  |  |  | 975 |
| Glu | Asp | Arg | Pro | Leu | Thr | Ala | Lys | Glu | Ile | Arg | Gln | Val | Gln | Arg | Ala |
|  |  |  | 980 |  |  |  |  | 985 |  |  |  |  | 990 |
| Ala | Arg | Asp | Trp | Lys | Gln | Asn | Tyr | Glu | Gln | Glu | Arg | Thr | Glu | Ile | Thr |
|  |  | 995 |  |  |  |  | 1000 |  |  |  |  | 1005 |
| Ala | Ile | Ile | Gln | Pro | Val | Leu | Asn | Gln | Ile | Asn | Ala | Leu | Tyr | Glu | Asn |
|  |  | 1010 |  |  |  |  | 1015 |  |  |  |  | 1020 |
| Glu | Asp | Trp | Asn | Gly | Ser | Ile | Arg | Ser | Asn | Val | Ser | Tyr | His | Asp | Leu |
| 1025 |  |  |  |  | 1030 |  |  |  |  | 1035 |  |  |  |  | 1040 |
| Glu | Gln | Ile | Met | Leu | Pro | Thr | Leu | Leu | Lys | Thr | Glu | Glu | Ile | Asn | Cys |
|  |  |  |  | 1045 |  |  |  |  | 1050 |  |  |  |  | 1055 |

```
              Asn    Tyr    Asp    His    Pro    Ala    Phe    Leu    Leu    Lys    Val    Tyr    His    Trp    Phe    Met
                                   1060                              1065                             1070

Thr    Asp    Arg    Ile    Gly    Glu    His    Gly    Thr    Ile    Leu    Ala    Arg    Phe    Gln    Glu
                                   1075                              1080                             1085

Ala    Leu    Asp    Arg    Ala    Tyr    Thr    Gln    Leu    Glu    Ser    Arg    Asn    Leu    Leu    His
                                   1090                              1095                             1100

Asn    Gly    His    Phe    Thr    Thr    Asp    Thr    Ala    Asn    Trp    Thr    Ile    Glu    Gly    Asp
              1105                        1110                              1115                                    1120

Ala    His    His    Thr    Ile    Leu    Glu    Asp    Gly    Arg    Arg    Val    Leu    Arg    Leu    Pro
                                   1125                              1130                             1135

Asp    Trp    Ser    Ser    Asn    Ala    Thr    Gln    Thr    Ile    Glu    Ile    Glu    Asp    Phe    Asp
                                   1140                              1145                             1150

Leu    Asp    Gln    Glu    Tyr    Gln    Leu    Leu    Ile    His    Ala    Lys    Gly    Lys    Gly    Ser
                                   1155                              1160                             1165

Ile    Thr    Leu    Gln    His    Gly    Glu    Glu    Asn    Glu    Tyr    Val    Glu    Thr    His    Thr
                                   1170                              1175                             1180

His    His    Thr    Asn    Asp    Phe    Ile    Thr    Ser    Gln    Asn    Ile    Pro    Phe    Thr    Phe
              1185                        1190                              1195                                    1200

Lys    Gly    Asn    Gln    Ile    Glu    Val    His    Ile    Thr    Ser    Glu    Asp    Gly    Glu    Phe
                                   1205                              1210                             1215

Leu    Ile    Asp    His    Ile    Thr    Val    Ile    Glu    Val    Ser    Lys    Thr    Asp    Thr    Asn
                                   1220                              1225                             1230

Thr    Asn    Ile    Ile    Glu    Asn    Ser    Pro    Ile    Asn    Thr    Ser    Met    Asn    Ser    Asn
                                   1235                              1240                             1245

Val    Arg    Val    Asp    Ile    Pro    Arg    Ser    Leu
                                   1250                              1255
```

( 2 ) INFORMATION FOR SEQ ID NO:7:

( i ) SEQUENCE CHARACTERISTICS:
        ( A ) LENGTH: 3738 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( C ) INDIVIDUAL ISOLATE: PS86Q3

( v i i ) IMMEDIATE SOURCE:
( A ) LIBRARY: Lambdagem (TM) - 11 LIBRARY
( B ) CLONE: 86Q3a ( x i ) SEQUENCE DESCRIPTION: SEQ ID NO:7:

ATGGCAACAA TTAATGAGTT GTATCCAGTT CCTTATAATG TGCTAGCTCA TCCAATTAAA 60

GAAGTCGATG ATCCTTATTC TTGGTCAAAT TTATTAAAGG GTATACAAGA AGGTTGGGAA 120

GAATGGGGAA AAACAGGACA AAAAAAACTT TTTGAAGACC ATCTTACGAT TGCATGGAAT 180

CTTTATAAAA CAGGAAAATT AGATTATTTC GCTTTGACAA AAGCATCAAT ATCATTGATT 240

GGATTTATTC CAGGGGCAGA AGCAGCAGTT CCCTTTATTA ATATGTTTGT AGACTTTGTT 300

TGGCCTAAAT TATTTGGTGC GAATACAGAA GGAAAAGATC AACAGTTGTT TAATGCTATC 360

ATGGATGCAG TTAATAAAAT GGTAGATAAT AAGTTCTTAA GTTATAATCT TAGTACACTT 420

AATAAAACAA TTGAAGGACT TCAAGGTAAT TTAGGCCTAT TTCAAAATGC TATACAAGTA 480

```
GCCATTTGTC  AAGGCAGTAC  ACCAGAAAGA  GTAAATTTTG  ATCAAAATTG  TACACCATGT   540
AATCCAAATC  AACCTTGTAA  AGATGATTTG  GATAGAGTTG  CTTCACGTTT  TGATACGGCT   600
AATTCTCAAT  TCACACAGCA  TTTACCAGAA  TTTAAAAATC  CTTGGTCGGA  TGAAAACTCT   660
ACTCAGGAAT  TTAAAAGAAC  ATCTGTTGAA  TTAACTTTAC  CAATGTATAC  AACAGTAGCT   720
ACGTTACATC  TTTTATTATA  TGAAGGATAT  ATAGAATTTA  TGACAAAATG  GAATTTTCAC   780
AATGAACAAT  ATTTAAATAA  TTTAAAGGTA  GAATTACAAC  AATTGATACA  CTCATATTCA   840
GAAACTGTTC  GTACAAGTTT  CCTTCAATTT  TTACCTACCT  TGAATAATCG  TTCAAAATCA   900
TCCGTAAATG  CTTATAACCG  TTATGTCCGC  AATATGACTG  TTAACTGTTT  AGATATTGCT   960
GCTACATGGC  CTACATTTGA  TACACATAAT  TATCATCAAG  GTGGTAAATT  AGATTTAACT  1020
CGTATTATTC  TTTCAGATAC  AGCAGGACCA  ATAGAAGAAT  ATACTACTGG  CGACAAAACT  1080
TCAGGACCTG  AACATAGTAA  CATTACACCA  ATAATATTC   TAGATACACC  ATCTCCAACA  1140
TATCAGCACT  CATTTGTATC  TGTTGATTCT  ATTGTATATT  CTAGAAAAGA  ATTACAACAA  1200
TTAGACATAG  CTACTTATAG  TACAAATAAT  AGTAATAATT  GTCACCCTTA  TGGATTACGA  1260
CTTTCATATA  CAGATGGAAG  CAGATATGAT  TATGGAGATA  ATCAACCTGA  TTTTACTACT  1320
TCCAATAACA  ATTATTGTCA  TAATAGCTAT  ACTGCCCCTA  TTACACTTGT  GAATGCACGA  1380
CATTTATATA  ATGCAAAAGG  CTCTTTACAA  AATGTAGAAT  CTTTAGTGGT  TAGTACTGTA  1440
AATGGTGGAA  GTGGTTCATG  CATTTGTGAT  GCATGGATTA  ATTATTTACG  TCCTCCTCAA  1500
ACAAGTAAAA  ATGAATCACG  TCCTGATCAA  AAAATTAATG  TTTTGTATCC  AATAACAGAA  1560
ACTGTAAATA  AGGGGACTGG  AGGAAATTTA  GGAGTTATTT  CTGCCTATGT  TCCAATGGAA  1620
CTTGTACCAG  AAAACGTTAT  TGGAGATGTT  AATGCTGATA  CTAAATTGCC  ACTTACACAA  1680
TTAAAGGGCT  TTCCATTTGA  AAAATATGGT  TCTGAGTATA  ATAATCGGGG  TATCTCTCTT  1740
GTTCGCGAAT  GGATAAATGG  TAACAATGCA  GTTAAACTTT  CTAATAGTCA  ATCTGTTGGC  1800
ATACAAATTA  CGAATCAAAC  CAAACAAAAA  TATGAAATAC  GTTGCCGTTA  TGCGAGTAAA  1860
GGAGATAATA  ATGTTTATTT  TAATGTGGAT  TTAAGTGAAA  ATCCATTTAG  AAATTCCATT  1920
TCTTTTGGAT  CTACTGAAAG  TTCTGTTGTA  GGAGTACAAG  GTGAAAATGG  AAAGTATATA  1980
TTGAAATCAA  TCACAACGGT  AGAAATACCT  GCTGGAAGTT  CTATGTTCA   TATAACAAAC  2040
CAAGGTTCTT  CAGATCTCTT  TTTAGATCGT  ATTGAGTTTG  TTCCAAAAAT  CCAATTCCAA  2100
TTCTGTGATA  ATAATAATCT  TCACTGTGAT  TGTAATAACC  CTGTTGACAC  CGATTGTACA  2160
TTTTGTTGCG  TTTGCACTAG  TCTTACTGAT  TGTGATTGTA  ATAACCCTCG  TGGCCTAGAT  2220
TGTACGCTAT  GTTGTCAGGT  AGAAAATCAG  CTACCTTCTT  TTGTGACACT  TACAGATTTA  2280
CAAAATATTA  CGACACAAGT  AAATGCATTA  GTTGCATCGA  GCGAACATGA  TACACTTGCA  2340
ACAGACGTGA  GTGATTATGA  GATTGAAGAA  GTTGTACTGA  AAGTAGATGC  ATTATCTGGT  2400
GAAGTGTTTG  GAAAAGAGAA  AAAAGCATTG  CGTAAATTGG  TAAATCACAC  AAAACGTTTA  2460
AGCAAAGCGC  GTAACCTCTT  GATAGGAGGA  AATTTTGATA  ACTTGGATGC  TTGGTACAGA  2520
GGCCGAAATG  TAGTAAACGT  ATCTGATCAT  GAACTATTTA  AGAGTGATCA  TGTATTATTG  2580
CCACCACCAA  CACTGTACTC  ATCTTATATG  TTCCAAAAAG  TAGAGGAATC  GAAATTAAAA  2640
GCGAATACAC  GTTATACTGT  GTCTGGTTTT  ATTGCACATG  CAGAAGATTT  AGAAATTGTT  2700
GTGTCTCGTT  ATGGGCAAGA  AGTGAAGAAA  GTGGTTCAAG  TTCCATATGG  AGAAGCATTC  2760
CCATTGACAT  CGAGGGGAGC  GATTTGTTGC  CCTCCACGTT  CTACAAGTAA  TGGAAAACCT  2820
GCTGATCCAC  ATTTCTTTAG  TTACAGTATT  GATGTGGGAA  CATTAGATGT  AGAAGCAAAC  2880
```

| | | | | |
|---|---|---|---|---|
| CCTGGTATCG | AATTGGGTCT | TCGTATTGTA | GAACGAACTG | GAATGGCACG | TGTAAGTAAT | 2940 |
| TTAGAAATTC | GTGAAGATCG | TCCATTAAAG | AAAAATGAAC | TCCGCAATGT | ACAACGTGCA | 3000 |
| GCAAGAAATT | GGAGAACAGC | ATATGACCAA | GAACGTGCAG | AAGTAACGGC | CTTGATTCAA | 3060 |
| CCTGTATTAA | ATCAAATCAA | TGCGTTGTAT | GAAATGAAG | ATTGGAATGG | AGCAATTCGT | 3120 |
| TCTGGAGTTT | CTTATCATGA | CTTAGAAGCA | ATTGTTTTAC | CAACATTACC | AAAATTAAAT | 3180 |
| CATTGGTTTA | TGTCTGATAT | GTTAGGGGAA | CAAGGTTCCA | TTTTAGCTCA | ATTTCAAGAA | 3240 |
| GCATTAGATC | GTGCGTATAC | GCAACTCGAA | GAAAGTACAA | TTCTGCATAA | TGGTCATTTC | 3300 |
| ACAACAGATG | CAGCAAATTG | GACGATAGAA | GGCGATGCAC | ATCATGCGAT | ATTAGAAGAT | 3360 |
| GGTAGACGCG | TATTACGTCT | TCCAGATTGG | TCTTCTAGCG | TTTCACAAAC | CATTGAAATA | 3420 |
| GAAAATTTTG | ATCCAGATAA | AGAATATCAG | TTAGTTTTCC | ATGCACAAGG | AGAAGGAACG | 3480 |
| GTCTCCCTTC | AACATGGTGA | AGAAGGAGAA | TATGTGGAAA | CACACCCGCA | TAAGTCTGCG | 3540 |
| AATTTTACAA | CTTCACACCG | TCAAGGAGTC | ACATTGAAA | CAAATAAAGT | AACAGTTGAA | 3600 |
| ATTACCTCAG | AAGATGGAGA | ATTCCTAGTC | GATCATATTG | CTCTTGTGGA | AGCTCCTCTT | 3660 |
| CCTACAGATG | ACCAAAGTTC | AGATGGAAAT | ACGACTTCCA | ATACGAATAG | CAATACAAGT | 3720 |
| ATGAATAATA | ATCAATAA | | | | | 3738 |

( 2 ) INFORMATION FOR SEQ ID NO:8:

( i ) SEQUENCE CHARACTERISTICS:
        ( A ) LENGTH: 1245 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v ) ORIGINAL SOURCE:
        ( A ) ORGANISM: BACILLUS THURINGIENSIS
        ( C ) INDIVIDUAL ISOLATE: PS86Q3

( v i i ) IMMEDIATE SOURCE:
( A ) LIBRARY: LAMBDAGEM (tm) - 11 library
( B ) CLONE: 86Q3A ( x i ) SEQUENCE DESCRIPTION: SEQ ID NO:8:

```
Met Ala Thr Ile Asn Glu Leu Tyr Pro Val Pro Tyr Asn Val Leu Ala
1               5                   10                  15

His Pro Ile Lys Glu Val Asp Asp Pro Tyr Ser Trp Ser Asn Leu Leu
            20                  25                  30

Lys Gly Ile Gln Glu Gly Trp Glu Glu Trp Gly Lys Thr Gly Gln Lys
        35                  40                  45

Lys Leu Phe Glu Asp His Leu Thr Ile Ala Trp Asn Leu Tyr Lys Thr
    50                  55                  60

Gly Lys Leu Asp Tyr Phe Ala Leu Thr Lys Ala Ser Ile Ser Leu Ile
65                  70                  75                  80

Gly Phe Ile Pro Gly Ala Glu Ala Ala Val Pro Phe Ile Asn Met Phe
                85                  90                  95

Val Asp Phe Val Trp Pro Lys Leu Phe Gly Ala Asn Thr Glu Gly Lys
            100                 105                 110

Asp Gln Gln Leu Phe Asn Ala Ile Met Asp Ala Val Asn Lys Met Val
        115                 120                 125

Asp Asn Lys Phe Leu Ser Tyr Asn Leu Ser Thr Leu Asn Lys Thr Ile
```

```
         130                    135                    140
Glu  Gly  Leu  Gln  Gly  Asn  Leu  Gly  Leu  Phe  Gln  Asn  Ala  Ile  Gln  Val
145                      150                    155                      160

Ala  Ile  Cys  Gln  Gly  Ser  Thr  Pro  Glu  Arg  Val  Asn  Phe  Asp  Gln  Asn
                    165                    170                         175

Cys  Thr  Pro  Cys  Asn  Pro  Asn  Gln  Pro  Cys  Lys  Asp  Asp  Leu  Asp  Arg
                180                         185                    190

Val  Ala  Ser  Arg  Phe  Asp  Thr  Ala  Asn  Ser  Gln  Phe  Thr  Gln  His  Leu
          195                         200                    205

Pro  Glu  Phe  Lys  Asn  Pro  Trp  Ser  Asp  Glu  Asn  Ser  Thr  Gln  Glu  Phe
     210                         215                         220

Lys  Arg  Thr  Ser  Val  Glu  Leu  Thr  Leu  Pro  Met  Tyr  Thr  Thr  Val  Ala
225                      230                    235                      240

Thr  Leu  His  Leu  Leu  Leu  Tyr  Glu  Gly  Tyr  Ile  Glu  Phe  Met  Thr  Lys
                         245                    250                    255

Trp  Asn  Phe  His  Asn  Glu  Gln  Tyr  Leu  Asn  Asn  Leu  Lys  Val  Glu  Leu
               260                    265                    270

Gln  Gln  Leu  Ile  His  Ser  Tyr  Ser  Glu  Thr  Val  Arg  Thr  Ser  Phe  Leu
          275                    280                    285

Gln  Phe  Leu  Pro  Thr  Leu  Asn  Asn  Arg  Ser  Lys  Ser  Ser  Val  Asn  Ala
     290                    295                    300

Tyr  Asn  Arg  Tyr  Val  Arg  Asn  Met  Thr  Val  Asn  Cys  Leu  Asp  Ile  Ala
305                      310                    315                      320

Ala  Thr  Trp  Pro  Thr  Phe  Asp  Thr  His  Asn  Tyr  His  Gln  Gly  Gly  Lys
                    325                    330                         335

Leu  Asp  Leu  Thr  Arg  Ile  Ile  Leu  Ser  Asp  Thr  Ala  Gly  Pro  Ile  Glu
                340                    345                    350

Glu  Tyr  Thr  Thr  Gly  Asp  Lys  Thr  Ser  Gly  Pro  Glu  His  Ser  Asn  Ile
          355                    360                    365

Thr  Pro  Asn  Asn  Ile  Leu  Asp  Thr  Pro  Ser  Pro  Thr  Tyr  Gln  His  Ser
     370                    375                    380

Phe  Val  Ser  Val  Asp  Ser  Ile  Val  Tyr  Ser  Arg  Lys  Glu  Leu  Gln  Gln
385                      390                    395                      400

Leu  Asp  Ile  Ala  Thr  Tyr  Ser  Thr  Asn  Asn  Ser  Asn  Asn  Cys  His  Pro
                    405                    410                         415

Tyr  Gly  Leu  Arg  Leu  Ser  Tyr  Thr  Asp  Gly  Ser  Arg  Tyr  Asp  Tyr  Gly
                420                    425                    430

Asp  Asn  Gln  Pro  Asp  Phe  Thr  Thr  Ser  Asn  Asn  Tyr  Cys  His  Asn
          435                    440                    445

Ser  Tyr  Thr  Ala  Pro  Ile  Thr  Leu  Val  Asn  Ala  Arg  His  Leu  Tyr  Asn
     450                    455                    460

Ala  Lys  Gly  Ser  Leu  Gln  Asn  Val  Glu  Ser  Leu  Val  Val  Ser  Thr  Val
465                      470                    475                      480

Asn  Gly  Gly  Ser  Gly  Ser  Cys  Ile  Cys  Asp  Ala  Trp  Ile  Asn  Tyr  Leu
                    485                    490                         495

Arg  Pro  Pro  Gln  Thr  Ser  Lys  Asn  Glu  Ser  Arg  Pro  Asp  Gln  Lys  Ile
                500                         505                    510

Asn  Val  Leu  Tyr  Pro  Ile  Thr  Glu  Thr  Val  Asn  Lys  Gly  Thr  Gly  Gly
          515                    520                    525

Asn  Leu  Gly  Val  Ile  Ser  Ala  Tyr  Val  Pro  Met  Glu  Leu  Val  Pro  Glu
     530                    535                    540

Asn  Val  Ile  Gly  Asp  Val  Asn  Ala  Asp  Thr  Lys  Leu  Pro  Leu  Thr  Gln
545                      550                    555                      560
```

```
Leu Lys Gly Phe Pro Phe Glu Lys Tyr Gly Ser Glu Tyr Asn Asn Arg
            565                 570                 575
Gly Ile Ser Leu Val Arg Glu Trp Ile Asn Gly Asn Asn Ala Val Lys
            580                 585                 590
Leu Ser Asn Ser Gln Ser Val Gly Ile Gln Ile Thr Asn Gln Thr Lys
            595                 600                 605
Gln Lys Tyr Glu Ile Arg Cys Arg Tyr Ala Ser Lys Gly Asp Asn Asn
610                     615                 620
Val Tyr Phe Asn Val Asp Leu Ser Glu Asn Pro Phe Arg Asn Ser Ile
625                 630                 635                 640
Ser Phe Gly Ser Thr Glu Ser Ser Val Val Gly Val Gln Gly Glu Asn
            645                 650                 655
Gly Lys Tyr Ile Leu Lys Ser Ile Thr Thr Val Glu Ile Pro Ala Gly
            660                 665                 670
Ser Phe Tyr Val His Ile Thr Asn Gln Gly Ser Ser Asp Leu Phe Leu
            675                 680                 685
Asp Arg Ile Glu Phe Val Pro Lys Ile Gln Phe Gln Phe Cys Asp Asn
            690                 695                 700
Asn Asn Leu His Cys Asp Cys Asn Asn Pro Val Asp Thr Asp Cys Thr
705                 710                 715                 720
Phe Cys Cys Val Cys Thr Ser Leu Thr Asp Cys Asp Cys Asn Asn Pro
            725                 730                 735
Arg Gly Leu Asp Cys Thr Leu Cys Cys Gln Val Glu Asn Gln Leu Pro
            740                 745                 750
Ser Phe Val Thr Leu Thr Asp Leu Gln Asn Ile Thr Thr Gln Val Asn
            755                 760                 765
Ala Leu Val Ala Ser Ser Glu His Asp Thr Leu Ala Thr Asp Val Ser
770                 775                 780
Asp Tyr Glu Ile Glu Glu Val Val Leu Lys Val Asp Ala Leu Ser Gly
785                 790                 795                 800
Glu Val Phe Gly Lys Glu Lys Lys Ala Leu Arg Lys Leu Val Asn His
            805                 810                 815
Thr Lys Arg Leu Ser Lys Ala Arg Asn Leu Leu Ile Gly Gly Asn Phe
            820                 825                 830
Asp Asn Leu Asp Ala Trp Tyr Arg Gly Arg Asn Val Val Asn Val Ser
            835                 840                 845
Asp His Glu Leu Phe Lys Ser Asp His Val Leu Leu Pro Pro Pro Thr
    850                 855                 860
Leu Tyr Ser Ser Tyr Met Phe Gln Lys Val Glu Glu Ser Lys Leu Lys
865                 870                 875                 880
Ala Asn Thr Arg Tyr Thr Val Ser Gly Phe Ile Ala His Ala Glu Asp
            885                 890                 895
Leu Glu Ile Val Val Ser Arg Tyr Gly Gln Glu Val Lys Lys Val Val
            900                 905                 910
Gln Val Pro Tyr Gly Glu Ala Phe Pro Leu Thr Ser Arg Gly Ala Ile
    915                 920                 925
Cys Cys Pro Pro Arg Ser Thr Ser Asn Gly Lys Pro Ala Asp Pro His
    930                 935                 940
Phe Phe Ser Tyr Ser Ile Asp Val Gly Thr Leu Asp Val Glu Ala Asn
945                 950                 955                 960
Pro Gly Ile Glu Leu Gly Leu Arg Ile Val Glu Arg Thr Gly Met Ala
            965                 970                 975
Arg Val Ser Asn Leu Glu Ile Arg Glu Asp Arg Pro Leu Lys Lys Asn
            980                 985                 990
```

```
Glu Leu Arg Asn Val Gln Arg Ala Ala Arg Asn Trp Arg Thr Ala Tyr
        995                 1000                1005

Asp Gln Glu Arg Ala Glu Val Thr Ala Leu Ile Gln Pro Val Leu Asn
    1010                1015                1020

Gln Ile Asn Ala Leu Tyr Glu Asn Glu Asp Trp Asn Gly Ala Ile Arg
1025                1030                1035                1040

Ser Gly Val Ser Tyr His Asp Leu Glu Ala Ile Val Leu Pro Thr Leu
                1045                1050                1055

Pro Lys Leu Asn His Trp Phe Met Ser Asp Met Leu Gly Glu Gln Gly
            1060                1065                1070

Ser Ile Leu Ala Gln Phe Gln Glu Ala Leu Asp Arg Ala Tyr Thr Gln
        1075                1080                1085

Leu Glu Glu Ser Thr Ile Leu His Asn Gly His Phe Thr Thr Asp Ala
    1090                1095                1100

Ala Asn Trp Thr Ile Glu Gly Asp Ala His His Ala Ile Leu Glu Asp
1105                1110                1115                1120

Gly Arg Arg Val Leu Arg Leu Pro Asp Trp Ser Ser Ser Val Ser Gln
                1125                1130                1135

Thr Ile Glu Ile Glu Asn Phe Asp Pro Asp Lys Glu Tyr Gln Leu Val
            1140                1145                1150

Phe His Ala Gln Gly Glu Gly Thr Val Ser Leu Gln His Gly Glu Glu
        1155                1160                1165

Gly Glu Tyr Val Glu Thr His Pro His Lys Ser Ala Asn Phe Thr Thr
    1170                1175                1180

Ser His Arg Gln Gly Val Thr Phe Glu Thr Asn Lys Val Thr Val Glu
1185                1190                1195                1200

Ile Thr Ser Glu Asp Gly Glu Phe Leu Val Asp His Ile Ala Leu Val
                1205                1210                1215

Glu Ala Pro Leu Pro Thr Asp Asp Gln Ser Ser Asp Gly Asn Thr Thr
            1220                1225                1230

Ser Asn Thr Asn Ser Asn Thr Ser Met Asn Asn Asn Gln
        1235                1240                1245
```

( 2 ) INFORMATION FOR SEQ ID NO:9:

( i ) SEQUENCE CHARACTERISTICS:
( A ) LENGTH: 2412 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Bacillus thuringiensis
( C ) INDIVIDUAL ISOLATE: PS63B ( v i i ) IMMEDIATE SOURCE:
( B ) CLONE: E. coli NM522(pMYC1642) NRRL B-18961

( x i ) SEQUENCE DESCRIPTION: SEQ ID NO:9:

```
ATGACTTGTC AATTACAAGC GCAACCACTT ATTCCCTATA ACGTACTAGC AGGAGTTCCA     60

ACTAGTAATA CAGGTAGTCC AATCGGCAAT GCAGGTAATC AATTTGATCA GTTTGAGCAA    120

ACCGTTAAAG AGCTCAAGGA AGCATGGGAA GCGTTCCAAA AAAACGGAAG TTTCTCATTA    180

GCAGCTCTTG AAAAGGGATT TGATGCAGCA ATCGGAGGAG GATCCTTTGA TTATTTAGGT    240

TTAGTTCAAG CCGGCCTAGG ATTAGTTGGT ACGCTAGGCG CCGCAATCCC TGGTGTTTCA    300
```

```
GTGGCAGTGC CTCTTATTAG CATGCTTGTT GGTGTTTTTT GGCCAAAGGG CACAAACAAC    360

CAAGAAAACC TTATTACAGT TATTGATAAG GAAGTTCAGA GAATACTAGA TGAAAAGCTA    420

TCTGATCAGT TAATAAAGAA ATTGAACGCA GATTTAAATG CTTTTACGGA CCTAGTAACT    480

CGTTTGGAAG AAGTAATAAT AGATGCAACT TTCGAGAATC ACAAGCCTGT ACTACAAGTA    540

AGTAAATCAA ATTATATGAA AGTGGATTCA GCATATTTCT CAACAGGAGG TATTCTTACT    600

CTTGGCATGA GTGATTTTCT TACTGATACC TATTCAAAGC TTACCTTCCC ATTATATGTA    660

CTAGGCGCAA CTATGAAACT TTCAGCATAT CATAGTTATA TACAATTCGG AAATACATGG    720

CTTAATAAAG TTTATGATTT ATCATCAGAT GAGGGAAAAA CAATGTCGCA GGCTTTAGCA    780

CGAGCTAAAC AGCATATGCG CCAAGACATA GCATTTTATA CAAGCCAAGC TTTAAACATG    840

TTTACTGGGA ATCTCCCTTC ATTATCATCT AATAAATATG CAATTAATGA CTATAATGTA    900

TACACTCGAG CAATGGTATT GAATGGCTTA GATATAGTAG CAACATGGCC TACCCTATAT    960

CCAGATGACT ATTCGTCTCA GATAAAACTG GAGAAAACAC GCGTGATCTT TTCAGATATG   1020

GTCGGGCAAA GTGAGAGTAG AGATGGCAGC GTAACGATTA AAAATATTTT TGACAATACA   1080

GATTCACATC AACATGGATC CATAGGTCTC AATTCAATCT CTTATTTCCC AGATGAGTTA   1140

CAGAAAGCAC AACTTCGCAT GTATGATTAT AATCACAAAC CTTATTGTAC GGACTGTTTC   1200

TGCTGGCCGT ATGGAGTGAT TTTAAACTAT AACAAGAATA CCTTTAGATA TGGCGATAAT   1260

GATCCAGGTC TTTCAGGAGA CGTTCAACTC CCAGCACCTA TGAGTGTAGT TAATGCCCAA   1320

ACTCAAACAG CCCAATATAC AGATGGAGAA AACATATGGA CAGATACTGG CCGCAGTTGG   1380

CTTTGTACTC TACGTGGCTA CTGTACTACA AACTGTTTTC CAGGAAGAGG TTGTTATAAT   1440

AATAGTACTG GATATGGAGA AAGTTGCAAT CAATCACTTC CAGGTCAAAA AATACATGCA   1500

CTATATCCTT TTACACAAAC AAATGTGCTG GGACAATCAG GCAAACTAGG ATTGCTAGCA   1560

AGTCATATTC CATATGACCT AAGTCCGAAC AATACGATTG GTGACAAAGA TACAGATTCT   1620

ACGAATATTG TCGCAAAAGG AATTCCAGTG GAAAAGGGT ATGCATCCAG TGGACAAAAA   1680

GTTGAAATTA TACGAGAGTG GATAAATGGT GCGAATGTAG TTCAATTATC TCCAGGCCAA   1740

TCTTGGGGAA TGGATTTTAC CAATAGCACA GGTGGTCAAT ATATGGTCCG CTGTCGATAT   1800

GCAAGTACAA ACGATACTCC AATCTTTTTT AATTTAGTGT ATGACGGGGG ATCGAATCCT   1860

ATTTATAACC AGATGACATT CCCTGCTACA AAAGAGACTC CAGCTCACGA TTCAGTAGAT   1920

AACAAGATAC TAGGCATAAA AGGAATAAAT GGAAATTATT CACTCATGAA TGTAAAAGAT   1980

TCTGTCGAAC TTCCATCTGG GAAATTTCAT GTTTTTTTCA CAAATAATGG ATCATCTGCT   2040

ATTTATTTAG ATCGACTTGA GTTTGTTCCT TTAGATCAAC CAGCAGCGCC AACACAGTCA   2100

ACACAACCAA TTAATTATCC TATCACAAGT AGGTTACCTC ATCGTTCCGG AGAACCACCT   2160

GCAATAATAT GGGAGAAATC AGGGAATGTT CGCGGGAATC AACTAACTAT ATCGGCACAA   2220

GGTGTTCCAG AAAATTCCCA AATATATCTT TCGGTGGGTG GCGATCGCCA AATTTTAGAC   2280

CGTAGCAACG GATTTAAATT AGTTAATTAC TCACCTACTT ATTCTTTCAC TAACATTCAG   2340

GCTAGCTCGT CAAATTTAGT AGATATTACA AGTGGTACCA TCACTGGCCA AGTACAAGTA   2400

TCTAATCTAT AA                                                       2412
```

( 2 ) INFORMATION FOR SEQ ID NO:10:

( i ) SEQUENCE CHARACTERISTICS:
        ( A ) LENGTH: 803 amino acids
        ( B ) TYPE: amino acid
        ( C ) STRANDEDNESS: single ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
    ( A ) ORGANISM: Bacillus thuringiensis
    ( C ) INDIVIDUAL ISOLATE: PS63B ( v i i ) IMMEDIATE SOURCE:
( B ) CLONE: E. coli NM522(pMYC1642) NRRL B-18961

( x i ) SEQUENCE DESCRIPTION: SEQ ID NO:10:

| | | | | | | | | | | | | | | | |
|---|---|---|---|---|---|---|---|---|---|---|---|---|---|---|---|
| Met | Thr | Cys | Gln | Leu | Gln | Ala | Gln | Pro | Leu | Ile | Pro | Tyr | Asn | Val | Leu |
| 1 | | | | 5 | | | | | 10 | | | | | 15 | |
| Ala | Gly | Val | Pro | Thr | Ser | Asn | Thr | Gly | Ser | Pro | Ile | Gly | Asn | Ala | Gly |
| | | | 20 | | | | | 25 | | | | | 30 | | |
| Asn | Gln | Phe | Asp | Gln | Phe | Glu | Gln | Thr | Val | Lys | Glu | Leu | Lys | Glu | Ala |
| | | 35 | | | | | 40 | | | | | 45 | | | |
| Trp | Glu | Ala | Phe | Gln | Lys | Asn | Gly | Ser | Phe | Ser | Leu | Ala | Ala | Leu | Glu |
| | 50 | | | | | 55 | | | | | 60 | | | | |
| Lys | Gly | Phe | Asp | Ala | Ala | Ile | Gly | Gly | Gly | Ser | Phe | Asp | Tyr | Leu | Gly |
| 65 | | | | | 70 | | | | | 75 | | | | | 80 |
| Leu | Val | Gln | Ala | Gly | Leu | Gly | Leu | Val | Gly | Thr | Leu | Gly | Ala | Ala | Ile |
| | | | | 85 | | | | | 90 | | | | | 95 | |
| Pro | Gly | Val | Ser | Val | Ala | Val | Pro | Leu | Ile | Ser | Met | Leu | Val | Gly | Val |
| | | | 100 | | | | | 105 | | | | | 110 | | |
| Phe | Trp | Pro | Lys | Gly | Thr | Asn | Asn | Gln | Glu | Asn | Leu | Ile | Thr | Val | Ile |
| | | 115 | | | | | 120 | | | | | 125 | | | |
| Asp | Lys | Glu | Val | Gln | Arg | Ile | Leu | Asp | Glu | Lys | Leu | Ser | Asp | Gln | Leu |
| | 130 | | | | | 135 | | | | | 140 | | | | |
| Ile | Lys | Lys | Leu | Asn | Ala | Asp | Leu | Asn | Ala | Phe | Thr | Asp | Leu | Val | Thr |
| 145 | | | | | 150 | | | | | 155 | | | | | 160 |
| Arg | Leu | Glu | Glu | Val | Ile | Ile | Asp | Ala | Thr | Phe | Glu | Asn | His | Lys | Pro |
| | | | | 165 | | | | | 170 | | | | | 175 | |
| Val | Leu | Gln | Val | Ser | Lys | Ser | Asn | Tyr | Met | Lys | Val | Asp | Ser | Ala | Tyr |
| | | | 180 | | | | | 185 | | | | | 190 | | |
| Phe | Ser | Thr | Gly | Gly | Ile | Leu | Thr | Leu | Gly | Met | Ser | Asp | Phe | Leu | Thr |
| | | 195 | | | | | 200 | | | | | 205 | | | |
| Asp | Thr | Tyr | Ser | Lys | Leu | Thr | Phe | Pro | Leu | Tyr | Val | Leu | Gly | Ala | Thr |
| | 210 | | | | | 215 | | | | | 220 | | | | |
| Met | Lys | Leu | Ser | Ala | Tyr | His | Ser | Tyr | Ile | Gln | Phe | Gly | Asn | Thr | Trp |
| 225 | | | | | 230 | | | | | 235 | | | | | 240 |
| Leu | Asn | Lys | Val | Tyr | Asp | Leu | Ser | Ser | Asp | Glu | Gly | Lys | Thr | Met | Ser |
| | | | | 245 | | | | | 250 | | | | | 255 | |
| Gln | Ala | Leu | Ala | Arg | Ala | Lys | Gln | His | Met | Arg | Gln | Asp | Ile | Ala | Phe |
| | | | 260 | | | | | 265 | | | | | 270 | | |
| Tyr | Thr | Ser | Gln | Ala | Leu | Asn | Met | Phe | Thr | Gly | Asn | Leu | Pro | Ser | Leu |
| | | 275 | | | | | 280 | | | | | 285 | | | |
| Ser | Ser | Asn | Lys | Tyr | Ala | Ile | Asn | Asp | Tyr | Asn | Val | Tyr | Thr | Arg | Ala |
| | 290 | | | | | 295 | | | | | 300 | | | | |
| Met | Val | Leu | Asn | Gly | Leu | Asp | Ile | Val | Ala | Thr | Trp | Pro | Thr | Leu | Tyr |
| 305 | | | | | 310 | | | | | 315 | | | | | 320 |
| Pro | Asp | Asp | Tyr | Ser | Ser | Gln | Ile | Lys | Leu | Glu | Lys | Thr | Arg | Val | Ile |
| | | | | 325 | | | | | 330 | | | | | 335 | |

| | | | | | | | | | | | | | | |
|---|---|---|---|---|---|---|---|---|---|---|---|---|---|---|
| Phe | Ser | Asp | Met<br>340 | Val | Gly | Gln | Ser<br>345 | Glu | Ser | Arg | Asp | Gly<br>350 | Ser | Val | Thr |
| Ile | Lys | Asn<br>355 | Ile | Phe | Asp | Asn | Thr<br>360 | Asp | Ser | His | Gln | His<br>365 | Gly | Ser | Ile |
| Gly | Leu<br>370 | Asn | Ser | Ile | Ser | Tyr<br>375 | Phe | Pro | Asp | Glu | Leu<br>380 | Gln | Lys | Ala | Gln |
| Leu<br>385 | Arg | Met | Tyr | Asp | Tyr<br>390 | Asn | His | Lys | Pro | Tyr<br>395 | Cys | Thr | Asp | Cys | Phe<br>400 |
| Cys | Trp | Pro | Tyr | Gly<br>405 | Val | Ile | Leu | Asn | Tyr<br>410 | Asn | Lys | Asn | Thr | Phe<br>415 | Arg |
| Tyr | Gly | Asp | Asn<br>420 | Asp | Pro | Gly | Leu | Ser<br>425 | Gly | Asp | Val | Gln | Leu<br>430 | Pro | Ala |
| Pro | Met | Ser<br>435 | Val | Val | Asn | Ala | Gln<br>440 | Thr | Gln | Thr | Ala | Gln<br>445 | Tyr | Thr | Asp |
| Gly | Glu<br>450 | Asn | Ile | Trp | Thr | Asp<br>455 | Thr | Gly | Arg | Ser | Trp<br>460 | Leu | Cys | Thr | Leu |
| Arg<br>465 | Gly | Tyr | Cys | Thr | Thr<br>470 | Asn | Cys | Phe | Pro | Gly<br>475 | Arg | Gly | Cys | Tyr | Asn<br>480 |
| Asn | Ser | Thr | Gly | Tyr<br>485 | Gly | Glu | Ser | Cys | Asn<br>490 | Gln | Ser | Leu | Pro | Gly<br>495 | Gln |
| Lys | Ile | His | Ala<br>500 | Leu | Tyr | Pro | Phe | Thr<br>505 | Gln | Thr | Asn | Val | Leu<br>510 | Gly | Gln |
| Ser | Gly | Lys<br>515 | Leu | Gly | Leu | Leu | Ala<br>520 | Ser | His | Ile | Pro | Tyr<br>525 | Asp | Leu | Ser |
| Pro | Asn<br>530 | Asn | Thr | Ile | Gly | Asp<br>535 | Lys | Asp | Thr | Asp | Ser<br>540 | Thr | Asn | Ile | Val |
| Ala<br>545 | Lys | Gly | Ile | Pro | Val<br>550 | Glu | Lys | Gly | Tyr | Ala<br>555 | Ser | Ser | Gly | Gln | Lys<br>560 |
| Val | Glu | Ile | Ile | Arg<br>565 | Glu | Trp | Ile | Asn | Gly<br>570 | Ala | Asn | Val | Val | Gln<br>575 | Leu |
| Ser | Pro | Gly | Gln<br>580 | Ser | Trp | Gly | Met | Asp<br>585 | Phe | Thr | Asn | Ser | Thr<br>590 | Gly | Gly |
| Gln | Tyr | Met<br>595 | Val | Arg | Cys | Arg | Tyr<br>600 | Ala | Ser | Thr | Asn | Asp<br>605 | Thr | Pro | Ile |
| Phe | Phe<br>610 | Asn | Leu | Val | Tyr | Asp<br>615 | Gly | Gly | Ser | Asn | Pro<br>620 | Ile | Tyr | Asn | Gln |
| Met<br>625 | Thr | Phe | Pro | Ala | Thr<br>630 | Lys | Glu | Thr | Pro | Ala<br>635 | His | Asp | Ser | Val | Asp<br>640 |
| Asn | Lys | Ile | Leu | Gly<br>645 | Ile | Lys | Gly | Ile | Asn<br>650 | Gly | Asn | Tyr | Ser | Leu<br>655 | Met |
| Asn | Val | Lys | Asp<br>660 | Ser | Val | Glu | Leu | Pro<br>665 | Ser | Gly | Lys | Phe | His<br>670 | Val | Phe |
| Phe | Thr | Asn<br>675 | Asn | Gly | Ser | Ser | Ala<br>680 | Ile | Tyr | Leu | Asp | Arg<br>685 | Leu | Glu | Phe |
| Val | Pro<br>690 | Leu | Asp | Gln | Pro | Ala<br>695 | Ala | Pro | Thr | Gln | Ser<br>700 | Thr | Gln | Pro | Ile |
| Asn<br>705 | Tyr | Pro | Ile | Thr | Ser<br>710 | Arg | Leu | Pro | His | Arg<br>715 | Ser | Gly | Glu | Pro | Pro<br>720 |
| Ala | Ile | Ile | Trp | Glu<br>725 | Lys | Ser | Gly | Asn | Val<br>730 | Arg | Gly | Asn | Gln | Leu<br>735 | Thr |
| Ile | Ser | Ala | Gln<br>740 | Gly | Val | Pro | Glu | Asn<br>745 | Ser | Gln | Ile | Tyr | Leu<br>750 | Ser | Val |
| Gly | Gly | Asp | Arg<br>755 | Gln | Ile | Leu | Asp | Arg<br>760 | Ser | Asn | Gly | Phe | Lys<br>765 | Leu | Val |

```
    Asn  Tyr  Ser  Pro  Thr  Tyr  Ser  Phe  Thr  Asn  Ile  Gln  Ala  Ser  Ser  Ser
         770                 775                      780

Asn  Leu  Val  Asp  Ile  Thr  Ser  Gly  Thr  Ile  Thr  Gly  Gln  Val  Gln  Val
    785                      790                      795                      800

Ser  Asn  Leu
```

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
    Arg  Glu  Trp  Ile  Asn  Gly  Ala  Asn
    1                   5
```

( 2 ) INFORMATION FOR SEQ ID NO:12:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:12:

```
AGARTRKWTW  AATGGWGCKM  A                                                         21
```

( 2 ) INFORMATION FOR SEQ ID NO:13:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:13:

```
GARTGGWTAA  ATGGTRMSAA                                                            20
```

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
    Pro  Thr  Phe  Asp  Pro  Asp  Leu  Tyr
    1                   5
```

( 2 ) INFORMATION FOR SEQ ID NO:15:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:15:

CCNACYTTTK ATCCAGATSW YTAT    24

( 2 ) INFORMATION FOR SEQ ID NO:16:

( i ) SEQUENCE CHARACTERISTICS:
    ( A ) LENGTH: 24 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:16:

CCWACWTTYG ATMCASATMW TTAT    24

( 2 ) INFORMATION FOR SEQ ID NO:17:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:17:

Ala Ile Leu Asn Glu Leu Tyr Pro Ser Val Pro Tyr Asn Val
1               5                   10

( 2 ) INFORMATION FOR SEQ ID NO:18:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:18:

Ala Ile Leu Asn Glu Leu Tyr Pro Ser Val Pro Tyr Asn Val
1               5                   10

( 2 ) INFORMATION FOR SEQ ID NO:19:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:19:

Met Ala Thr Ile Asn Glu Leu Tyr Pro Asn Val Pro Tyr Asn Val Leu
1               5                   10                  15

( 2 ) INFORMATION FOR SEQ ID NO:20:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:20:

Gln Leu Gln Ala Gln Pro Leu Ile Pro Tyr Asn Val Leu Ala
1               5                   10

( 2 ) INFORMATION FOR SEQ ID NO:21:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Ala Thr Leu Asn Glu Val Tyr Pro Val Asn
1               5                   10

( 2 ) INFORMATION FOR SEQ ID NO:22:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Val Gln Arg Ile Leu Asp Glu Lys Leu Ser Phe Gln Leu Ile Lys
1               5                   10                  15

( 2 ) INFORMATION FOR SEQ ID NO:23:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:23:

GCAATTTTAA ATGAATTATA TCC                                                      23

( 2 ) INFORMATION FOR SEQ ID NO:24:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:24:

CAAYTACAAG CWCAACC                                                            17

( 2 ) INFORMATION FOR SEQ ID NO:25:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:25:

TTCATCTAAA ATTCTTTGWA C                                                      21

( 2 ) INFORMATION FOR SEQ ID NO:26:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:26:

GCWACWTTAA ATGAAGTWTA T                                                      21

( 2 ) INFORMATION FOR SEQ ID NO:27:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:27:

AATGAAGTWT ATCCWGTWAA T                                                      21

( 2 ) INFORMATION FOR SEQ ID NO:28:

( i ) SEQUENCE CHARACTERISTICS:
        ( A ) LENGTH: 38 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:28:

GCAAGCGGCC GCTTATGGAA TAAATTCAAT TYKRTCWA                                    38

( 2 ) INFORMATION FOR SEQ ID NO:29:

( i ) SEQUENCE CHARACTERISTICS:
        ( A ) LENGTH: 37 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:29:

AGACTGGATC CATGGCWACW ATWAATGAAT TATAYCC                                     37

( 2 ) INFORMATION FOR SEQ ID NO:30:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

Glu Ser Lys Leu Lys Pro Asn Thr Arg Tyr
    1               5                   10

( 2 ) INFORMATION FOR SEQ ID NO:31:

( i ) SEQUENCE CHARACTERISTICS:
   ( A ) LENGTH: 29 bases
   ( B ) TYPE: nucleic acid
   ( C ) STRANDEDNESS: single
   ( D ) TOPOLOGY: linear ( i i ) MOLECULE TYPE: DNA (synthetic)

( x i ) SEQUENCE DESCRIPTION: SEQ ID NO:31:

TAACGTGTAT WCGSTTTTAA TTTWGAYTC    29

( 2 ) INFORMATION FOR SEQ ID NO:32:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:32:

Tyr Ile Asp Lys Ile Glu Phe Ile Pro
   1               5

( 2 ) INFORMATION FOR SEQ ID NO:33:

( i ) SEQUENCE CHARACTERISTICS:
      ( A ) LENGTH: 23 bases
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:33:

TGGAATAAAT TCAATTYKRT CWA    23

( 2 ) INFORMATION FOR SEQ ID NO:34:

( i ) SEQUENCE CHARACTERISTICS:
      ( A ) LENGTH: 23 bases
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:34:

AGGAACAAAY TCAAKWCGRT CTA    23

( 2 ) INFORMATION FOR SEQ ID NO:35:

( i ) SEQUENCE CHARACTERISTICS:
      ( A ) LENGTH: 24 bases
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:35:

TTTAGATCGT MTTGARTTTR TWCC    24

( 2 ) INFORMATION FOR SEQ ID NO:36:

( i ) SEQUENCE CHARACTERISTICS:
      ( A ) LENGTH: 5 amino acids
      ( B ) TYPE: amino acid ( C ) STRANDEDNESS: single
            ( D ) TOPOLOGY: linear ( i i ) MOLECULE TYPE: peptide ( x i ) SEQUENCE DESCRIPTION: SEQ ID NO:36:

Ile Thr Ser Glu Asp
        1               5

( 2 ) INFORMATION FOR SEQ ID NO:37:

( i ) SEQUENCE CHARACTERISTICS:
            ( A ) LENGTH: 20 bases
            ( B ) TYPE: nucleic acid
            ( C ) STRANDEDNESS: single
            ( D ) TOPOLOGY: linear ( i i ) MOLECULE TYPE: DNA (synthetic)

( x i ) SEQUENCE DESCRIPTION: SEQ ID NO:37:

TCTCCATCTT CTGARGWAAT                                                                                        20

( 2 ) INFORMATION FOR SEQ ID NO:38:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:38:

Leu Asp Arg Ile Glu Phe Val Pro
        1               5

( 2 ) INFORMATION FOR SEQ ID NO:39:

( i ) SEQUENCE CHARACTERISTICS:
            ( A ) LENGTH: 731 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: YES ( x i ) SEQUENCE DESCRIPTION: SEQ ID NO:39:

Met Xaa Xaa Xaa Xaa Xaa Xaa Tyr Pro Xaa Xaa Xaa Tyr Xaa Xaa Xaa
        1               5                   10                  15

Xaa Xaa Xaa Xaa Xaa Xaa Xaa Xaa Xaa Xaa Xaa Xaa Xaa Xaa Xaa Xaa
                        20                  25                  30

Xaa Xaa Xaa Xaa Xaa Xaa Xaa Xaa Xaa Xaa Xaa Xaa Xaa Xaa Xaa Xaa
                        35                  40                  45

Xaa Xaa Xaa Xaa Xaa Xaa Xaa Xaa Xaa Xaa Xaa Xaa Xaa Xaa Xaa Xaa
                    50                  55                  60

Xaa Xaa Xaa Xaa Xaa Xaa Xaa Xaa Xaa Xaa Xaa Xaa Xaa Xaa Xaa Xaa
        65                      70                  75                      80

Xaa Xaa Xaa Xaa Xaa Xaa Xaa Xaa Xaa Xaa Pro Xaa Xaa Xaa Xaa Xaa
                        85                  90                  95

Xaa Xaa Xaa Xaa Xaa Xaa Xaa Xaa Xaa Xaa Xaa Xaa Xaa Xaa Xaa Xaa
                        100                 105                 110

Xaa Xaa Xaa Xaa Xaa Xaa Xaa Lys Xaa Xaa Xaa Xaa Xaa Xaa Xaa Xaa
                        115                 120                 125

| Xaa | Xaa | Xaa | Xaa | Xaa | Xaa | Xaa | Xaa | Xaa | Xaa | Xaa | Xaa | Xaa | Xaa | Xaa |
|-----|-----|-----|-----|-----|-----|-----|-----|-----|-----|-----|-----|-----|-----|-----|
| 130 |     |     |     |     | 135 |     |     |     |     | 140 |     |     |     |     |
| Xaa | Xaa | Xaa | Xaa | Xaa | Xaa | Xaa | Xaa | Xaa | Xaa | Xaa | Xaa | Xaa | Xaa | Xaa |
| 145 |     |     |     |     | 150 |     |     |     |     | 155 |     |     |     | 160 |
| Xaa | Xaa | Xaa | Xaa | Xaa | Xaa | Xaa | Xaa | Xaa | Xaa | Xaa | Xaa | Xaa | Xaa | Xaa |
|     |     |     |     | 165 |     |     |     |     | 170 |     |     |     | 175 |     |
| Xaa | Xaa | Xaa | Xaa | Xaa | Xaa | Xaa | Xaa | Xaa | Xaa | Xaa | Xaa | Xaa | Xaa | Xaa |
|     |     |     | 180 |     |     |     |     | 185 |     |     |     |     | 190 |     |
| Xaa | Xaa | Xaa | Xaa | Xaa | Xaa | Xaa | Xaa | Xaa | Xaa | Xaa | Xaa | Xaa | Xaa | Xaa |
|     |     | 195 |     |     |     |     | 200 |     |     |     |     | 205 |     |     |
| Xaa | Xaa | Xaa | Xaa | Xaa | Xaa | Xaa | Xaa | Xaa | Xaa | Xaa | Xaa | Xaa | Xaa | Xaa |
|     | 210 |     |     |     |     | 215 |     |     |     |     | 220 |     |     |     |
| Xaa | Xaa | Xaa | Xaa | Xaa | Glu | Xaa | Xaa | Xaa | Xaa | Xaa | Xaa | Xaa | Xaa | Xaa |
| 225 |     |     |     |     | 230 |     |     |     |     | 235 |     |     |     | 240 |
| Pro | Xaa | Tyr | Xaa | Xaa | Xaa | Xaa | Xaa | Xaa | His | Xaa | Xaa | Xaa | Xaa | Xaa |
|     |     |     | 245 |     |     |     |     |     | 250 |     |     |     |     | 255 |
| Xaa | Xaa | Xaa | Xaa | Xaa | Xaa | Xaa | Xaa | Xaa | Xaa | Xaa | Xaa | Xaa | Xaa | Xaa |
|     |     |     | 260 |     |     |     |     | 265 |     |     |     |     | 270 |     |
| Xaa | Xaa | Xaa | Xaa | Xaa | Xaa | Xaa | Xaa | Xaa | Xaa | Xaa | Xaa | Xaa | Xaa | Xaa |
|     |     | 275 |     |     |     |     | 280 |     |     |     |     | 285 |     |     |
| Xaa | Xaa | Xaa | Xaa | Xaa | Xaa | Xaa | Xaa | Xaa | Xaa | Xaa | Xaa | Xaa | Xaa | Xaa |
|     | 290 |     |     |     |     | 295 |     |     |     |     | 300 |     |     |     |
| Xaa | Xaa | Xaa | Xaa | Xaa | Xaa | Xaa | Xaa | Xaa | Xaa | Xaa | Xaa | Xaa | Xaa | Tyr |
| 305 |     |     |     |     | 310 |     |     |     |     | 315 |     |     |     | 320 |
| Xaa | Xaa | Xaa | Xaa | Xaa | Xaa | Xaa | Xaa | Xaa | Xaa | Xaa | Xaa | Xaa | Xaa | Pro |
|     |     |     |     | 325 |     |     |     |     | 330 |     |     |     | 335 |     |
| Xaa | Xaa | Xaa | Xaa | Xaa | Xaa | Tyr | Xaa | Xaa | Xaa | Xaa | Xaa | Xaa | Xaa | Xaa |
|     |     |     | 340 |     |     |     |     | 345 |     |     |     |     | 350 |     |
| Xaa | Xaa | Xaa | Xaa | Xaa | Xaa | Xaa | Xaa | Xaa | Xaa | Xaa | Xaa | Xaa | Xaa | Xaa |
|     |     | 355 |     |     |     |     | 360 |     |     |     |     | 365 |     |     |
| Xaa | Xaa | Xaa | Xaa | Xaa | Xaa | Xaa | Xaa | Xaa | Xaa | Xaa | Xaa | Xaa | Xaa | Xaa |
|     | 370 |     |     |     |     | 375 |     |     |     |     | 380 |     |     |     |
| Xaa | Xaa | Xaa | Xaa | Xaa | Xaa | Xaa | Xaa | Xaa | Xaa | Xaa | Xaa | Xaa | Xaa | Xaa |
| 385 |     |     |     |     | 390 |     |     |     |     | 395 |     |     |     | 400 |
| Xaa | Xaa | Xaa | Xaa | Xaa | Xaa | Xaa | Xaa | Xaa | Xaa | Xaa | Xaa | Xaa | Xaa | Xaa |
|     |     |     |     | 405 |     |     |     |     | 410 |     |     |     | 415 |     |
| Xaa | Xaa | Xaa | Xaa | Xaa | Xaa | Xaa | Xaa | Xaa | Xaa | Xaa | Xaa | Xaa | Xaa | Xaa |
|     |     |     | 420 |     |     |     |     | 425 |     |     |     |     | 430 |     |
| Xaa | Xaa | Xaa | Xaa | Xaa | Xaa | Xaa | Xaa | Xaa | Xaa | Xaa | Xaa | Xaa | Xaa | Xaa |
|     |     | 435 |     |     |     |     | 440 |     |     |     |     | 445 |     |     |
| Xaa | Xaa | Xaa | Xaa | Xaa | Xaa | Xaa | Xaa | Xaa | Xaa | Xaa | Xaa | Xaa | Xaa | Xaa |
|     | 450 |     |     |     |     | 455 |     |     |     |     | 460 |     |     |     |
| Xaa | Xaa | Xaa | Xaa | Xaa | Xaa | Xaa | Xaa | Pro | Xaa | Xaa | Xaa | Xaa | Xaa | Xaa |
| 465 |     |     |     |     | 470 |     |     |     |     | 475 |     |     |     | 480 |
| Xaa | Xaa | Xaa | Xaa | Xaa | Xaa | Xaa | Xaa | Xaa | Xaa | Xaa | Xaa | Xaa | Xaa | Xaa |
|     |     |     |     | 485 |     |     |     |     | 490 |     |     |     | 495 |     |
| Xaa | Xaa | Xaa | Xaa | Xaa | Xaa | Xaa | Xaa | Xaa | Xaa | Xaa | Xaa | Xaa | Xaa | Xaa |
|     |     |     | 500 |     |     |     |     | 505 |     |     |     |     | 510 |     |
| Xaa | Xaa | Xaa | Xaa | Xaa | Xaa | Xaa | Xaa | Xaa | Xaa | Xaa | Xaa | Xaa | Xaa | Xaa |
|     |     | 515 |     |     |     |     | 520 |     |     |     |     | 525 |     |     |
| Xaa | Xaa | Xaa | Xaa | Xaa | Xaa | Xaa | Xaa | Xaa | Xaa | Xaa | Xaa | Xaa | Tyr | Xaa | Xaa |
|     | 530 |     |     |     |     | 535 |     |     |     |     | 540 |     |     |     |     |
| Xaa | Xaa | Xaa | Xaa | Xaa | Xaa | Xaa | Xaa | Xaa | Xaa | Xaa | Xaa | Xaa | Xaa | Xaa |
| 545 |     |     |     |     | 550 |     |     |     |     | 555 |     |     |     | 560 |

```
Xaa  Xaa  Xaa  Xaa  Xaa  Xaa  Xaa  Xaa  Xaa  Xaa  Xaa  Xaa  Xaa  Xaa  Xaa
               565                      570                     575

Xaa  Xaa  Xaa  Xaa  Xaa  Xaa  Xaa  Xaa  Xaa  Xaa  Xaa  Xaa  Xaa  Xaa  Xaa
               580                      585                     590

Xaa  Xaa  Xaa  Xaa  Xaa  Xaa  Xaa  Xaa  Xaa  Xaa  Xaa  Xaa  Xaa  Xaa  Xaa
               595                      600                     605

Xaa  Xaa  Xaa  Xaa  Xaa  Xaa  Xaa  Xaa  Xaa  Xaa  Xaa  Xaa  Xaa  Xaa  Xaa
     610                      615                     620

Xaa  Xaa  Xaa  Xaa  Xaa  Xaa  Xaa  Xaa  Xaa  Xaa  Xaa  Xaa  Tyr  Xaa  Xaa
625                      630                     635                     640

Xaa  Xaa  Xaa  Xaa  Pro  Xaa  Xaa  Xaa  Xaa  Xaa  Xaa  Xaa  Xaa  Xaa  Xaa
               645                      650                     655

Xaa  Xaa  Xaa  Xaa  Xaa  Xaa  Xaa  Xaa  Xaa  Xaa  Xaa  Xaa  Xaa  Xaa  Xaa
               660                      665                     670

Xaa  Xaa  Xaa  Xaa  Xaa  Xaa  Xaa  Xaa  Xaa  Xaa  Xaa  Xaa  Xaa  Xaa  Tyr  Xaa
               675                      680                     685

Xaa  Xaa  Xaa  Xaa  Xaa  Xaa  Xaa  Xaa  Xaa  Xaa  Xaa  Xaa  Xaa  Xaa  Xaa
     690                      695                     700

Xaa  Xaa  Xaa  Xaa  Xaa  Xaa  Xaa  Xaa  Xaa  Xaa  Xaa  Xaa  Xaa  Xaa  Xaa
705                      710                     715                     720

Xaa  Xaa  Xaa  Xaa  Xaa  Xaa  Xaa  Xaa  Pro  Xaa  Xaa
               725                      730
```

( 2 ) INFORMATION FOR SEQ ID NO:40:

( i ) SEQUENCE CHARACTERISTICS:
        ( A ) LENGTH: 37 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:40:

AGACTGGATC CATGGCWACW ATWAATGAAT TATAYCC 37

( 2 ) INFORMATION FOR SEQ ID NO:41:

( i ) SEQUENCE CHARACTERISTICS:
        ( A ) LENGTH: 48 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:41:

GACTGCGGCC GCGTCGACTT AACGTGTATW CGSTTTTAAT TTWGAYTC 48

( 2 ) INFORMATION FOR SEQ ID NO:42:

( i ) SEQUENCE CHARACTERISTICS:
        ( A ) LENGTH: 3660 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

(A) ORGANISM: Bacillus thuringiensis
(C) INDIVIDUAL ISOLATE: PS86Q3

(vii) IMMEDIATE SOURCE:
(A) LI

| | | | | | |
|---|---|---|---|---|---|
| ACTAGTCTTA | CTGATTGTGA | TTGTAATAAC | CCTCGTGGCA | TAGATTGTAC | GCTATGTTGT | 2160 |
| CAGGTAGAAA | ATCAGCTACC | TTCTTTTGTG | ACACTTACAG | ATTTACGAAA | TATCACATCC | 2220 |
| CAAGTGAATG | GTCTATTTGC | ACCTGGAACA | CAAAATAGGC | TGGCTCAAAA | TATAAGTGAT | 2280 |
| CATGATATTG | AAGAAGTTGT | ATTGAAAGTG | GATGCCTTAT | CAGATGAGAT | ATTTGGAACA | 2340 |
| AATAAGAAGG | CTTTACGTAA | ATTGGTGAAT | CAAGCAAAAC | GTTTGAGTAG | AGCAAGAAAT | 2400 |
| CTTCTGATAG | GTGGTAGTTT | TGAAAATTGG | GATGCATGGT | ATAAAGGAAG | AAATGTAGTA | 2460 |
| ACTGTATCTG | ATCATGAACT | ATTTAAGAGT | GATCATGTAT | TATTACCACC | ACCAGGATTG | 2520 |
| TCTCCATCTT | ATATTTTCCA | AAAAGTGGAG | GAATCTAAAT | TAAAAGCAAA | TACACGTTAT | 2580 |
| ACGGTTTCTG | GATTTATTGC | GCATGCAACA | GATTTAGAAA | TTGTGGTTTC | TCGTTATGGG | 2640 |
| CAAGAAATAA | AGAAAGTGGT | GCAAGTTCCT | TATGGAGAAG | CATTCCCATT | AACATCAAGT | 2700 |
| GGACCAGTTT | GTTGTATCCC | ACATTCTACA | AGTAATGGAA | CTTTAGGCAA | TCCACATTTC | 2760 |
| TTTAGTTACA | GTATTGATGT | AGGTGCATTA | GATGTAGACA | CAAACCCTGG | TATTGAATTC | 2820 |
| GGTCTTCGTA | TTGTAAATCC | AACTGGAATG | GCACGCGTAA | GCAATTTGGA | AATTCGTGAA | 2880 |
| GATCGTCCAT | TAGCAGCAAA | TGAAATACGA | CAAGTACAAC | GTGTCGCAAG | AAATTGGAGA | 2940 |
| ACCGAGTATG | AGAAAGAACG | TGCGGAAGTA | ACAAGTTTAA | TTCAACCTGT | TATCAATCGA | 3000 |
| ATCAACGGAT | TGTATGAAAA | TGAAAATTGG | AACGGTTCTA | TTCGTTCAGA | TATTTCGTAT | 3060 |
| CAGAATATAG | ACGCGATTGT | ATTACCAACG | TTACCAACGT | TACGCCATTG | GTTTATGTCA | 3120 |
| GATAGATTCA | GTGAACAAGG | AGATATCATG | GCTAAATTCC | AAGGTGCATT | AAATCGTGCG | 3180 |
| TATGCACAAC | TGGAACAAAG | TACGCTTCTG | CATAATGGTC | ATTTTACAAA | AGATGCAGCT | 3240 |
| AATTGGACAA | TAGAAGGCGA | TGCACATCAG | ATAACACTAG | AAGATGGTAG | ACGTGTATTG | 3300 |
| CGACTTCCAG | ATTGGTCTTC | GAGTGTATCT | CAAATGATTG | AAATCGAGAA | TTTTAATCCA | 3360 |
| GATAAAGAAT | ACAACTTAGT | ATTCCATGGG | CAAGGAGAAG | GAACGGTTAC | GTTGGAGCAT | 3420 |
| GGAGAAGAAA | CAAATATAT | AGAAACGCAT | ACACATCATT | TTGCGAATTT | TACAACTTCT | 3480 |
| CAACGTCAAG | GACTCACGTT | TGAATCAAAT | AAAGTGACAG | TGACCATTTC | TTCAGAAGAT | 3540 |
| GGAGAATTCT | TAGTGGATAA | TATTGCGCTT | GTGGAAGCTC | CTCTTCCTAC | AGATGACCAA | 3600 |
| AATTCTGAGG | GAAATACGGC | TTTCAGTACG | AATAGCGATA | CAAGTATGAA | CAACAATCAA | 3660 |

( 2 ) INFORMATION FOR SEQ ID NO:43:

( i ) SEQUENCE CHARACTERISTICS:
        ( A ) LENGTH: 1220 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Bacillus thuringiensis
( C ) INDIVIDUAL ISOLATE: 86Q3

( v i i ) IMMEDIATE SOURCE:
( A ) LIBRARY: Lambdagem (TM) - 11 library of Luis Foncerrada
( B ) CLONE: 86Q3c ( x i ) SEQUENCE DESCRIPTION: SEQ ID NO:43:

Met Ala Ile Leu Asn Glu Leu Tyr Pro Ser Val Pro Tyr Asn Val Leu
1 5 10 15

| | | | | | | | | | | | | | | |
|---|---|---|---|---|---|---|---|---|---|---|---|---|---|---|
|Ala|Tyr|Thr|Pro 20|Pro|Ser|Phe|Leu|Pro 25|Asp|Ala|Gly|Thr|Gln 30|Ala|Thr|
|Pro|Ala|Asp 35|Leu|Thr|Ala|Tyr|Glu 40|Gln|Leu|Leu|Lys|Asn 45|Leu|Glu|Lys|
|Gly|Ile|Asn|Ala|Gly|Thr|Tyr 55|Ser|Lys|Ala|Ile|Ala|Asp|Val|Leu|Lys|
| |50| | | | | | | | |60| | | | | |
|Gly 65|Ile|Phe|Ile|Asp|Asp 70|Thr|Ile|Asn|Tyr|Gln 75|Thr|Tyr|Val|Asn|Ile 80|
|Gly|Leu|Ser|Leu|Ile 85|Thr|Leu|Ala|Val|Pro 90|Glu|Ile|Gly|Ile|Phe 95|Thr|
|Pro|Phe|Ile|Gly 100|Leu|Phe|Phe|Ala|Ala 105|Leu|Asn|Lys|His|Asp 110|Ala|Pro|
|Pro|Pro|Pro 115|Asn|Ala|Lys|Asp|Ile 120|Phe|Glu|Ala|Met|Lys 125|Pro|Ala|Ile|
|Gln|Glu 130|Met|Ile|Asp|Arg|Thr 135|Leu|Thr|Ala|Asp|Glu 140|Gln|Thr|Phe|Leu|
|Asn 145|Gly|Glu|Ile|Ser|Gly 150|Leu|Gln|Asn|Leu|Ala 155|Ala|Arg|Tyr|Gln|Ser 160|
|Thr|Met|Asp|Asp|Ile 165|Gln|Ser|His|Gly|Gly 170|Phe|Asn|Lys|Val|Asp 175|Ser|
|Gly|Leu|Ile|Lys 180|Lys|Phe|Thr|Asp|Glu 185|Val|Leu|Ser|Leu|Asn 190|Ser|Phe|
|Tyr|Thr|Asp 195|Arg|Leu|Pro|Val|Phe 200|Ile|Thr|Asp|Asn|Thr 205|Ala|Asp|Arg|
|Thr|Leu 210|Leu|Gly|Leu|Pro|Tyr 215|Tyr|Ala|Ile|Leu|Ala 220|Ser|Met|His|Leu|
|Met 225|Leu|Leu|Arg|Asp|Ile 230|Ile|Thr|Lys|Gly|Pro 235|Thr|Trp|Asp|Ser|Lys 240|
|Ile|Asn|Phe|Thr|Pro 245|Asp|Ala|Ile|Asp|Ser 250|Phe|Lys|Thr|Asp|Ile 255|Lys|
|Asn|Asn|Ile|Lys 260|Leu|Tyr|Ser|Lys|Thr 265|Ile|Tyr|Asp|Val|Phe 270|Gln|Lys|
|Gly|Leu|Ala 275|Ser|Tyr|Gly|Thr|Pro 280|Ser|Asp|Leu|Glu|Ser 285|Phe|Ala|Lys|
|Lys|Lys 290|Lys|Tyr|Ile|Glu|Ile 295|Met|Thr|Thr|His|Cys 300|Leu|Asp|Phe|Ala|
|Arg 305|Leu|Phe|Pro|Thr|Phe 310|Asp|Pro|Asp|Leu|Tyr 315|Pro|Thr|Gly|Ser|Gly 320|
|Asp|Ile|Ser|Leu|Gln 325|Lys|Thr|Arg|Arg|Ile 330|Leu|Ser|Pro|Phe|Ile 335|Pro|
|Ile|Arg|Thr|Ala 340|Asp|Gly|Leu|Thr|Leu 345|Asn|Asn|Thr|Ser|Ile 350|Asp|Thr|
|Ser|Asn|Trp 355|Pro|Asn|Tyr|Glu|Asn 360|Gly|Asn|Gly|Ala|Phe 365|Pro|Asn|Pro|
|Lys|Glu 370|Arg|Ile|Leu|Lys|Gln 375|Phe|Lys|Leu|Tyr|Pro 380|Ser|Trp|Arg|Ala|
|Gly 385|Gln|Tyr|Gly|Gly|Leu 390|Leu|Gln|Pro|Tyr|Leu 395|Trp|Ala|Ile|Glu|Val 400|
|Gln|Asp|Ser|Val|Glu 405|Thr|Arg|Leu|Tyr|Gly 410|Gln|Leu|Pro|Ala|Val 415|Asp|
|Pro|Gln|Ala|Gly 420|Pro|Asn|Tyr|Val|Ser 425|Ile|Asp|Ser|Ser|Asn 430|Pro|Ile|
|Ile|Gln|Ile|Asn|Met|Asp|Thr|Trp|Lys|Thr|Pro|Pro|Gln|Gly|Ala|Ser|

|     |     |     | 435 |     |     |     |     | 440 |     |     |     |     | 445 |     |     |
| --- | --- | --- | --- | --- | --- | --- | --- | --- | --- | --- | --- | --- | --- | --- | --- |
| Gly | Trp | Asn | Thr | Asn | Leu | Met | Arg | Gly | Ser | Val | Ser | Gly | Leu | Ser | Phe |
|     | 450 |     |     |     | 455 |     |     |     |     | 460 |     |     |     |     |     |
| Leu | Gln | Arg | Asp | Gly | Thr | Arg | Leu | Ser | Ala | Gly | Met | Gly | Gly | Gly | Phe |
| 465 |     |     |     |     | 470 |     |     |     |     | 475 |     |     |     |     | 480 |
| Ala | Asp | Thr | Ile | Tyr | Ser | Leu | Pro | Ala | Thr | His | Tyr | Leu | Ser | Tyr | Leu |
|     |     |     |     | 485 |     |     |     |     | 490 |     |     |     |     | 495 |     |
| Tyr | Gly | Thr | Pro | Tyr | Gln | Thr | Ser | Asp | Asn | Tyr | Ser | Gly | His | Val | Gly |
|     |     |     | 500 |     |     |     |     | 505 |     |     |     |     | 510 |     |     |
| Ala | Leu | Val | Gly | Val | Ser | Thr | Pro | Gln | Glu | Ala | Thr | Leu | Pro | Asn | Ile |
|     |     | 515 |     |     |     |     | 520 |     |     |     |     | 525 |     |     |     |
| Ile | Gly | Gln | Pro | Asp | Glu | Gln | Gly | Asn | Val | Ser | Thr | Met | Gly | Phe | Pro |
|     | 530 |     |     |     |     | 535 |     |     |     |     |     | 540 |     |     |     |
| Phe | Glu | Lys | Ala | Ser | Tyr | Gly | Gly | Thr | Val | Val | Lys | Glu | Trp | Leu | Asn |
| 545 |     |     |     |     | 550 |     |     |     |     | 555 |     |     |     |     | 560 |
| Gly | Ala | Asn | Ala | Met | Lys | Leu | Ser | Pro | Gly | Gln | Ser | Ile | Gly | Ile | Pro |
|     |     |     |     | 565 |     |     |     |     | 570 |     |     |     |     | 575 |     |
| Ile | Thr | Asn | Val | Thr | Lys | His | Asn | Tyr | Gln | Val | Arg | Cys | Arg | Tyr | Ala |
|     |     |     | 580 |     |     |     |     | 585 |     |     |     |     | 590 |     |     |
| Ser | Asn | Ser | Asp | Asn | Pro | Val | Phe | Phe | Asn | Val | Asp | Thr | Gly | Gly | Ala |
|     |     | 595 |     |     |     |     | 600 |     |     |     |     | 605 |     |     |     |
| Asn | Pro | Ile | Phe | Gln | Gln | Ile | Asn | Phe | Ala | Ser | Thr | Val | Asp | Ser | Asn |
|     | 610 |     |     |     |     | 615 |     |     |     |     | 620 |     |     |     |     |
| Met | Gly | Val | Lys | Glu | Glu | Asn | Gly | Val | Tyr | Val | Val | Lys | Ser | Ile | Lys |
| 625 |     |     |     |     | 630 |     |     |     |     | 635 |     |     |     |     | 640 |
| Thr | Val | Glu | Ile | Pro | Ala | Gly | Ser | Phe | Tyr | Val | His | Val | Thr | Asn | Gln |
|     |     |     |     | 645 |     |     |     |     | 650 |     |     |     |     | 655 |     |
| Gly | Ser | Ser | Asp | Leu | Phe | Leu | Asp | Arg | Ile | Glu | Phe | Val | Pro | Lys | Ile |
|     |     |     | 660 |     |     |     |     | 665 |     |     |     |     | 670 |     |     |
| Gln | Phe | Gln | Phe | Cys | Asp | Asn | Asn | Leu | His | Cys | Asp | Cys | Asn | Asn |
|     |     |     | 675 |     |     |     |     | 680 |     |     |     |     | 685 |     |     |
| Pro | Val | Asp | Thr | Asp | Cys | Thr | Phe | Cys | Cys | Val | Cys | Thr | Ser | Leu | Thr |
|     | 690 |     |     |     |     | 695 |     |     |     |     | 700 |     |     |     |     |
| Asp | Cys | Asp | Cys | Asn | Asn | Pro | Arg | Gly | Ile | Asp | Cys | Thr | Leu | Cys | Cys |
| 705 |     |     |     |     | 710 |     |     |     |     | 715 |     |     |     |     | 720 |
| Gln | Val | Glu | Asn | Gln | Leu | Pro | Ser | Phe | Val | Thr | Leu | Thr | Asp | Leu | Arg |
|     |     |     |     | 725 |     |     |     |     | 730 |     |     |     |     | 735 |     |
| Asn | Ile | Thr | Ser | Gln | Val | Asn | Gly | Leu | Phe | Ala | Pro | Gly | Thr | Gln | Asn |
|     |     |     | 740 |     |     |     |     | 745 |     |     |     |     | 750 |     |     |
| Arg | Leu | Ala | Gln | Asn | Ile | Ser | Asp | His | Asp | Ile | Glu | Glu | Val | Val | Leu |
|     |     | 755 |     |     |     |     | 760 |     |     |     |     | 765 |     |     |     |
| Lys | Val | Asp | Ala | Leu | Ser | Asp | Glu | Ile | Phe | Gly | Thr | Asn | Lys | Lys | Ala |
|     | 770 |     |     |     |     | 775 |     |     |     |     | 780 |     |     |     |     |
| Leu | Arg | Lys | Leu | Val | Asn | Gln | Ala | Lys | Arg | Leu | Ser | Arg | Ala | Arg | Asn |
| 785 |     |     |     |     | 790 |     |     |     |     | 795 |     |     |     |     | 800 |
| Leu | Leu | Ile | Gly | Gly | Ser | Phe | Glu | Asn | Trp | Asp | Ala | Trp | Tyr | Lys | Gly |
|     |     |     |     | 805 |     |     |     |     | 810 |     |     |     |     | 815 |     |
| Arg | Asn | Val | Val | Thr | Val | Ser | Asp | His | Glu | Leu | Phe | Lys | Ser | Asp | His |
|     |     |     | 820 |     |     |     |     | 825 |     |     |     |     | 830 |     |     |
| Val | Leu | Leu | Pro | Pro | Pro | Gly | Leu | Ser | Pro | Ser | Tyr | Ile | Phe | Gln | Lys |
|     |     | 835 |     |     |     |     | 840 |     |     |     |     | 845 |     |     |     |
| Val | Glu | Glu | Ser | Lys | Leu | Lys | Ala | Asn | Thr | Arg | Tyr | Thr | Val | Ser | Gly |
|     | 850 |     |     |     |     | 855 |     |     |     |     | 860 |     |     |     |     |

-continued

```
Phe  Ile  Ala  His  Ala  Thr  Asp  Leu  Glu  Ile  Val  Val  Ser  Arg  Tyr  Gly
865                      870                 875                           880

Gln  Glu  Ile  Lys  Lys  Val  Val  Gln  Val  Pro  Tyr  Gly  Glu  Ala  Phe  Pro
                    885                 890                           895

Leu  Thr  Ser  Ser  Gly  Pro  Val  Cys  Cys  Ile  Pro  His  Ser  Thr  Ser  Asn
               900                 905                      910

Gly  Thr  Leu  Gly  Asn  Pro  His  Phe  Phe  Ser  Tyr  Ser  Ile  Asp  Val  Gly
          915                      920                      925

Ala  Leu  Asp  Val  Asp  Thr  Asn  Pro  Gly  Ile  Glu  Phe  Gly  Leu  Arg  Ile
          930                 935                      940

Val  Asn  Pro  Thr  Gly  Met  Ala  Arg  Val  Ser  Asn  Leu  Glu  Ile  Arg  Glu
945                 950                      955                           960

Asp  Arg  Pro  Leu  Ala  Ala  Asn  Glu  Ile  Arg  Gln  Val  Gln  Arg  Val  Ala
               965                      970                           975

Arg  Asn  Trp  Arg  Thr  Glu  Tyr  Glu  Lys  Glu  Arg  Ala  Glu  Val  Thr  Ser
               980                 985                           990

Leu  Ile  Gln  Pro  Val  Ile  Asn  Arg  Ile  Asn  Gly  Leu  Tyr  Glu  Asn  Glu
          995                      1000                     1005

Asn  Trp  Asn  Gly  Ser  Ile  Arg  Ser  Asp  Ile  Ser  Tyr  Gln  Asn  Ile  Asp
1010                     1015                     1020

Ala  Ile  Val  Leu  Pro  Thr  Leu  Pro  Thr  Leu  Arg  His  Trp  Phe  Met  Ser
1025                     1030                     1035                     1040

Asp  Arg  Phe  Ser  Glu  Gln  Gly  Asp  Ile  Met  Ala  Lys  Phe  Gln  Gly  Ala
               1045                     1050                     1055

Leu  Asn  Arg  Ala  Tyr  Ala  Gln  Leu  Glu  Gln  Ser  Thr  Leu  Leu  His  Asn
               1060                     1065                     1070

Gly  His  Phe  Thr  Lys  Asp  Ala  Ala  Asn  Trp  Thr  Ile  Glu  Gly  Asp  Ala
               1075                     1080                     1085

His  Gln  Ile  Thr  Leu  Glu  Asp  Gly  Arg  Arg  Val  Leu  Arg  Leu  Pro  Asp
               1090                     1095                     1100

Trp  Ser  Ser  Ser  Val  Ser  Gln  Met  Ile  Glu  Ile  Glu  Asn  Phe  Asn  Pro
1105                     1110                     1115                     1120

Asp  Lys  Glu  Tyr  Asn  Leu  Val  Phe  His  Gly  Gln  Gly  Glu  Gly  Thr  Val
                    1125                     1130                     1135

Thr  Leu  Glu  His  Gly  Glu  Glu  Thr  Lys  Tyr  Ile  Glu  Thr  His  Thr  His
               1140                     1145                     1150

His  Phe  Ala  Asn  Phe  Thr  Thr  Ser  Gln  Arg  Gln  Gly  Leu  Thr  Phe  Glu
               1155                     1160                     1165

Ser  Asn  Lys  Val  Thr  Val  Thr  Ile  Ser  Ser  Glu  Asp  Gly  Glu  Phe  Leu
     1170                     1175                     1180

Val  Asp  Asn  Ile  Ala  Leu  Val  Glu  Ala  Pro  Leu  Pro  Thr  Asp  Asp  Gln
1185                     1190                     1195                     1200

Asn  Ser  Glu  Gly  Asn  Thr  Ala  Phe  Ser  Thr  Asn  Ser  Asp  Thr  Ser  Met
                    1205                     1210                     1215

Asn  Asn  Asn  Gln
               1220
```

( 2 ) INFORMATION FOR SEQ ID NO:44:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:44:

Ala Asn Thr Thr Gln Ser Phe His Phe Ser Asn Ile Leu Asp Tyr Lys
1               5                   10                  15

( 2 ) INFORMATION FOR SEQ ID NO:45:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:45:

TTTCATTTTT CWAATATTTT AGATTATAAA                                                30

( 2 ) INFORMATION FOR SEQ ID NO:46:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:46:

Gly Ile Gly Phe Glu Leu Asp Thr Tyr Ala Asn Ala Pro Glu Asp Glu
1               5                   10                  15

Val ( 2 ) INFORMATION FOR SEQ ID NO:47:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:47:

Ala Ala Ser Asp Tyr Ile Asp Pro Ile Phe
1               5                   10

( 2 ) INFORMATION FOR SEQ ID NO:48:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:48:

GCAGGATCCG ATTATATTWG ATATWAVTCC                                                30

( 2 ) INFORMATION FOR SEQ ID NO:49:

( i ) SEQUENCE CHARACTERISTICS:
( A ) LENGTH: 40 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:49:

GCGGCCGCAC TTCATCTTCW GGWGCATTWG CATAWGTATC    40

( 2 ) INFORMATION FOR SEQ ID NO:50:

( i ) SEQUENCE CHARACTERISTICS:
        ( A ) LENGTH: 2172 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

| | | | | | | |
|---|---|---|---|---|---|---|
| ATGAAAGAAC | AAAATCTAAA | TAAATATGAT | GAAATAACTG | TACAAGCAGC | AAGCGATTAT | 60 |
| ATCGACATTC | GTCCGATTTT | TCAAACAAAT | GGATCTGCTA | CATTTAATTC | TAATACCAAT | 120 |
| ATTACAACTT | TAACACAAGC | TATAAATAGT | CAAGCAGGAG | CAATTGCAGG | AAAGACTGCT | 180 |
| CTAGATATGA | GACATGACTT | TACTTTTAGA | GCAGATATTT | TTCTTGGAAC | TAAAAGTAAC | 240 |
| GGAGCAGACG | GTATTGCAAT | CGCATTTCAT | AGAGGATCAA | TTGGGTTTGT | TGGAACAAAA | 300 |
| GGCGGAGGAC | TTGGAATATT | AGGTGCACCT | AAAGGGATAG | GGTTTGAATT | AGACACATAT | 360 |
| GCGAATGCAC | CTGAGGACGA | AGTAGGCGAT | TCGTTTGGGC | ATGGGGCAAT | GAAAGGATCA | 420 |
| TTCCCTAGTT | TCCCAAATGG | ATATCCCCAT | GCTGGCTTTG | TAAGTACTGA | TAAAAATAGT | 480 |
| AGATGGTTAT | CAGCTCTAGC | TCAGATGCAG | CGAATCGCTG | CTCCAAACGG | GCGTTGGAGA | 540 |
| CGTCTGGAGA | TTCGTTGGGA | TGCTCGTAAT | AAAGAGTTAA | CTGCAAATCT | TCAGGATTTA | 600 |
| ACTTTTAATG | ACATAACTGT | TGGAGAGAAG | CCACGTACTC | CAAGAACTGC | AACTTGGAGG | 660 |
| TTAGTAAATC | CTGCATTTGA | ACTTGATCAG | AAGTATACTT | TTGTTATTGG | TTCGGCGACG | 720 |
| GGTGCATCTA | ATAACCTACA | TCAGATTGGG | ATTATAGAAT | TTGATGCATA | CTTTACTAAA | 780 |
| CCGACAATAG | AAGCGAATAA | TGTAAATGTC | CCAGTGGGAG | CAACATTTAA | TCCAAAAACA | 840 |
| TATCCAGGAA | TAAATTTAAG | AGCAACAGAT | GAGATAGATG | GGGATTTGAC | ATCGAAGATT | 900 |
| ATTGTGAAAG | CAAACAATGT | TAATACGTCG | AAAACGGGTG | TGTATTATGT | GACGTATTAT | 960 |
| GTAGAGAATA | GTTATGGGGA | AAGTGATGAA | AAAACAATCG | AAGTAACTGT | GTTTTCAAAC | 1020 |
| CCTACAATTA | TTGCAAGTGA | TGTTGAAATT | GAAAAAGGGG | AATCTTTTAA | CCCACTAACT | 1080 |
| GATTCAAGAG | TAGGTCTTTC | TGCACAGGAT | TCATTAGGCA | ATGATATTAC | CCAAAATGTA | 1140 |
| AAGGTAAAAT | CGAGTAATGT | GGATACTTCA | AAGCCAGGGG | AATATGAAGT | TGTATTTGAA | 1200 |
| GTGACAGATA | GCTTTGGTGG | AAAAGCAGAA | AAAGATTTCA | AGGTTACAGT | TTTAGGACAG | 1260 |
| CCAAGTATAG | AAGCGAATAA | TGTTGAATTA | GAAATAGATG | ATTCATTGGA | TCCATTAACA | 1320 |
| GATGCAAAAG | TAGGTCTCCG | TGCAAAGGAT | TCATTAGGTA | ATGATATTAC | GAAAGACATA | 1380 |
| AAAGTAAAGT | TCAATAACGT | AGATACTTCA | AATTCAGGAA | AGTATGAAGT | TATATTTGAA | 1440 |
| GTGACGGACC | GTTTTGGAAA | AAAAGCAGAA | AAAGTATTG | AAGTCCTTGT | TCTAGGAGAA | 1500 |
| CCAAGCATTG | AAGCAAATGA | TGTTGAGGTT | AATAAAGGTG | AAACGTTTGA | ACCATTAACA | 1560 |
| GATTCAAGAG | TTGGCCTCCG | TGCAAAAGAC | TCATTAGGTA | ATGATATTAC | GAAAGATGTG | 1620 |
| AAAATAAAAT | CAAGTAATGT | GGATACTTCA | AAACCAGGTG | AATATGAAGT | TGTATTTGAA | 1680 |
| GTGACAGATC | GTTTTGGTAA | ATATGTAGAA | AAACAATTG | GAGTTATAGT | GCCAGTAATT | 1740 |
| GATGATGAAT | GGGAAGATGG | AAATGTGAAT | GGTTGGAAAT | TCTATGCTGG | GCAAGATATT | 1800 |
| AAACTGTTGA | AGGATCCTGA | TAAAGCCTAT | AAAGGCGATT | ATGTATTCTA | TGATTCTAGA | 1860 |
| CACGTTGCTA | TTTCTAAAAC | AATTCCACTA | ACGGATTTGC | AAATAAATAC | AAACTATGAA | 1920 |

```
ATTACAGTGT ATGCTAAAGC AGAAAGCGGC GATCATCACT TAAAAGTGAC GTATAAGAAA    1980

GACCCGGCAG GTCCAGAAGA GCCGCCAGTT TTCAATAGAC TGATTAGCAC AGGCACATTG    2040

GTAGAAAAAG ATTATAGAGA ATTAAAGGG  ACGTTCCGCG TAACAGAATT AAACAAAGCA    2100

CCATTGATAA TCGTAGAGAA TTTTGGAGCT GGATATATAG GTGGAATTAG AATTGTGAAA    2160

ATATCGTAAT AA                                                        2172
```

( 2 ) INFORMATION FOR SEQ ID NO:51:

( i ) SEQUENCE CHARACTERISTICS:
        ( A ) LENGTH: 722 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

```
Met Lys Glu Gln Asn Leu Asn Lys Tyr Asp Glu Ile Thr Val Gln Ala
 1               5                  10                  15

Ala Ser Asp Tyr Ile Asp Ile Arg Pro Ile Phe Gln Thr Asn Gly Ser
             20                  25                  30

Ala Thr Phe Asn Ser Asn Thr Asn Ile Thr Thr Leu Thr Gln Ala Ile
         35                  40                  45

Asn Ser Gln Ala Gly Ala Ile Ala Gly Lys Thr Ala Leu Asp Met Arg
     50                  55                  60

His Asp Phe Thr Phe Arg Ala Asp Ile Phe Leu Gly Thr Lys Ser Asn
 65                  70                  75                  80

Gly Ala Asp Gly Ile Ala Ile Ala Phe His Arg Gly Ser Ile Gly Phe
                 85                  90                  95

Val Gly Thr Lys Gly Gly Gly Leu Gly Ile Leu Gly Ala Pro Lys Gly
            100                 105                 110

Ile Gly Phe Glu Leu Asp Thr Tyr Ala Asn Ala Pro Glu Asp Glu Val
        115                 120                 125

Gly Asp Ser Phe Gly His Gly Ala Met Lys Gly Ser Phe Pro Ser Phe
    130                 135                 140

Pro Asn Gly Tyr Pro His Ala Gly Phe Val Ser Thr Asp Lys Asn Ser
145                 150                 155                 160

Arg Trp Leu Ser Ala Leu Ala Gln Met Gln Arg Ile Ala Ala Pro Asn
                165                 170                 175

Gly Arg Trp Arg Arg Leu Glu Ile Arg Trp Asp Ala Arg Asn Lys Glu
            180                 185                 190

Leu Thr Ala Asn Leu Gln Asp Leu Thr Phe Asn Asp Ile Thr Val Gly
        195                 200                 205

Glu Lys Pro Arg Thr Pro Arg Thr Ala Thr Trp Arg Leu Val Asn Pro
    210                 215                 220

Ala Phe Glu Leu Asp Gln Lys Tyr Thr Phe Val Ile Gly Ser Ala Thr
225                 230                 235                 240

Gly Ala Ser Asn Asn Leu His Gln Ile Gly Ile Ile Glu Phe Asp Ala
                245                 250                 255

Tyr Phe Thr Lys Pro Thr Ile Glu Ala Asn Asn Val Asn Val Pro Val
            260                 265                 270

Gly Ala Thr Phe Asn Pro Lys Thr Tyr Pro Gly Ile Asn Leu Arg Ala
        275                 280                 285

Thr Asp Glu Ile Asp Gly Asp Leu Thr Ser Lys Ile Ile Val Lys Ala
    290                 295                 300
```

| | | | | | | | | | | | | | | |
|---|---|---|---|---|---|---|---|---|---|---|---|---|---|---|
| Asn | Asn | Val | Asn | Thr | Ser | Lys | Thr | Gly | Val | Tyr | Tyr | Val | Thr | Tyr | Tyr |
| 305 | | | | | 310 | | | | | 315 | | | | | 320 |
| Val | Glu | Asn | Ser | Tyr | Gly | Glu | Ser | Asp | Glu | Lys | Thr | Ile | Glu | Val | Thr |
| | | | | 325 | | | | | 330 | | | | | 335 | |
| Val | Phe | Ser | Asn | Pro | Thr | Ile | Ile | Ala | Ser | Asp | Val | Glu | Ile | Glu | Lys |
| | | | 340 | | | | | 345 | | | | | 350 | | |
| Gly | Glu | Ser | Phe | Asn | Pro | Leu | Thr | Asp | Ser | Arg | Val | Gly | Leu | Ser | Ala |
| | | 355 | | | | | 360 | | | | | 365 | | | |
| Gln | Asp | Ser | Leu | Gly | Asn | Asp | Ile | Thr | Gln | Asn | Val | Lys | Val | Lys | Ser |
| | 370 | | | | | 375 | | | | | 380 | | | | |
| Ser | Asn | Val | Asp | Thr | Ser | Lys | Pro | Gly | Glu | Tyr | Glu | Val | Val | Phe | Glu |
| 385 | | | | | 390 | | | | | 395 | | | | | 400 |
| Val | Thr | Asp | Ser | Phe | Gly | Gly | Lys | Ala | Glu | Lys | Asp | Phe | Lys | Val | Thr |
| | | | | 405 | | | | | 410 | | | | | 415 | |
| Val | Leu | Gly | Gln | Pro | Ser | Ile | Glu | Ala | Asn | Asn | Val | Glu | Leu | Glu | Ile |
| | | | 420 | | | | | 425 | | | | | 430 | | |
| Asp | Asp | Ser | Leu | Asp | Pro | Leu | Thr | Asp | Ala | Lys | Val | Gly | Leu | Arg | Ala |
| | | 435 | | | | | 440 | | | | | 445 | | | |
| Lys | Asp | Ser | Leu | Gly | Asn | Asp | Ile | Thr | Lys | Asp | Ile | Lys | Val | Lys | Phe |
| | 450 | | | | | 455 | | | | | 460 | | | | |
| Asn | Asn | Val | Asp | Thr | Ser | Asn | Ser | Gly | Lys | Tyr | Glu | Val | Ile | Phe | Glu |
| 465 | | | | | 470 | | | | | 475 | | | | | 480 |
| Val | Thr | Asp | Arg | Phe | Gly | Lys | Lys | Ala | Glu | Lys | Ser | Ile | Glu | Val | Leu |
| | | | | 485 | | | | | 490 | | | | | 495 | |
| Val | Leu | Gly | Glu | Pro | Ser | Ile | Glu | Ala | Asn | Asp | Val | Glu | Val | Asn | Lys |
| | | | 500 | | | | | 505 | | | | | 510 | | |
| Gly | Glu | Thr | Phe | Glu | Pro | Leu | Thr | Asp | Ser | Arg | Val | Gly | Leu | Arg | Ala |
| | | 515 | | | | | 520 | | | | | 525 | | | |
| Lys | Asp | Ser | Leu | Gly | Asn | Asp | Ile | Thr | Lys | Asp | Val | Lys | Ile | Lys | Ser |
| | 530 | | | | | 535 | | | | | 540 | | | | |
| Ser | Asn | Val | Asp | Thr | Ser | Lys | Pro | Gly | Glu | Tyr | Glu | Val | Val | Phe | Glu |
| 545 | | | | | 550 | | | | | 555 | | | | | 560 |
| Val | Thr | Asp | Arg | Phe | Gly | Lys | Tyr | Val | Glu | Lys | Thr | Ile | Gly | Val | Ile |
| | | | | 565 | | | | | 570 | | | | | 575 | |
| Val | Pro | Val | Ile | Asp | Asp | Glu | Trp | Glu | Asp | Gly | Asn | Val | Asn | Gly | Trp |
| | | | 580 | | | | | 585 | | | | | 590 | | |
| Lys | Phe | Tyr | Ala | Gly | Gln | Asp | Ile | Lys | Leu | Leu | Lys | Asp | Pro | Asp | Lys |
| | | | 595 | | | | | 600 | | | | | 605 | | |
| Ala | Tyr | Lys | Gly | Asp | Tyr | Val | Phe | Tyr | Asp | Ser | Arg | His | Val | Ala | Ile |
| | | 610 | | | | | 615 | | | | | 620 | | | |
| Ser | Lys | Thr | Ile | Pro | Leu | Thr | Asp | Leu | Gln | Ile | Asn | Thr | Asn | Tyr | Glu |
| 625 | | | | | 630 | | | | | 635 | | | | | 640 |
| Ile | Thr | Val | Tyr | Ala | Lys | Ala | Glu | Ser | Gly | Asp | His | His | Leu | Lys | Val |
| | | | | 645 | | | | | 650 | | | | | 655 | |
| Thr | Tyr | Lys | Lys | Asp | Pro | Ala | Gly | Pro | Glu | Glu | Pro | Pro | Val | Phe | Asn |
| | | | 660 | | | | | 665 | | | | | 670 | | |
| Arg | Leu | Ile | Ser | Thr | Gly | Thr | Leu | Val | Glu | Lys | Asp | Tyr | Arg | Glu | Leu |
| | | 675 | | | | | 680 | | | | | 685 | | | |
| Lys | Gly | Thr | Phe | Arg | Val | Thr | Glu | Leu | Asn | Lys | Ala | Pro | Leu | Ile | Ile |
| | 690 | | | | | 695 | | | | | 700 | | | | |
| Val | Glu | Asn | Phe | Gly | Ala | Gly | Tyr | Ile | Gly | Gly | Ile | Arg | Ile | Val | Lys |
| 705 | | | | | 710 | | | | | 715 | | | | | 720 |

Ile Ser

BACILLUS THURINGIENSIS TOXINS ACTIVE AGAINST HYMENOPTERAN PESTS

CROSS-REFERENCE TO A RELATED APPLICATION

This is a continuation-in-part of co-pending application Ser. No. 07/887,980, filed on May 22, 1992, now abandoned, which is a continuation-part of application Ser. No. 07/703,977, filed on May 22, 1991, now U.S. Pat. No. 5,260,058. This is also a continuation-in-part of application Ser. No. 07/797,645, filed on Nov. 25, 1991 now U.S. Pat. No. 5,268,297.

BACKGROUND OF THE INVENTION

The development of biological control agents as alternatives to chemical insecticides for the control of important pest species is a subject of increasing interest. Concerns for the environment and exposure of man to harmful substances in air, food and water have stimulated legislation and restrictions regarding the use of chemical pesticides, particularly for pests found in the urban environment. Control of insect pests in urban areas is highly desirable but exposure to chemical pesticides in the household and from lawns and gardens is of great concern to the public. If given a choice, most people would prefer to use a non-toxic biological control agent rather than a toxic chemical to control insects in the urban environment. The problem is that very few biological alternatives to chemical insecticides are available for purchase and use by the public.

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] TIBTECH 6:S4–S7). Thus, isolated B.t. endotoxin genes are becoming commercially valuable.

Until the last ten years, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystal called a δ-endotoxin which is toxic to the larvae of a number of lepidopteran insects.

In recent years, however, investigators have discovered B.t. pesticides with specificities for a much broader range of pests. For example, other species of B.t., namely *israelensis* and *tenebrionis* (a.k.a. B.t. M-7, a.k.a. *B.t. san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245-255). See also Couch, T. L. (1980) "Mosquito Pathogenicity of *Bacillus thuringiensis* var. *israelensis,*" *Developments in Industrial Microbiology* 22:61–76; Beegle, C. C., (1978) "Use of Entomogenous Bacteria in Agroecosystems," *Developments in Industrial Microbiology* 20:97-104. Krieg, A., A. M. Huger, G. A. Langenbruch, W. Schnetter (1983) Z aug. Ent. 96:500–508, describe *Bacillus thuringiensis* var. tenebrionis, which is reportedly active against two beetles in the order Coleoptera. These are the Colorado potato beetle, *Leptinotarsa decemlineata*, and *Agelastica alni*.

Recently, new subspecies of B.t. have been identified, and genes responsible for active δ-endotoxin proteins have been isolated (Höfte, H., H. R. Whiteley [1989] *Microbiological Reviews* 52(2):242–255). Höfte and Whiteley classified B.t. crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a B.t. crystal protein gene in *Escherichia coli* has been described in the published literature (Schnepf, H. E., H. R. Whitely [1981] *Proc. Natl. Acad. Sci. U.S.A.* 78:2893–2897). U.S. Pat. Nos. 4,448,885 and 4,467,036 both disclose the expression of B.t. crystal protein in *E. coli*. U.S. Pat. Nos. 4,797,276 and 4,853,331 disclose *B. thuringiensis* strain *san diego* (a.k.a. *B.t. tenebrionis*, a.k.a. M-7) which can be used to control coleopteran pests in various environments. U.S. Pat. No. 4,918,006 discloses B.t. toxins having activity against Dipterans. U.S. Pat. No. 4,849,217 discloses B.t. isolates which have activity against the alfalfa weevil. U.S. Pat. No. 5,208,077 discloses coleopteran-active *Bacillus thuringiensis* isolates. U.S. Pat. Nos. 5,151,363 and 4,948,734 disclose certain isolates of B.t. which have activity against nematodes. As a result of extensive research and investment of resources, other patents have issued for new B.t. isolates and new uses of B.t. isolates. However, the discovery of new B.t. isolates and new uses of known B.t. isolates remains an empirical, unpredictable art.

Ants comprise a large group of insects (family Formicidae) from the taxonomic order, Hymenoptera. They are among the most common house pests. In many situations, ants are a nuisance pest. Foraging ants create problems with hygiene in hospitals and the food industry. Ants also create problems in agriculture. Damage can be caused by direct feeding on plants. Harvester and fire ants are commonly associated with this type of damage (Holldobler, B., E. O. Wilson [1990] *The Ants*, Belkap Press, Cambridge, Mass. 732 pp.) Some ants cause indirect damage by nurturing and protecting sap feeding insects such as mealybugs and aphids. Ants, particularly in the genus Solenopsis are capable of producing extremely painful stings to humans. It has been estimated that approximately 10,000 stings occur each year (Habermehl, G. G. [1981] *Venomous Animals and Their Toxins*, Springer-Verlag, New York, 195 pp.). The pharaoh ant (*Monomorium pharaonis*) is primarily an urban pest. However, this species can also be an agricultural pest and damage to corn has been noted (Ebeling, W. [1978] *Urban Entomology*, UC Press, Berkeley, Calif., 695 pp.).

Carpenter ants, Camponotus spp., are distributed throughout Noah America. Some of the more common and/or studied species include C. modoc in the Pacific Northwest, C. clarithorax in southern California, and the black, red, and Florida carpenter ants, *C. pennsylvanicus, C. noveboracensis* and *C. abdominalis*, respectively, in the east (Ebeling, W. [1978] *Urban Entomology*, Univ. Calif.: Berkeley p. 209-213). Public concern over carpenter ants has been increasing due to the greater probability of structural infestations as suburban developments extend into the forest habitats of the ants.

Pestiferous species of carpenter ants may be considered nuisance pests because of their foraging activity inside homes. More significant damage occurs when carpenter ants extend their nests into sound wood. Nesting sites may be located in live and dead trees, sometimes resulting in damage to shade trees. Nests may also be established in walls and support beams of structures, or in voids within doors, walls, and furniture. Preference for moist or decaying wood has been reported, but nesting sites are not restricted to such areas. Carpenter ant populations develop relatively slowly with colonies of 300–2,000 workers being produced over a 2-year or longer period for various species. The presence of reproductives follows this slow development since their production has been reported only from well established colonies (Hansen, L. D., R. D. Akre [1985] Biology of carpenter ants in Washington state (Hymenoptera: Formicidae: Camponotus). Melanderia 43. 62 p.; Pricer, J. L. [1908] Biol. Bull. 14:177–218). Despite the slow colony growth, large colonies with satellite colonies have been found. Worker movement occurs between the main colony and the satellites, which serve as areas for further brood development and colony expansion (Hansen and Akre [1985], supra).

Current methods for controlling structural infestations of carpenter ants include sanitation of potential and current nest sites, minimizing access to structures (e.g. preventing the contact of tree branches with a structure), and the application of insecticides to repel (perimeter spray barriers) and/or eliminate carpenter ants. The use of boric acid dust in dry, wall voids is reported to be effective for up to 20 years (Hansen and Akre, supra).

Recommendations for the chemical control of established structural infestations in the home are often accompanied with warnings of possible hazards to the applicator as well as children and pets. Alternative control methods such as effective biological control agents have not been found (Akre, R. D., L. D. Hansen, A. L. Antonelli [1989] Ext. Bull. Washington State Univ. Coop. Ext. Serv. 1989 rev. no. EB 0818, 6 pp.). A need clearly exists for a safe, effective biological control agent for carpenter ants.

Pharaoh ants, *Monomorium pharaonis*, have been described as "... the most persistent and difficult of all our house-infesting ants to control or eradicate" (Smith, M. R. [1965] USDA-ARS Tech. Bull. No. 1326, 105 pp.). It is a tropical species which has extended its range to more temperate regions by establishing colonies in heated buildings. Pharaoh ants frequently infests buildings where food is prepared, and have been found to carry pathogenic organisms (Beatson, S. H. [1972] Lancet 1:425–427).

The difficulty in controlling pharaoh ants may be attributed to their inaccessible nesting sites, rapid population growth, and dispersion of colonies. Their small size allows establishment of colonies in any suitable location, including unusual places such as between books and in stored clothing. With multiple queen colonies, and the warm (30° C.), humid (63–80% RH) conditions that favor pharaoh ants, large colonies can develop rapidly. Portions of these large colonies may disperse to form new colonies at any time, probably in response to overcrowding and unfavorable microenvironmental conditions. Unlike other ant species, pharaoh ants do not exhibit intercolony aggression. This permits the adoption of ants from other colonies and may further enhance the establishment of new colonies and reinfestations. Pharaoh ants also forage for food more than 35 m from the nest without distinct trail following, and thus make nests difficult to find and eradicate.

Control methods for pharaoh ants emphasize the use of insect growth regulators (IGR) or toxicants incorporated into baits. Properly implemented bait programs are effective, however it may take over a month to achieve control. Insecticide applications, while fast acting, usually do not eliminate colonies, and may be unacceptable in certain areas where toxic residues are a concern. In addition, insecticide applications are generally not compatible with bait programs.

A need exists for safe and effective biological control agents for pharaoh ants.

SUMMARY OF THE INVENTION

The subject invention concerns novel Bacillus thuringiensis (B.t.) isolates and genes therefrom which encode novel hymenopteran-active proteins. The novel B.t. isolates, known herein as *Bacillus thuringiensis* PS140E2 (B.t. PS140E2), *Bacillus thuringiensis* PS86Q3 (B.t. PS86Q3) and *Bacillus thuringiensis* PS211B2(B.t. PS211B2), as well as toxins from these isolates, can be used to control pests such as fire ants, carpenter ants, argentine ants, and pharaoh ants.

The subject invention also includes mutants of the above isolates which have substantially the same pesticidal properties as the parent isolate. Procedures for making mutants are well known in the microbiological art. Ultraviolet light and nitrosoguanidine are used extensively toward this end.

The subject invention also concerns novel toms active against ants. A further aspect of the invention concerns genes encoding these formicidal toms. The subject invention provides the person skilled in this art with a vast array of formicidal toms, methods for using these toxins, and genes that encode the toms. The genes or gene fragments of the invention encode *Bacillus thuringiensis* δ-endotoxins which have hymenopteran activity. The genes or gene fragments can be transferred to suitable hosts via a recombinant DNA vector.

One aspect of the invention is the discovery of a generalized chemical formula common to a wide range of formicidal toxins. This formula can be used by those skilled in this art to obtain and identify a wide variety of toxins having the desired formicidal activity. The subject invention provides other teachings which enable the skilled practitioner to identify and isolate ant-active toxins and the genes which code therefor. For example, characteristic features of ant-active toxin crystals are disclosed herein. Furthermore, characteristic levels of amino acid homology can be used to characterize the toxins of the subject invention. Yet another characterizing feature pertains to immunoreactivity of the toxins with certain antibodies. Also, nucleotide probes specific for genes encoding toxins with formicidal activity are described. Thus, the identification of toxins of the subject invention can be accomplished by sequence-specific motifs, overall sequence similarity, immunoreactivity, and ability to hybridize with specific probes.

In addition to the teachings of the subject invention which broadly define B.t. toxins with advantageous formicidal activity, a further aspect of the subject invention is the provision of specific formicidal toxins and the nucleotide sequences which encode these toxins. Examples of such specific toxins are the gene expression products of isolate PS86Q3.

BRIEF DESCRIPTION OF THE DRAWINGS

FIG. 1 is a photograph of a standard SDS polyacrylamide gel of B.t. PS140E2, and B.t. PS86Q3.

Figure 2:
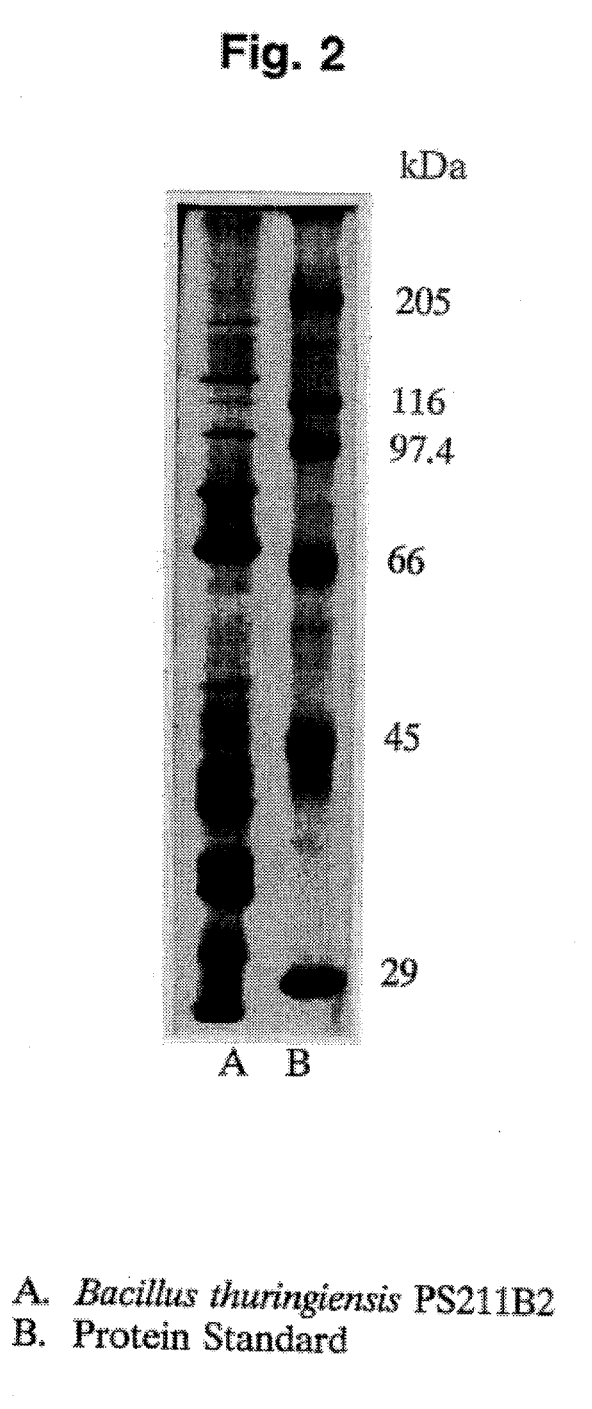

FIG. 2 is a photograph of a standard SDS polyacrylamide gel showing alkali-soluble proteins of B.t. PS211B2 compared to a protein standard.

FIG. 4 is B.t. PS86Q3; and FIG. 5 is B.t. PS211B2). Cells were embedded in an epoxy resin and stained with uranyl acetate and lead citrate.

BRIEF DESCRIPTION OF THE SEQUENCE

Figure 3:
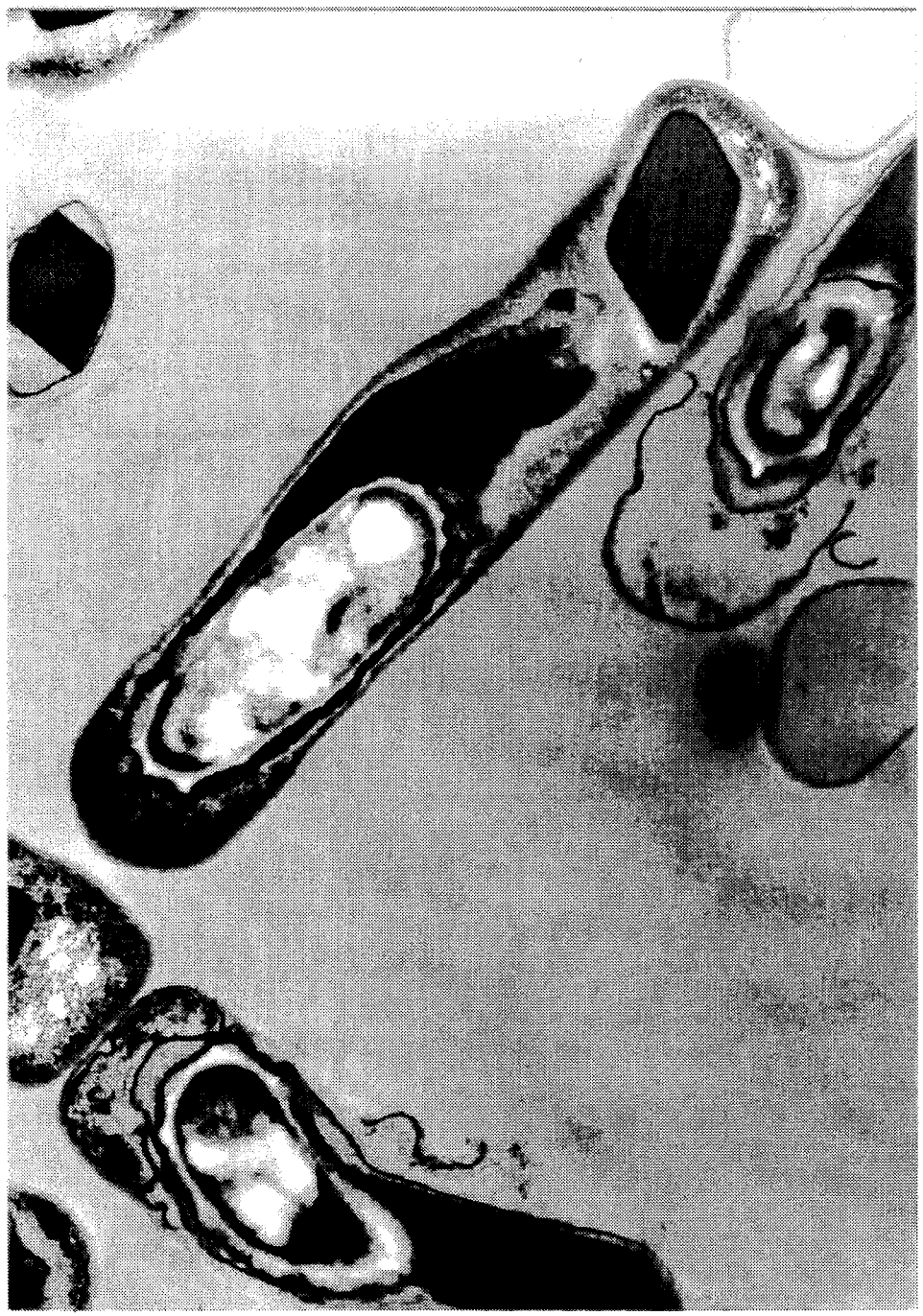
FIGS. 3–5 are transmission electron micrographs of ultrathin sections of the ant-active B.t. strains (FIG. 3 is B.t. PS140E2.

SEQ ID NO. 1 is the nucleotide sequence of gene 17a.
SEQ ID NO. 2 is the amino acid sequence of protein 17a.
SEQ ID NO. 3 is the nucleotide sequence of gene 17b.
SEQ ID NO. 4 is the amino acid sequence of protein 17b.
SEQ ID NO. 5 is the nucleotide sequence of gene 33F2.
SEQ ID NO. 6 is the amino acid sequence of protein 33F2.
SEQ ID NO. 7 is the nucleotide sequence of gene 86Q3a.
SEQ ID NO. 8 is the amino acid sequence of protein 86Q3a.
SEQ ID NO. 9 is the nucleotide sequence of gene 63B.
SEQ ID NO. 10 is the amino acid sequence of protein 63B.
SEQ ID NO. 11 is the amino acid sequence of a probe which can be used according to the subject invention.
SEQ ID NO. 12 is DNA coding for the amino acid sequence of SEQ ID NO. 11.
SEQ ID NO. 13 is DNA coding for the amino acid sequence of SEQ ID NO. 11.
SEQ ID NO. 14 is the amino acid sequence of a probe which can be used according to the subject invention.
SEQ ID NO. 15 is DNA coding for the amino acid sequence of SEQ ID NO. 14.
SEQ ID NO. 16 is DNA coding for the amino acid sequence of SEQ ID NO. 14.
SEQ ID NO. 17 is the N-terminal amino acid sequence of 17a.
SEQ ID NO. 18 is the N-terminal amino acid sequence of 17b.
SEQ ID NO. 19 is the N-terminal amino acid sequence of 86Q3a.
SEQ ID NO. 20 is the N-terminal amino acid sequence of 63B.
SEQ ID NO. 21 is the N-terminal amino acid sequence of 33F2.
SEQ ID NO. 22 is an internal amino acid sequence for 63B.
SEQ ID NO. 23 is a synthetic oligonucleotide derived from 17.
SEQ ID NO. 24 is the forward oligonucleotide primer from 63B.
SEQ ID NO. 25 is the reverse oligonucleotide primer from 63B.
SEQ ID NO. 26 is oligonucleotide probe 33F2A.
SEQ ID NO. 27 is oligonucleotide probe 33F2B.
SEQ ID NO. 28 is a reverse primer used according to the subject invention.
SEQ ID NO. 29 is an oligonucleotide derived from the N-terminal amino acid sequence of 86Q3a (SEQ ID NO. 19).
SEQ ID NO. 30 is the amino acid sequence coded for by an oligonucleotide used according to the subject invention (SEQ ID NO. 31).
SEQ ID NO. 31 is an oligonucleotide which codes for the amino acid sequence of SEQ ID NO. 30.
SEQ ID NO. 32 is the amino acid sequence coded for by the oligonucleotide of SEQ ID NO. 33.
SEQ ID NO. 33 is a DNA sequence coding for the peptide of SEQ ID NO. 32.
SEQ ID NO. 34 is the reverse complement primer to SEQ ID NO. 38, used according to the subject invention.
SEQ ID NO. 35 is a forward primer according to the subject invention.
SEQ ID NO. 36 is an amino acid sequence according to the subject invention.
SEQ ID NO. 37 is a reverse primer according to the subject invention.
SEQ ID NO. 38 is the nematode (NEMI) variant of region 5 of Höfte and Whiteley.
SEQ ID NO. 39 is the Generic Formula of the subject invention.
SEQ ID NO. 40 is an oligonucleotide derived from the N-terminal amino acid sequence of 86Q3c.
SEQ ID NO. 41 is the "protoxin T" oligonucleotide used as the reverse 3' primer.
SEQ ID NO. 42 is the nucleotide sequence of gene 86Q3c.
SEQ ID NO. 43 is the amino acid sequence of protein 86Q3c.
SEQ ID NO. 44 is the N-terminal amino acid sequence of 140E2.
SEQ ID NO. 45 is an oligonucleotide probe derived from the 35 kDa toxin of PS140E2.
SEQ ID NO. 46 is an internal amino acid sequence of 211B2.
SEQ ID NO. 47 is an N-terminal amino acid sequence of 211B2.
SEQ ID NO. 48 is a forward oligonucleotide primer used according to the subject invention.
SEQ ID NO. 49 is a reverse oligonucleotide primer used according to the subject invention.
SEQ ID NO. 50 is the nucleotide sequence of 211B2.
SEQ ID NO. 51 is the amino acid sequence of 211B2.

DETAILED DISCLOSURE OF THE INVENTION

One aspect of the subject invention is the discovery of *Bacillus thuringiensis* isolates having activity against ants.

A comparison of the characteristics of the *Bacillus thuringiensis* isolates of the subject invention is shown in Table 1.

TABLE 1

Comparison of B.t. PS140E2, B.t. PS86Q3, and B.t. PS211B2

| | B.t. PS140E2 | B.t. PS86Q3 | B.t. PS211B2 |
|---|---|---|---|
| Inclusions: | Ellipse and 2 small inclusions | 1 long and 1 or 2 small inclusions | Large amorphic |
| Approximate molecular wt. of proteins by SDS-PAGE | 78,000 70,000 35,000 | 155,000 135,000 98,000 62,000 58,000 | 175,000 130,000 100,000 83,000 69,000 43,000 40,000 36,000 35,000 34,000 27,000 |
| Host range Serovar | Hymenoptera 6, entomocidus | Hymenoptera new | Hymenoptera 6, entomocidus |

The toxin genes or gene fragments exemplified according to the subject invention can be obtained from *B. thuringiensis* (B.t.) isolates designated PS17, PS33F2, PS63B, PS140E2, PS211B2, and PS86Q3. Subcultures of the *E. coli* host harboring the toxin genes of the invention were deposited in the permanent collection of the Northern Research Laboratory, U.S. Department of Agriculture, Peoria, Ill., U.S.A. The accession numbers are as follows:

| Culture | Repository No. | Deposit Date |
| --- | --- | --- |
| B.t. PS140E2 | NRRL B-18812 | April 23, 1991 |
| B.t. PS86Q3 | NRRL B-18765 | February 6, 1991 |
| B.t. PS211B2 | NRRL B-18921 | November 15, 1991 |
| B.t. PS17 | NRRL B-18243 | July 28, 1987 |
| B.t. PS33F2 | NRRL B-18244 | July 28, 1987 |
| B.t. PS63B | NRRL B-18246 | July 28, 1987 |
| E. coli NM522(pMYC2316)(33F2) | NRRL B-18785 | March 15, 1991 |
| E. coli NM522(pMYC2321) | NRRL B-18770 | February 14, 1991 |
| E. coli NM522(pMYC2317) | NRRL B-18816 | April 24, 1991 |
| E. coli NM522(pMYC1627)(17a) | NRRL B-18651 | May 11, 1990 |
| E. coli NM522(pMYC1628)(17b) | NRRL B-18652 | May 11, 1990 |
| E. coli NM522(pMYC1642)(63B) | NRRL B-18961 | April 10, 1992 |
| E. coli MR618(pMYC1647)(86Q3a) | NRRL B-18970 | April 29, 1992 |
| E. coli NM625(pMYC1648)(86Q3c) | NRRL B-18992 | August 25, 1992 |
| E. coli NM522(pMYC2367)(140E2) | NRRL B-21149 | October 20, 1993 |
| E. coli NM522(pMYC2371)(211B2) | NRRL B-21150 | October 20, 1993 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

In addition to the hymenopteran-active B.t. isolates described herein, the subject invention concerns a vast array of B.t. δ-endotoxins having hymenopteran activity. In addition to having formicidal activity, the toxins of the subject invention will have one or more of the following characteristics:

1. An amino acid sequence according to the generic formula disclosed herein.
2. A high degree of amino acid homology with specific toxins disclosed herein.
3. A DNA sequence encoding the toxin wherein said sequence hybridizes with probes or genes disclosed herein.
4. A nucleotide sequence which can be amplified using primers disclosed herein.
5. A crystal toxin presentation as described herein.
6. Immunoreactivity to an antibody raised to a toxin disclosed herein.

Toxins and genes. The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

One aspect of the subject invention concerns the discovery of a generic chemical formula (hereinafter referred to as the Generic Formula; SEQ ID NO. 39) which can be used to identify toxins having activity against ants. This formula describes toxin proteins having molecular weights of about 130,000 daltons or more. The Generic Formula below covers those amino acids in the N-terminal region extending two amino acids past the invariant proline residue encountered at amino acid number 695 in the sequence of 86Q3a. The organization of the toxins within this class is delineated by the following generic sequence motif that is the ultimate determinant of structure and function.

```
  1 MOXLUEBYPx   BXYUBLXxxx   xxxxXXXXXX   XXXXXBXXxX   EXXXKXXXKX
    XxxxxxXJXX   XXBXXXXXXX   XXLXXXXXXX   XXLZBLZBxB   PXXXXXXXXX
101 XXBBXXBXXX   XXXXXXXXYX   xxLBXXBXXX   BXXBBXXXBX   XXXXXXXUXX
    BXZLUXXXXX   XXXOBXXXX*   XXXXxxxxxx   xxxxxxxxxX   XX*xxxxxxx
201 xxxxxXXUZX   XOXXLXXBxx   xxXEXXXXXx   xxxxxxxxXL   PXYOXBOXXH
    LBLXJXXLxx   xxxxxXKXXB   XXJXxBXXXK   XXLXXXLXXX   XLOBXXXBXX
301 XLXXXxZZZJ   xXZXXXXXXY   BJXBOXX*LE   BXXXXPOBEX   XXYXXxxxxx
    XLXXOKXLXZ   XxxxxxXXXX   BXXXXXZXXX   ZXXXXXXxXX   XXXBXXXXXX
401 XXXXBxxxxx   xxxxXXXXXX   LXXXXXXXXX   XXX*xxXXXX   XxXXXXXXXX
```

|     |           |           |            |            |            |
|-----|-----------|-----------|------------|------------|------------|
|     | XXZXUXXXBX | XXUXxxXX*X | XXXXXXXXXX | XXXXXXXxKX | ZXXXXXXXxx |
| 501 | xxxxxxXXXZ | Z*X*XXXXxx | xXXPXXxxxx | xxxxXXLXXL | YXXXXXXXJX |
|     | XXxXBXxBBZ | XXXXXEXXXX | XBXZXXXXXX | XBXXXXBXxx | xXXKxxxxxx |
| 601 | xxxxxxxxEX | LUZXUXBXLX | XXUXBXBXBX | XXXXXXYXBK | *KYOZXXXXX |
|     | XXBXBEXXXx | UXBXXXXXXX | ZXXXXXXZxx | XXXXXYXBXZ | XXxxxxxOx  |
| 701 | XLXxxxxxxx | xxXUXXXXBB | LEKLEBBPXX |            |            |

Numbering is for convenience and approximate location only.

Symbols used:

| A = ala | G = gly | M = met | S = ser |
|---------|---------|---------|---------|
| C = cys | H = his | N = asn | T = thr |
| D = asp | I = ile | P = pro | V = val |
| E = glu | K = lys | Q = gln | W = trp |
| F = phe | L = leu | R = arg | Y = tyr |

K = K or R
E = E or D
L = L or I
B = M, L, I, V, or F
J = K, R, E, or D
O = A or T
U = N or Q
Z = G or S
X = any naturally occurring amino acid, except C.
* = any naturally occurring amino acid.
x = any naturally occurring amino acid, except C (or complete omission of any amino acids).

Where a stretch of wild-card amino acids are encountered (X(n) or x(n) where n>2), repetition of a given amino acid should be avoided. Similarly, P, C, E, D, K, or R utilization should be minimized.

Further guidance for characterizing the formicidal toxins of the subject invention is provided in Tables 3 and 4, which demonstrate the relatedness among formicidal toxins. These tables show a numeric score for the best matching alignment between two proteins that reflects: (1) positive scores for exact matches, (2) positive or negative scores reflecting the likelihood (or not) of one amino acid substituting for another in a related protein, and (3) negative scores for the introduction of gaps. A protein sequence aligned to itself will have the highest possible score—i.e., all exact matches and no gaps. However, an unrelated protein or a randomly generated sequence will typically have a low positive score. Related sequences have scores between the random background score and the perfect match score.

The sequence comparisons were made using the local homology algorithm of Smith and Waterman ([1981] *Advances in Applied Mathematics* 2:482–489), implemented as the program "Bestfit" in the GCG Sequence Analysis Software Package Version 7 Apr. 1991. The sequences were compared with default parameter values (comparison table: Swgappep. Cmp, Gap weight:3.0, Length weight:0.1) except that gap limits of 250 residues were applied to each sequence compared. The program output value compared is referred to as the Quality score.

Tables 3 and 4 show the pairwise alignments between the indicated amino acids of the ant-active proteins and representatives of dipteran (CryIV; ISRH3 of Sen, K. et al. [1988] *Agdc. Biol. Chem.* 52:873–878), lepidopteran and dipteran (CryIIA; CryB1 of Widner and Whiteley [1989] *J. Bacteriol.* 171:965–974), and lepidopteran (CryIA(c); Adang et al. [1981] *Gene* 36:289–300) proteins.

Table 2 shows which amino acids were compared from the proteins of interest.

The N-terminal portions of the molecules consisting of about 600–700 amino acids were compared. As can be seen from Table 2, the amino acids compared started with amino acid 1 at the N-terminus and continued about 600–700 amino acids toward the C-terminus. The exact length of the sequence to be compared is readily determined using the alignment program referred to above which takes into account regions of homology including those which exist in the portion of the toxins 600–700 amino acids from the N-terminus.

TABLE 2

| Protein | Amino acids compared |
|---------|---------------------|
| 86Q3c   | 1-672 |
| 86Q3a   | 1-697 |
| 63B     | 1-692 |
| 33F2    | 1-618 |
| 17a     | 1-677 |
| 17b     | 1-678 |
| CryIV   | 1-633 |
| CryIIA  | 1-633 |
| CryIIIA | 1-644 |

Table 3 shows the scores prior to adjustment for random sequence scores.

TABLE 3

|         | 86Q3c | 86Q3a  | 63B   | 33F2  | 17b   | 17a    | CryIVA | CryIIA | CryIA(c) | CryIIIA |
|---------|-------|--------|-------|-------|-------|--------|--------|--------|----------|---------|
| 86Q3c   | 1008  | 357.0  | 339.1 | 321.7 | 975.5 | 974.6  | 233.5  | 238.2  | 232.4    | 248.4   |
| 86Q3a   |       | 1045.5 | 388.8 | 310.5 | 341.5 | 339.7  | 236.3  | 235.6  | 238.1    | 256.6   |
| 63B     |       |        | 1038  | 273.8 | 339.4 | 338    | 235.2  | 227.8  | 232.3    | 243.6   |
| 33F2    |       |        |       | 927   | 323   | 321.5  | 250.9  | 232.5  | 250.9    | 270.4   |
| 17b     |       |        |       |       | 1017  | 1007   | 238.3  | 240.4  | 236      | 248.4   |
| 17a     |       |        |       |       |       | 1015.5 | 239.6  | 240    | 236.6    | 248.9   |
| CryIVA  |       |        |       |       |       |        | 949.5  | 244.8  | 325.1    | 326.2   |
| CryIIA  |       |        |       |       |       |        |        | 949.5  | 243.6    | 241.3   |
| CryIA(c)|       |        |       |       |       |        |        |        | 913.5    | 366.6   |
| CryIIIA |       |        |       |       |       |        |        |        |          | 966     |

Note that ant-active protein 86Q3a is more closely related to 63B, 17a, 17b, and 33F2 than it is to the CryIVA, CryIIA, and CryIA(c) toxins.

Table 4 shows the same analysis after subtraction of the average score of 50 alignments of random shuffles of the column sequences with the row sequences.

TABLE 4

|      | 86Q3c | 86Q3a | 63B   | 33F2  | 17b   | 17a   | CryIVA | CryIIA | CryIA(c) | CryIIIA |
|------|-------|-------|-------|-------|-------|-------|--------|--------|----------|---------|
| 86Q3c | 803.5 | 155.8 | 133.5 | 128.7 | 769.0 | 767.6 | 39.2   | 42.6   | 43.3     | 53.8    |
| 86Q3a |       | 841   | 183.5 | 118.2 | 136.4 | 134.6 | 40.8   | 39.8   | 49.8     | 60.1    |
| 63B   |       |       | 830.8 | 81.2  | 132.9 | 129.2 | 39.3   | 33.2   | 43.3     | 48.7    |
| 33F2  |       |       |       | 739.3 | 129.7 | 128   | 65.4   | 50.1   | 70.9     | 84.2    |
| 17b   |       |       |       |       | 810.9 | 797.7 | 42.5   | 44.3   | 46.7     | 55.5    |
| 17a   |       |       |       |       |       | 808.3 | 42.8   | 43.7   | 44.5     | 53      |
| CryIVA |      |       |       |       |       |       | 760.6  | 54     | 141.1    | 141.1   |
| CryIIA |      |       |       |       |       |       |        | 755.4  | 54.7     | 51.2    |
| CryIA(c) |    |       |       |       |       |       |        |        | 728.8    | 182     |
| CryIIIA |     |       |       |       |       |       |        |        |          | 777.9   |

Note that in Table 4 the same relationship holds as in Table 3, i.e., 86Q3a's highest score, aside from itself, is with 63B.

This degree of relatedness provides the basis for using common or similar sequence elements from the previously-described known genes to obtain related, but non-identical genes from an ant-active isolate.

Thus, certain toxins according to the subject invention can be defined as those which have formicidal activity and have an alignment value (according to the procedures of Table 4) greater than 100 with 86Q3a. As used herein, the term "alignment value" refers to the scores obtained using the methods described above which were used to create the scores reported in Table 4.

The toxins of the subject invention can also be characterized in terms of the shape and location of toxin inclusions.

Inclusion type

PS86Q3—Long amorphic inclusion and a small inclusion, both of which remain with the spore after lysis. See FIG. 3.

Figure 4:

PS140E2—An elliptical coated inclusion situated outside the exospotium, and a long inclusion inside the exosporium. See FIG. 4.

Figure 5:

PS211B2—Large round amorphic inclusion with coat, and an elliptical inclusion. See FIG. 5.

Formicidal toxins according to the Generic Formula (SEQ ID NO. 39) of the subject invention are specifically exemplified herein by the toxin encoded by the gene designated 86Q3a. Since this toxin is merely exemplary of the toxins represented by the Generic Formula (SEQ ID NO. 39) presented herein, it should be readily apparent that the subject invention comprises all toxins conforming to the Generic Formula (SEQ ID NO. 39) and further comprises equivalents of those toxins (and nucleotide sequences coding for equivalent toxins) having the same or similar biological activity to ants. Equivalent toxins will have amino acid homology with the original toxin. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 5 provides a listing of examples of amino acids belonging to each class.

TABLE 5

| Class of Amino Acid | Examples of Amino Acids |
|---|---|
| Nonpolar | Ala, Vab Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin. The information presented in the Generic Formula of the subject invention provides clear guidance to the person skilled in this art in making various amino acid substitutions.

It should be apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toms, can readily be prepared using standard procedures in this art. The genes which encode these toxins can then be obtained from the microorganism. Therefore, included within the scope of the subject invention are toxins which immunoreact with (i.e., bind with) antibodies to the toxins exemplified herein.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Detection of the probe provides a means for determining in a known manner whether hybridization has occurred. Such a probe analysis provides a rapid method for identifying toxin-encoding genes of the subject invention.

The nucleotide segments which are used as probes according to the invention can be synthesized by use of DNA synthesizers using standard procedures. In the use of labeled nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Preferably, hybridization is conducted under stringent conditions by techniques well known in the art, as described, for example, in Keller, G. H., M. M. Manak (1989) *DNA Probes*, Stockton Press, New York, N.Y., pp. 169–170. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or perixodases, or the various chemfluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a probe of the present invention to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed test sequences can be readily prepared by methods which are well known to those skilled in the art. These variants can be used in the same manner as the instant probes so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

Specific nucleotide probes useful, according to the subject invention, in the rapid identification of ant-active genes are (i) DNA coding for a peptide sequence whose single letter amino acid designation is "REWINGAN" (SEQ ID NO. 11) or variations thereof which embody point mutations according to the following: position 1, R or K; position 3, W or Y; position 4, I or L; position 7, A or N; position 8, N or Q; a specific example of such a probe is "AGA(A or G)T(G or A)(G or T)(A or T)T(A or T)AATGG(A or T)GC(G or T)(A or C)A" (SEQ ID NO. 12); another example of such a probe is "GA(A or G)TGG(A or T)TAAATGGT(A or G)(A or C)(G or C)AA" (SEQ ID NO. 13);

(ii) DNA coding for a peptide sequence whose single letter amino acid designation is "PTFDPDLY" (SEQ ID NO. 14) or variations thereof which embody point mutations according to the following: position 3, F or L; position 4, D or Y; position 5, P or T; position 6, D or H; position 7, L or H or D or N; a specific example of such a probe is "CC(A or T)AC(C or T)TFT(T or G)ATCCAGAT(C or G)(T or A)(T or C)TAT" (SEQ ID NO. 15); another example of such a probe is "CC(T or A)AC(T or A)TT(T or C)GAT(C or A)CA(G or C)AT(C or A)(T or A)TTAT" (SEQ ID NO. 16);

(iii) additional useful probes for detecting ant-active B.t. genes include "GCAATTFFAA ATGAATTATA TCC" (SEQ ID NO. 23), "CAAYTACAAG CWCAACC" (SEQ ID NO. 24), "AATGAAGTWT ATCCWGTWAA T" (SEQ ID NO. 27), "GCAAGCGGCC GCTTATGGAA TAAATTCAAT TYKRTCWA" (SEQ ID NO. 28), "AGACTGGATC CATGGCWACW ATWAATGAAT TATAYCC" (SEQ ID NO. 29), "TAACGTGTAT WCGSTTTTAA TTTWGAYTC" (SEQ ID NO. 31), "TGGAATAAAT TCAATTYKRT CWA" (SEQ ID NO.

33), "AGGAACAAAY TCAAKWCGRT CTA" (SEQ ID NO. 34), and "TCTCCATCTT CTGARGWAAT" (SEQ ID NO. 37).

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the B.t. toxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser, E. T., Kezdy, F. J. [1984] *Science* 223:249–255). Thus, the subject invention includes mutants of the amino acid sequence depicted herein which do not alter the protein secondary structure, or if the structure is altered, the biological activity is substantially retained. Further, the invention also includes mutants of organisms hosting all or part of a toxin encoding a gene of the invention. Such microbial mutants can be made by techniques well known to persons skilled in the art. For example, UV irradiation can be used to prepare mutants of host organisms. Likewise, such mutants may include asporogenous host cells which also can be prepared by procedures well known in the art.

Recombinant hosts. The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae*, *Pseudomonas fluorescens*, *Serratia marcescens*, *Acetobacter xylinum*, *Agrobacterium tumefaciens*, *Rhodopseudomonas spheroides*, *Xanthomonas campestris*, *Rhizobium melioti*, *Alcaligenes entrophus*, and *Azotobacter vinlandii*; and phytosphere yeast species such as *Rhodotorula rubra*, *R. glutinis*, *R. marina*, *R. aurantiaca*, *Cryptococcus albidus*, *C. diffluens*, *C. laurentii*, *Saccharomyces rosei*, *S. pretoriensis*, *S. cerevisiae*, *Sporobolomyces roseus*, *S. odorus*, *Kluyveromyces veronae*, and *Aureobasidium pollulans*. Of particular interest are the pigmented microorganisms.

A wide variety of ways are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, B.t. or recombinant cells expressing a B.t. toxin can be treated to prolong the toxin activity and stabilize the cell for application to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores and crystals of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest, e.g., soil, foliage, or water, by spraying, dusting, sprinkling, or the like.

Mutants. Mutants of the isolates of the invention can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is placed in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Isolates of the Invention

A subculture of a B.t. isolate can be used to inoculate the following medium, a peptone, glucose, salts medium.

| Bacto Peptone | 7.5 g/l |
|---|---|
| Glucose | 1.0 g/l |
| $KH_2PO_4$ | 3.4 g/l |
| $K_2WO_4$ | 4.35 g/l |
| Salts Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

EXAMPLE 2

Purification of Protein and Amino Acid Sequencing

The B.t. isolates PS86Q3, PS17, PS63B, PS33F2, PS140E2, and PS211B2 were cultured as described in Example 1. The B.t. cells were harvested by standard sedimentation centrifugation. Parasporal inclusion bodies of some isolates were partially purified by sodium bromide (26–40%) isopycnic gradient centrifugation (Pfannenstiel, M. A., E. J. Ross, V. C. Kramer, K. W. Nickerson [1984] *FEMS Microbiol. Lett.* 21:39). Preparations containing proteins toxic to ants were bound to PVDF membranes (Millipore, Bedford, Me.) by western blotting techniques (Towbin, H., T. Staehlelin, K. Gordon [1979] *Proc. Natl. Acad. Sci. USA* 76:4350) and the N-terminal amino acid sequences were determined by the standard Edman reaction with an automated gas-phase sequenator (Hunkapiller, M. W., R. M. Hewick, W. L. Dreyer, and L. E. Hood [1983] *Meth. Enzymol.* 91:399). The sequences obtained were:

17a: A I L N E L Y P S V P Y N V (SEQ ID NO. 17)
17b: A I L N E L Y P S V P Y N V (SEQ ID NO. 18)
86Q3a: M A T I N E L Y P N V P Y N V L (SEQ ID NO. 19)
63B: Q L Q A Q P L I P Y N V L A (SEQ ID NO. 20)
33F2: A T L N E V Y P V N (SEQ ID NO. 21)
140E2: A N T T Q S F H F S N I L D Y K (SEQ ID NO. 44)
211B2: A A S D Y I D P I F (SEQ ID NO. 47)

Internal amino acid sequence data were derived for 63B and PS211B2. The toxin protein was partially digested with *Staphylococcus aureus* V8 protease (Sigma Chem. Co., St. Louis, Mass.) essentially as described (Cleveland, D. W., S. C. Fischer, M. W. Kirschner, U. K. Laemmli [1977] *J. Biol. Chem.* 252:1102). The digested material was blotted onto PVDF membrane and a ca. 28 kDa limit peptide was selected for N-terminal sequencing as described above. The sequence obtained was:

63B(2) V Q R I L D E K L S F Q L I K (SEQ ID NO. 22)

An internal amino acid sequence was also determined for 211B2 by in situ enzymatic cleavage of the electroblotted protein (Abersold, R. H., J. Leavitt, Saavedra, L. E. Hood, S. B. Kent [1987] *Proc. Natl. Acad. Sci. U.S.A.* 84:6970). From this sequence data oligonucleotide probes were synthesized on an Applied Biosystems, Inc. DNA synthesis machine. The sequence obtained was:

211B2: G I G F E L D T Y A N A P E D E V (SEQ ID NO. 46)

From these sequence data oligonucleotide probes were designed by utilizing a codon frequency table assembled from available sequence data of other B.t. toxin genes. The probes were synthesized on an Applied Biosystems, Inc. DNA synthesis machine.

Protein purification and subsequent amino acid analysis of the N-terminal peptides listed above has led to the deduction of several oligonucleotide probes for the isolation of toxin genes from formicidal B.t. isolates. RFLP analysis of restricted total cellular DNA using radiolabeled oligonucleotide probes has elucidated different genes or gene fragments.

EXAMPLE 3

Cloning of Toxin Genes from *Bacillus thuringiensis* Strain PS17 and Transformation into *Escherichia coli*

Total cellular DNA was prepared by growing the cells B.t. PS17 to a low optical density ($OD_{600}$=1.0) and recovering the cells by centrifugation. The cells were protoplasted in TES buffer (30 mM Tris-Cl, 10 mM EDTA, 50 mM NaCl, pH=8.0) containing 20 % sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride-ethidium bromide gradient.

Total cellular DNA from PS17 was digested with EcoRI and separated by electrophoresis on a 0.8% (w/v) Agarose-TAE (50 mM Tris-HCl, 20 mM NaOAc, 2.5 mM EDTA, pH=8.0) buffered gel. A Southern blot of the gel was hybridized with a [$^{32}$P]-radiolabeled oligonucleotide probe derived from the N-terminal amino acid sequence of purified 130 kDa protein from PS17. The sequence of the oligonucleotide synthesized is (GCAATTTFAAATGAAT-TATATCC) (SEQ ID NO. 3). Results showed that the hybridizing EcoRI fragments of PS17 are 5.0 kb, 4.5 kb, 2.7 kb and 1.8 kb in size, presumptively identifying at least four new ant-active toxin genes, 17d, 17b, 17a and 17e, respectively.

A library was constructed from PS17 total cellular DNA partially digested with Sau3A and size fractionated by electrophoresis. The 9 to 23 kb region of the gel was excised and the DNA was electroeluted and then concentrated using an Elutip™ ion exchange column (Schleicher and Schuel, Keene N.H.). The isolated Sau3A fragments were ligated into LambdaGEM-11™ (PROMEGA). The packaged phage were plated on KW251 *E. coli* cells (PROMEGA) at a high titer and screened using the above radiolabeled synthetic oligonucleotide as a nucleic acid hybridization probe. Hybridizing plaques were purified and rescreened at a lower plaque density. Single isolated purified plaques that hybridized with the probe were used to infect KW251 *E. coli* cells in liquid culture for preparation of phage for DNA isolation. DNA was isolated by standard procedures.

Recovered recombinant phage DNA was digested with EcoRI and separated by electrophoresis on a 0.8% agarose-TAE gel. The gel was Southern blotted and hybridized with the oligonucleotide probe to characterize the toxin genes isolated from the lambda library. Two patterns were present, clones containing the 4.5 kb (17b) or the 2.7 kb (17a) EcoRI fragments. Preparative amounts of phage DNA were digested with SalI (to release the inserted DNA from lambda arms) and separated by electrophoresis on a 0.6% agarose-TAE gel. The large fragments, electroeluted and concentrated as described above, were ligated to Sa/I-digested and dephosphorylated pBClac, an *E. coli*/B.t. shuttle vector comprised of replication origins from pBC16 and pUC19. The ligation mix was introduced by transformation into NM522 competent *E. coli* cells and plated on LB agar containing ampicillin, isopropyl-(Beta )-D-thiogalactoside (IPTG)and5-Bromo-4-Chloro-3-indolyl-(Beta )-D-galactoside (XGAL). White colonies, with putative insertions in the (Beta)-galactosidase gene of pBClac, were subjected to standard rapid plasmid purification procedures to isolate the desired plasmids. The selected plasmid containing the 2.7 kb EcoRI fragment was named pMYC1627 and the plasmid containing the 4.5 kb EcoRI fragment was called pMYC1628.

The toxin genes were sequenced by the standard Sanger dideoxy chain termination method using the synthetic oligonucleotide probe, disclosed above, and by "walking" with primers made to the sequence of the new toxin genes.

The PS17 toxin genes were subcloned into the shuttle vector pHT3101 (Lereclus, D. et al. [1989] *FEMS Micro-* biol. Lett. 60:211–218) using standard methods for expression in B.t. Briefly, SalI fragments containing the 17a and 17b toxin genes were isolated from pMYC1629 and pMYC1627, respectively, by preparative agarose gel electrophoresis, electroelution, and concentrated, as described above. These concentrated fragments were ligated into SalI-cleaved and dephosphorylated pHT3101. The ligation mixtures were used separately to transform frozen, competent *E. coli* NM522. Plasmids from each respective recombinant *E. coli* strain were prepared by alkaline lysis and analyzed by agarose gel electrophoresis. The resulting subclones, pMYC2311 and pMYC2309, harbored the 17a and 17b toxin genes, respectively. These plasmids were transformed into the acrystalliferous B.t. strain, HD-1 cryB (Aronson, A., Purdue University, West Lafayette, Ind.), by standard electroporation techniques (Instruction Manual, Biorad, Richmond, Calif.).

Recombinant B.t. strains HD-1 cryB [pMYC2311] and [pMYC2309] were grown to sporulation and the proteins purified by NaBr gradient centrifugation as described above for the wild-type B.t. proteins.

EXAMPLE 4

Molecular Cloning of a Gene Encoding a Toxin from *Bacillus thuringiensis* Strain PS63B Example 2 shows the aminoterminal and internal polypeptide sequences of the 63B toxin protein as determined by standard Edman protein sequencing. From these sequences, two oligonucleotide primers were designed using a codon frequency table assembled from B.t. genes encoding δ-endotoxins. The sequence of the forward primer (63B-A) was complementary to the predicted DNA sequence at the 5' end of the gene:

63B-A-5' CAA T/CTA CAA GCA/T CAA CC 3' (SEQ ID NO. 24)

The sequence of the reverse primer (63B-INT) was complementary to the inverse of the internal predicted DNA sequence:

63B-INT -5' TTC ATC TAA AAT TCT TTG A/TAC 3' (SEQ ID NO. 25)

These primers were used in standard polymerase chain reactions (Cetus Corporation) to amplify an approximately 460 bp fragment of the 63B toxin gene for use as a DNA cloning probe. Standard Southern blots of total cellular DNA from 63B were hybridized with the radiolabeled PCR probe. Hybridizing bands included an approximately 4.4 kbp XbaI fragment, an approximately 2.0 kbp HindIII fragment, and an approximately 6.4 kbp SpeI fragment.

Total cellular DNA was prepared from *Bacillus thuringiensis* (B.t.) cells grown to an optical density of 1.0 at 600 nm. The cells were recovered by centrifugation and protoplasts were prepared in lysis mix (300 mM sucrose, 25 mM Tris-HCl, 25 mM EDTA, pH =8.0) and lysozyme at a concentration of 20 mg/ml. The protoplasts were ruptured by addition of ten volumes of 0.1M NaCl, 0.1M Tris-HCl pH 8.0, and 0.1% SDS. The cellular material was quickly frozen at −70° C. and thawed to 37° C. twice. The supernatant was extracted twice with phenol/chloroform (1:1). The nucleic acids were precipitated with ethanol. To remove as much RNA as possible from the DNA preparation, RNase at final concentration of 200/dg/ml was added. After incubation at 37° C. for I hour, the solution was extracted once with phenol/chloroform and precipitated with ethanol.

A gene library was constructed from 63B total cellular DNA partially digested with NdeII and size fractioned by gel electrophoresis. The 9–23 kb region of the gel was excised and the DNA was electroeluted and then concentrated using an Elutip-d ion exchange column (Schleicher and Schuel, Keene, N.H.). The isolated NdeII fragments were ligated into BamHI-digested LambdaGEM-11 (PROMEGA). The packaged phage were plated on *E. coli* KW25 1 cells (PROMEGA) at a high titer and screened using the radiolabeled approximately 430 bp fragment probe amplified with the 63B-A and 63B internal primers (SEQ ID NOS. 27 and 28, respectively) by polymerase chain reaction. Hybridizing plaques were purified and rescreened at a lower plaque density. Single isolated, purified plaques that hybridized with the probe were used to infect KW25 1 cells in liquid culture for preparation of phage for DNA isolation. DNA was isolated by standard procedures (Maniatis, T., E. F. Fritsch, J. Sambrook [1982] *Molecular Cloning: A Laboratory Manual*, Cold Spring Harbor Laboratory, New York). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli*/B.t. shuttle vector comprised of pBlueScript S/K [Stratagene, San Diego, Calif.] and the replication origin from a resident B.t. plasmid [Lereclus, D. et al. (1989) *FEMS Microbial. Lett.* 60:211–218]). The ligation mix was introduced by transformation into competent *E. coli* NM522 cells (ATCC 47000) and plated on LB agar containing ampicillin (100 μg/ml), IPTG (2%), and XGAL (2%). White colonies, with putative restriction fragment insertions in the (Beta)-galactosidase gene of pHTBlueII, were subjected to standard rapid plasmid purification procedures (Maniatis et al., supra). Plasmids ere analyzed by SalI digestion and agarose gel electrophoresis. The desired plasmid construct, pMYC1641, contains an approximately 14 kb SalI insert.

For subcloning, preparative amounts of DNA were digested with XbaI and electrophoresed on an agarose gel. The approximately 4.4 kbp band containing the toxin gene was excised from the gel, electroeluted from the gel slice, and purified by ion exchange chromatography as above. This fragment was ligated into XbaI cut pHTBlueII and the resultant plasmid was designated pMYC1642.

EXAMPLE 5

Cloning of a Toxin Gene From B.t. PS33F2 and Transformation into *Escherichia coli*

Total cellular DNA was prepared from B.t. PS33F2 cells grown to an optical density, at 600 nm, of 1.0. Cells were pelleted by centrifugation and resuspended in protoplast buffer (20 mg/ml lysozyme in 0.3M sucrose, 25 mM Tris-Cl [pH 8.0], 25 mM EDTA). After incubation at 37° C. for I hour, protoplasts were lysed by the addition of nine volumes of a solution of 0.1M NaCl, 0.1% SDS, 0.1M Tris-Cl followed by two cycles of freezing and thawing. The cleared lysate was extracted twice with phenol:chloroform (1:1). Nucleic acids were precipitated with two volumes of ethanol and pelleted by centrifugation. The pellet was resuspended in 10 mM Tris-Cl, 1 mM EDTA (TE) and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE.

Plasmid DNA was extracted from protoplasts prepared as described above. Protoplasts were lysed by the addition of nine volumes of a solution of 10 mM Tris-Cl, 1 mM EDTA, 0.085 N NaOH, 0.1% SDS, pH=8.0. SDS was added to 1% final concentration to complete lysis. One-half volume of 3M KOAc was then added and the cellular material was precipitated overnight at 4° C. After centrifugation, the DNA was precipitated with ethanol and plasmids were purified by isopycnic centrifugation on cesium chloride-ethidium bromide gradients.

Restriction Fragment Length Polymorphism (RFLP) analyses were performed by standard hybridization of Southern blots of PS33F2 plasmid and total cellular DNA with $^{32}$P-labelled oligonucleotide probes designed to the N-terminal amino acid sequence disclosed in Example 2.

Probe 33F2A: 5'GCAFF ACAFF TTA AAT GAA GTA/T TAT 3'(SEQ ID NO. 26)

Probe 33F2B: 5'AAT GAA GTA/T TAT CCAfF GTA/T AAT 3'(SEQ ID NO. 27)

Hybridizing bands included an approximately 5.85 kbp EcoRI fragment. Probe 33F2A and a reverse PCR primer were used to amplify a DNA fragment of approximately 1.8 kbp for use as a hybridization probe for cloning the 33F2 toxin gene. The sequence of the reverse primer was:

5' GCAAGCGGCCGCTFATGGAATAAATTCAATT C/T T/G A/G TC T/A A 3' (SEQ ID NO. 28).

A gene library was constructed from 33F2 plasmid DNA digested with EcoRI. Restriction digests were fractionated by agarose gel electrophoresis. DNA fragments 4.3–6.6 kbp were excised from the gel, electroeluted from the gel slice, and recovered by ethanol precipitation after purification on an Elutip-D ion exchange column (Schleicher and Schuel, Keene N.H.). The EcoRI inserts were ligated into EcoRI-digested pHTBlueII (an E. coli/B. thudngiensis shuttle vector comprised of pBluescript S/K [Stratagene] and the replication origin from a resident B.t. plasmid (Lereclus et al., supra). The ligation mixture was transformed into frozen, competent NM522 cells (ATCC 47000). Transformants were plated on LB agar containing ampicillin, isopropyl-(Beta )-D-thiogalactoside (IPTG), and 5-bromo-4-chloro-3-indolyl-(Beta )-D-galactoside (XGAL). Colonies were screened by hybridization with the radiolabeled PCR amplified probe described above. Plasmids were purified from putative toxin gene clones by alkaline lysis and analyzed by agarose gel electrophoresis of restriction digests. The desired plasmid construct, pMYC2316, contains an approximately 5.85 kbp Eco4RI insert; the toxin gene residing on this DNA fragment (33F2a) is novel compared to the DNA sequences of other toxin genes encoding formicidal proteins.

Plasmid pMYC2316 was introduced into the acrystalliferous (Cry⁻) B.t. host, HD-1 CryB (A. Aronson, Purdue University, West Lafayette, Ind.) by electroporation. Expression of an approximately 120–140 kDa crystal protein was verified by SDS-PAGE analysis. Crystals were purified on NaBr gradients (Pfannenstiel et al., supra) for determination of toxicity of the cloned gene product to Pratylenchus spp.

EXAMPLE 6

Cloning of a Novel Toxin Gene from B.t. Isolate PS86Q3

Total cellular DNA was prepared from *Bacillus thuringiensis* (B.t.) cells as described in Example 5.

Total cellular DNA from isolate PS86Q3 was used as template for polymerase chain reaction (PCR) analysis according to protocols furnished by Perkin Elmer Cetus. An oligonucleotide derived from the N-terminal amino acid sequence of the toxin protein was used as a 5' primer. The sequence of this oligonucleotide is:

5'-AGACFGGATCCATGGC(A or T)AC(A or T)AT(A or T)AAT-GAATTATA(T or C)CC-3' (SEQ ID NO. 29).

An oligonucleotide coding for the amino acid sequence "ESKLKPNTRY" (SEQ ID NO. 30) can be used as the reverse 3' primer. The sequence of this oligonucleotide can be: "5'-TAACGTGTAT(A or T)CG(C or G)TTTTAATTT(T or A)GA(C or T)TC-3'" (SEQ ID NO. 31).

The reverse "YIDKIEFIP" (SEQ ID NO. 32) oligonucleotide was also used as a reverse 3' primer in conjunction with the above mentioned 5' primer. The sequence of the reverse primer can be: "5'-TGGAATAAATFCAATT(C or T)(T or G)(A or G)TC(T or A)A-3'" (SEQ ID NO. 33).

Amplification with the 5' primer and SEQ ID NO. 31 generates an approximately 2.3 kbp DNA fragment and an approximately 4.3 kbp DNA fragment. Amplification with the 5' primer and SEQ ID NO. 33 generates an approximate 1.8 kbp DNA fragment and an approximately 3.7 kbp DNA fragment. The approximately 2.3 kbp fragment was radiolabeled with $^{32}$P and used as a hybridization probe to generate restriction fragment polymorphism (RFLP) patterns and to screen recombinant phage libraries.

A Southern blot of total cellular DNA digested with EcoRV was probed with the radiolabeled 2.3 kbp probe described above. The resultant RFLP includes 9.5 kbp, 6.4 kbp, and 4.5 kbp hybridizing fragments.

A gene library was constructed from PS86Q3 total cellular DNA partially digested with NdeII and size fractioned by gel electrophoresis. The 9–23 kb region of the gel was excised and the DNA was electroeluted and then concentrated using an Elutip-d ion exchange column (Schleicher and Schuel, Keene, N.H.). The isolated NdeII fragments were ligated into BamHI-digested LambdaGEM-11 (PROMECA). The packaged phage were plated on E. coli KW25 1 cells (PROMECA) at a high titer and screened using the radiolabeled probe described above. Hybridizing plaques were purified and rescreened at a lower plaque density. Single isolated, purified plaques that hybridized with the probe were used to infect KW251 cells in liquid culture for preparation of phage for DNA isolation. DNA was isolated by standard procedures (Maniatis et al., supra). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an E. coli/B.t. shuttle vector comprised of pBluescript S/K [Stratagene, San Diego, Calif.]) and the replication origin from a resident B.t. plasmid (Lereclus et al. [1989], supra). The ligation mix was introduced by transformation into competent E. coli NM522 cells (ATCC 47000) and plated on LB agar containing ampicillin, IPTG, and XGAL. White colonies, with putative restriction fragment insertions in the (Beta)-galactosidase gene of pHTBlueII, were subjected to standard rapid plasmid purification procedures (Maniatis et al., supra). Plasmid DNA was analyzed by SalI digestion and agarose gel electrophoresis. The desired plasmid construct, pMYC1647, contains an approximately 12 kb SalI insert.

Plasmid pMYC1647 was introduced by electroporation into an acrystalliferous (Cry⁻) B.t., HD-1 CryB (A. I.

Aronson, Purdue University) host to yield MR515, a recombinant B.t. clone of 86Q3a. Expression of an approximately 155 kDa protein was verified by SDS-PAGE. Spores and crystals were removed from broth cultures and were used for determination of toxicity to pharaoh ants.

EXAMPLE 7

Cloning of a Second Novel Toxin Gene from B.t. Isolate PS8Q603

Total cellular DNA was prepared from *Bacillus thuringiensis* (B.t.) cells grown to an optical density of 1.0 at 600 rim. The cells were recovered by centrifugation and protoplasts were prepared in lysis mix (300 mM sucrose, 25 mM Tris-HCl, 25 mM EDTA, pH=8.0) and lysozyme at a concentration of 20 mg/ml. The protoplasts were ruptured by addition of ten volumes of 1% SDS. The cellular material was quickly frozen at −70° C. and thawed to 37° C. twice. The supernate was extracted twice with phenol/chloroform (1:1). The nucleic acids were precipitated with ethanol. In order to remove as much RNA as possible from the DNA preparation, RNase at final concentration of 200 μdg/ml was added and followed by phenol/chloroform extraction and ethanol precipitation.

Total cellular DNA from isolate PS86Q3 was used as template for polymerase chain reaction (PCR) analysis according to protocols furnished by Perkin Elmer Cetus. An oligonucleotide derived from the N-terminal amino acid sequence of the 135 kDa and 155 kDa proteins was used as a 5' primer. The sequence of this oligo is: 5'-AGACTG-GATCC ATG GC(A or T) AC(A or T) AT(A or T) AAT GAA TTA TA(T or C) CC-3' (SEQ ID NO. 40). The "protoxin T" oligonucleotide (SEQ ID NO. 41) was used as the reverse 3' primer. The sequence of this oligo is: 5'-GACTGCGGCC GCGTCGAC TrA ACG TGT AT(A or T) CG(C or G) TTT TAA TTT (T or A)GA (C or T)TC-3'.

Amplification with these two primers generated an approxximately 2.3 kbp DNA fragment. This fragment was then used as a hybridization probe. A Southern blot of 86Q3 total DNA digested with EcoRV and fractionated by electrophoresis on 0.8 (w/v) agarose-TAE buffered gel showed hybridizing fragments of approximately 6.4 kb and approximately 4.8 kb.

A library was constructed from PS86Q3 total cellular DNA as described in Example 6. The procedure varied from that used in Example 6 in that restriction enzyme XhoI was used to digest the DNA instead of SalI. The desired plasmid construct, pMYC1648, includes an approximately 14 kbp XhoI insert which contains the 86Q3c gene. Sequence analysis of the toxin gene revealed that it encodes a protein of approximately 134.5 kDa, deduced from the DNA sequence. The nucleotide and deduced amino acid sequences are shown in SEQ ID NOS. 42 and 43, respectively.

Plasmid pMYC1648 was introduced into an acrystalliferous (Cry⁻) B.t., HD-1 Cry B (A. I. Aronson, Purdue University), host by electroporation. Expression of an approximately 155 kDa protein was verified by SDS-PAGE. Broth containing spores and crystals was used for determination of toxicity to pharaoh ants (*Monomorium phraonis*).

EXAMPLE 8

Molecular Cloning and Expression of a Novel Toxin Gene from *Bacillus thuringiensis* Strain PS140E2

Total cellular DNA was prepared from *Bacillus thuringiensis* (B.t.) cells as described in Example 5. A gene library was constructed from PS1402 DNA partially digested with NdeII. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW25 1 cells. Plaques were screened by hybridization to an oligonucleotide probe deduced from the amino acid sequence of the PS140E2 35 kDa toxin. The sequence of this probe was:

5' TTT CAT TTT TC(A/T) AAT ATT TTA GAT TAT AAA 3' (SEQ ID NO. 45).

Hybridizing phage were plaque-purified and used to infect liquid cultures of *E. coli* KW25 1 cells for isolation of DNA by standard procedures (Maniatis et al., supra).

For subcloning the gene encoding the approximately 35 kDa PS140E2 toxin, preparative amounts of phage DNA were digested with SalI and electrophoresed on an agarose gel. The approximately 13.5 kbp band containing the toxin gene was excised from the gel, electroeluted from the gel slice, and purified by ion exchange chromatography as described above. The purified DNA insert was ligated into XhoI-digested pHTBlueII (an *E. coli/B. thuringiensis* shuttle vector comprised of pBluescript S/K [Stratagene, La Jolla, Calif.] and the replication origin from a resident B.t. plasmid [Lereclus et al. (1989) FEMS Microbiology Letters 60:211–218] ). The ligation mix was used to transform frozen, competent *E. coli* NM522 cells (ATCC 47000). β-galactosidase negative transformants were screened by restriction digestion of alkaline lysate plasmid minipreps as above. The desired plasmid construct, pMYC2367, contains a toxin gene thin is novel compared to other toxin genes containing insecticidal proteins.

pMYC2367 was introduced into the acrystalliferous (Cry⁻) B.t. host, CryB (A. Aronson, Purdue University, West Lafayette, Ind.), by electroporation. Expression of the 35 kDa toxin was demonstrated by SDS-PAGE analysis.

EXAMPLE 9

Molecular Cloning and Expression of a Novel Toxin Gene from *Bacillus thudngiensis* Strain PS211B2

Total cellular DNA was prepared from *Bacillus thudngiensis* (B.t.) cells as described in Example 5.

An approximately 300 bp-sized fragment of the novel toxin gene (estimated size: 80 kDa) was obtained by polymerase chain reaction (PCR) amplification from PS211B2 cellular DNA using the following primers: "Forward": 5' GCAGGATCCGATTATATT (TA) GATAT (TA) A (CGA) TCC 3' (SEQ ID NO. 48), and "Reverse": 5' GCG GCC GCA CTT CAT CTT C(TA)G G(TA)G CAT T(TA)G CAT A(TA)G TAT C 3' (SEQ ID NO. 49). This DNA fragment was cloned into pBluescript II SK- (Stratagene, La Jolla, CA) and the DNA sequence determined by dideoxynucleotide sequencing methodology (Sanger et al. [1977] *Proc. Natl. Acad. Sci. USA* 74:5463–5467) using Sequenase (US Biochemical, Cleveland, Ohio). This fragment was subsequently radiolabelled with ³²P and used as a probe in standard hybridization screens of recombinant phage libraries.

A gene library was constructed from PS211B2 DNA partially digested with NdeII. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW25 1 (Promega, Madison, Wis.) cells. Plaques were screened by hybridization with the probe described above. Hybridizing phage were plaque-purified and used to infect liquid cultures of *E. coli* KW251 cells for isolation of DNA by standard procedures (Maniatis et al., supra).

For subcloning the gene, preparative amounts of phage DNA were digested with SalI. The approximately 16 kbp band was ligated into XhoI-digested pHTBlueII (an *E. coli/B. thuringiensis* shuttle vector composed of pBluescript II SK- [Stratagene, La Jolla, Calif.] and the replication origin from a resident B.t. plasmid [Lereclus et al., supra]). The ligation mix was used to transform frozen, competent *E. coli* NM522 cells (ATCC 47000). β-galactosidase- transformants were screened by restriction digestion of alkaline lysate plasmid minipreps as above. The desired plasmid construct, pMYC2371, contains a toxin gene that is novel compared to other toxin genes containing insecticidal proteins. Sequence analysis of the toxin gene revealed that it encodes a protein of approximately 80,000 daltons, deduced from the DNA sequence. The nucleotide and deduced amino acid sequences are shown in SEQ ID NOS. 50 and 51, respectively.

pMYC2371 was introduced into the acrystalliferous (Cry⁻) B.t. host, CryB (A. Aronson, Purdue University, West Lafayette, Ind.), by electroporation. Expression of the approximately 80 kDa toxin was demonstrated by SDS-PAGE analysis.

EXAMPLE 10

Activity of the B.t. Toxin Protein and Gene Product Against Ants

Broths were tested for the presence of fi-exotoxin by a larval house fly bioassay (Campbell, D. P., Dieball, D. E., Bracket, J. M. [1987] "Rapid HPLC assay for the β-exotoxin of *Bacillus thuringiensis*," *J. Agric. Food Chem.* 35:156–158). Only isolates which tested free of β-exotoxin were used in the assays against ants.

A bait was made consisting of 10% *Bacillus thuringiensis* isolates of the invention and Crosse and Blackwell mint apple jelly. Approximately 100 ants were placed in each plastic test chamber replicate with the baits. Control experiments were performed with untreated mint apple jelly. Each test was replicated a minimum of 10 times. Mortality was assessed at 21 days after introduction of the bait to the ants. Results are shown below:

TABLE 6

Toxicity of *B. thuringiensis* isolates to the pharaoh ant (*Monomorium pharaonis*)

| B.t. Isolate | Percent Mortality |
|---|---|
| PS140E2 | 91 |
| PS 86Q3 | 84 |
| Control | 11 |

TABLE 6-continued

Toxicity of *B. thuringiensis* isolates to the pharaoh ant (*Monomorium pharaonis*)

| B.t. Isolate | Percent Mortality |
|---|---|
| PS211B2 | 90.0 |
| Control | 3.8 |

EXAMPLE 11

Activity of the B.t. Toxin Protein and Gene Product Against Ants

Honey buffered with phosphate at pH 6.5 containing B.t. was fed to 5 replicates of approximately 100 worker ants for 21 days. Ants were provided water ad libitum. Totoal mortality (in %) over the test period was compared to controls.

TABLE 7

Three week mortality (%) on pharaoh ant workers

| Sample | % toxin in final bait | % mortality |
|---|---|---|
| PS86Q3 | 20 | 100 |
| Honey only control | — | 16 |
| PS211B2 | 5 | 100 |
| PS140E2 | 10 | 98 |
| Control rearing diet | — | 61 |

EXAMPLE 12

Cloning of Novel Ant-Active Genes Using Generic Oligonucleotide Primers

The formicidal gene of a new formicidal B.t. can be obtained from DNA of the strain by performing the standard polymerase chain reaction procedure as in Example 6 using the oligonucleotides of SEQ ID NO. 33 or AGGAACAAAY-TCAAKWCGRTCTA (SEQ ID NO. 34) as reverse primers and SEQ ID NO. 12, SEQ ID NO. 13, SEQ ID NO. 15, SEQ ID NO. 16, SEQ ID NO. 23, SEQ ID NO. 27, SEQ ID NO. 29, or SEQ ID NO. 24 as forward primers. The expected PCR fragments would be approximately 330 to 600 bp with either reverse primer and SEQ ID NO. 12 or SEQ ID NO. 13, 1000 to 1400 bp with either reverse primer and SEQ ID NO. 15 or SEQ ID NO. 16, and 1800 to 2100 bp with either reverse primer and any of the three N-terminal primers, SEQ ID NO. 27, SEQ ID NO. 23, SEQ ID NO. 29, and SEQ ID NO. 24. Alternatively, a complement from the primer family described by SEQ ID NO. 12 and SEQ ID NO. 13 can be used as reverse primer with SEQ ID NO. 15, SEQ ID NO. 16, SEQ ID NO. 23, SEQ ID NO. 27, SEQ ID NO. 29, or SEQ ID NO. 24 as forward pruners. The expected PCR fragments would be approximately 650 to 1000 bp with SEQ ID NO. 15 or SEQ ID NO. 16, and 1400 to 1800 bp for the four N-terminal primers (SEQ ID NO. 27, SEQ ID NO. 23, SEQ ID NO. 29, and SEQ ID NO. 24).

As another alternative, the reverse primer SEQ ID NO. 31 can be used with any of the four N-terminal forward primers to yield fragments of approximately 2550–3100 bp; 1750–2150 bp with the forward primers SEQ ID NOS. 15 or 16; 850–1400 bp with SEQ ID NOS. 12 or 13; and 550–1050 bp with the forward primer (TFTAGATCGT(A or C)TTGA(G or A)TTT(A or G)T(A or T)CC (SEQ ID NO. 35).

As yet another alternative, the ITSED (SEQ ID NO 36) reverse primer (TCTCCATCTTCTGA(G or A)G(T or A)AAT) (SEQ ID NO. 37) can be used with the N-terminal forward primers (SEQ ID NO. 23, SEQ ID NO. 24, SEQ ID NO. 27, and SEQ ID NO. 29) to yield fragments of approximately 3550–4050 bp; 2600–3100 bp with forward primers SEQ ID NOS. 15 or 16; 1800–2400 bp with forward primers SEQ ID NOS. 12 or 13; and 1500–2050 bp with forward primer SEQ ID NO. 35.

Amplified DNA fragments of the indicated sizes can be radiolabeled and used as probes to clone the entire gene as in Example 6.

EXAMPLE 13

Insertion of Toxin Gene Into Plants

One aspect of the subject invention is the transformation of plants with genes coding for a formicidal toxin. The transformed plants are resistant to attack by ants.

Genes encoding formicidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUG series, M13mp series, pACYC184, etc. Accordingly, the sequence encoding the B.t. toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) EMBO J. 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a inker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. Also, advantageously, plants encoding a truncated toxin will be used. The truncated toxin typically will encode about 55% to about 80% of the full length toxin. Methods for creating synthetic B.t. genes for use in plants are known in the art.

EXAMPLE 14

Cloning of Novel *B. thuringiensis* Genes Into Insect Viruses

A number of viruses are known to infect insects. These viruses include, for example, baculoviruses and entomopoxviruses. In one embodiment of the subject invention, ant-active genes, as described herein, can be placed with the genome of the insect virus, thus enhancing the pathogenicity of the virus. Methods for constructing insect viruses which comprise B.t. toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 71:1535–1544) and Martens et al. (Martens, J. W. M., G. Honee, D. Zuidema, J. W. M. van Lent, B. Visser, J. M. Vlak (1990) *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A *Bacillus thuringiensis* toxin from isolate PS86Q3 which has activity against hymenopteran pests.

* * * * *

UNITED STATES PATENT AND TRADEMARK OFFICE
CERTIFICATE OF CORRECTION

PATENT NO. : 5,596,071
DATED : January 21, 1997
INVENTOR(S) : Jewel M. Payne, et al.

It is certified that error appears in the above-indentified patent and that said Letters Patent is hereby corrected as shown below:

Column 2, line 4: "Z aug. Ent." should read --*Z. ang. Ent.*--;

line 61: "Noah America" should read --North America--;

line 15: "CryIII" should read --CryIII--.

Column 4, line 32: "novel toms active" should read --novel toxins active--;

line 34: "formicidal toms. The" should read --formicidal toxins. The--;

line 36: "formicidal toms, methods" should read --formicidal toxins, methods--;

line 37: "encode the toms." should read --encode the toxins.--.

UNITED STATES PATENT AND TRADEMARK OFFICE
CERTIFICATE OF CORRECTION

PATENT NO. : 5,596,071  
DATED : January 21, 1997  
INVENTOR(S) : Jewel M. Payne, et al.

Page 2 of 8

It is certified that error appears in the above-indentified patent and that said Letters Patent is hereby corrected as shown below:

<u>Columns 7&8, bottom of page and Columns 9&10 top of page</u>:

"1    MOX<u>L</u>UEBYPx    BXYUB<u>L</u>Xxxx    xxxxXXXXXX    xxxxxbxxXx    <u>E</u>XXX<u>K</u>XXX<u>K</u>X XxxxxxXJXX    XXBXXXXXXX    XX<u>L</u>XXXXXXX    XX<u>L</u>ZB<u>L</u>ZBxB    PXXXXXXXXX 101   XXBBXXBXXX    XXXXXXXXYX    xx<u>L</u>BXXBXXX    BXXBBXXXBX    XXXXXXXUXX BXZ<u>L</u>UXXXXX    XXXOBXXXX*    XXXXxxxxxx    xxxxxxxxxX    xx*xxxxxxx 201   xxxxxXXUZX    XOXX<u>L</u>XXBxx    xx<u>E</u>XXXXXx    xxxxxxxxX<u>L</u>    PXYOXBOXXH <u>L</u>B<u>L</u>XJXX<u>L</u>xx    xxxxxX<u>K</u>XXB    XXJXxBXXX<u>K</u>    XX<u>L</u>XXX<u>L</u>XXX    X<u>L</u>OBXXXBXX 301   X<u>L</u>XXXxZZZJ    xXZXXXXXXY    BJXBOXX*<u>L</u>E    BXXXXPOB<u>E</u>X    XXYXXxxxxx X<u>L</u>XXO<u>K</u>X<u>L</u>XZ    XxxxxxXXXX    BXXXXXZXXX    ZXXXXXXxXX    XXXBXXXXXX 401   XXXXBxxxxx    xxxxXXXXXX    <u>L</u>XXXXXXXXX    XXX*xxXXXX    XxXXXXXXXX XXZXUXXXBX    XXUXxxXX*X    XXXXXXXXXX    XXXXXXXx<u>K</u>X    ZXXXXXXXxx 501   xxxxxxXXXZ    Z*X*XXXXxx    xXXPXXxxxx    xxxxXX<u>L</u>XX<u>L</u>    YXXXXXXXJX XxxXBXxBBZ    XXXXX<u>E</u>XXXX    XBXZXXXXXX    XBXXXXBXxx    xXX<u>K</u>xxxxxx 601   xxxxxxxx<u>E</u>X    <u>L</u>UZXUXBX<u>L</u>X    XXUXBXBXBX    XXXXXXYXB<u>K</u>    *<u>K</u>YOZXXXXX XXBXB<u>E</u>XXXx    UXBXXXXXXX    ZXXXXXXZxx    XXXXXYXBXZ    XxxxxxxxOx 701   X<u>L</u>Xxxxxxxx    xxXUXXXXBB    <u>LEKL</u>BBPXX " should read

UNITED STATES PATENT AND TRADEMARK OFFICE
CERTIFICATE OF CORRECTION

PATENT NO. : 5,596,071       Page 3 of 8
DATED : January 21, 1997
INVENTOR(S) : Jewel M. Payne, et al.

It is certified that error appears in the above-indentified patent and that said Letters Patent is hereby corrected as shown below:

```
--1   MOXLUEBYPx    BXYUBLXxxx    xxxxXXXXXX    XXXXXBXXxX    EXXXKXXXKX
      XxxxxxXJXX    XXBXXXXXXX    XXLXXXXXXX    XXLZBLZBxB    PXXXXXXXXX
101   XXBBXXBXXX    XXXXXXXXKX    xxLBXXBXXX    BXXBBXXXBX    XXXXXXXUXX
      BXZLUXXXXX    XXXOBXXXX*    XXXXxxxxxx    xxxxxxxxxX    XX*xxxxxxx
201   xxxxxXXUZX    XOXXLXXBxx    xxXEXXXXXx    xxxxxxxxXL    PXYOXBOXXH
      LBLXJXXLxx    xxxxxXKXXB    XXJXxBXXXK    XXLXXXLXXX    XLOBXXXBXX
301   XLXXXxXXXJ    xXZXXXXXXY    BJXBOXX*LE    BXXXXPOBEX    XXYXXxxxxx
      XLXXOKXLXZ    XxxxxxXXXX    BXXXXXZXXX    ZXXXXXXxXX    XXXBXXXXXX
401   XXXXBxxxxx    xxxxXXXXXX    LXXXXXXXXX    XXX*xxXXXX    XxXXXXXXXX
      XXZXUXXXBX    XXUXxxXX*X    XXXXXXXXXX    XXXXXXXxKX    ZXXXXXXXxx
501   xxxxxxxXXXZ   Z*X*XXXXxx    xXXPXXxxxx    xxxxXXLXXL    YXXXXXXXJX
      XxxXBXxBBZ    XXXXXEXXXX    XBXZXXXXXX    XBXXXXBXxx    xXXKxxxxxX
601   xxxxxxxxEX    LUZXUXBXLX    XXUXBXBXBX    XXXXXXYXBK    *KYOZXXXXX
      XXBXBEXXXx    UXBXXXXXXX    ZXXXXXXZxx    XXXXXYXBXZ    XxxxxxxxOx
701   XLXxxxxxxx    xxXUXXXXBB    LEKLEBBPXX    --
```

UNITED STATES PATENT AND TRADEMARK OFFICE
CERTIFICATE OF CORRECTION

PATENT NO. : 5,596,071
DATED : January 21, 1997
INVENTOR(S) : Jewel M. Payne, et al.

It is certified that error appears in the above-indentified patent and that said Letters Patent is hereby corrected as shown below:

Column 10, line 17: "*Agdc. Biol.*" should read --*Agric. Biol.*--

Column 11, line 36: "the exospotium," should read --the exosporium,--

Column 12, Table 5, line 22: "Ala, Vab, Leu--" should read --Ala, Val, Leu,--;

line 62: "toms," should read --toxins,--.

Column 13, line 52: "chemfluminescers" should read --chemiluminescers--

Column 14, line 53: "(C or T)TFT" should read --(C or T)TTT--;

line 59: "GCAATTFFAA" should read --GCAATTTTAA--.

Column 16, line 2: "Sporobolornyces" should read --Sporobolomyces--;

"Aureobasidiurn" should read --Aureobasidium--;

line 4: "Pseudornonas" should read --Pseudomonas--.

Column 18, Example 1 Table: "$K_2WO_4$" should read --$K_2HPO_4$--

Column 19, line 13: "Bedford, Me.)" should read --Bedford, MA);

line 31: "Louis, Mass.)" should read --Louis, MO).--

UNITED STATES PATENT AND TRADEMARK OFFICE
CERTIFICATE OF CORRECTION

PATENT NO. : 5,596,071
DATED : January 21, 1997
INVENTOR(S) : Jewel M. Payne, et al.

It is certified that error appears in the above-indentified patent and that said Letters Patent is hereby corrected as shown below:

Column 19, line 32: "C. Fischer," should read --S.G. Fischer,--;

line 41: "Saavedra," should read --R.A. Saavedra,--.

Column 20, lines 18&19: "(GCAATTTTAAATGAATTATATCC) (SEQ ID NO. should read --(GCAATTTTAAATGAATTATATCC)(SEQ. ID NO. 23).--

Column 20, line 49: "Sa/I-digested" should read --*SalI*-digested--

Column 21, line 67: "200/dg/ml" should read --200 µg/ml--

Column 22, line 10: "KW25 1 cells" should read --KW251 cells--;

line 17: "KW25 1 cells" should read --KW251 cells--.

lines 58&59: "for I hour" should read --for 1 hour--

Column 23, lines 21&22: "5' GCAFF ACAFF TTA AAT GAA GTA/T TAT 3' (SEQ ID NO. 26) should read --5'GCA/T ACA/T TTA AAT GAA GTA/T TAT 3' (SEQ ID NO. 26)

UNITED STATES PATENT AND TRADEMARK OFFICE
CERTIFICATE OF CORRECTION

PATENT NO. : 5,596,071
DATED : January 21, 1997
INVENTOR(S) : Jewel M. Payne, et al.

It is certified that error appears in the above-indentified patent and that said Letters Patent is hereby corrected as shown below:

Column 23, lines 23&24: "5'AAT GAA GTA/T TAT CCAfF GTA/T AAT 3'(SEQ ID NO. 27)" should read --5'AAT GAA GTA/T TAT CCA/T GTA/T AAT 3' (SEQ ID NO. 27)--

Column 23, lines 30&31: "5' GCAAGCGGCCGCTFATGGAATAAATTCAATT C/T T/G A/G TC T/A A 3'(SEQ ID NO. 28)." should read --5' GCAAGCGGCCGC-TTATGGAATAAATTCAATT C/T T/G A/G TC T/A A 3'(SEQ ID NO. 28).--

Column 23, line 39: "*B. thudngiensis*" should read --*B. thuringiensis*--

Column 24, lines 7&8: "5'-AGACFGGATCCATGGC(A or T)AC (A or T)AT (A or T)AAT GAA TTATA (T or C)CC-3' (SEQ ID NO. 29)." should read --5'-AGACTGGATCCATGGC(A or T)AC (A or T)AT(A or T)AATGAATTATA (T or C)CC-3' (SEQ ID NO. 29).--

Column 24, lines 18&19: "5'-TGGAATAAATFCAATT(C or T)(T or G)(A or G)TC (T or A)A-3'(SEQ ID NO. 33)." should read --5'-TGGAATAAATTCAATT(C or T)(T or G)(A or G)TC(T or A)A-3'(SEQ ID NO. 33).--

Column 24, line 40: "(PROMECA)." should read --(PROMEGA).--;
line 41: "KW25 1 cells (PROMECA)" should read KW251 cells (PROMEGA).--.

UNITED STATES PATENT AND TRADEMARK OFFICE
CERTIFICATE OF CORRECTION

PATENT NO. : 5,596,071

DATED : January 21, 1997

INVENTOR(S) : Jewel M. Payne, et al.

It is certified that error appears in the above-indentified patent and that said Letters Patent is hereby corrected as shown below:

Column 25, line 8: "Isolate PS8Q603" should read --Isolate PS86Q3--;

lines 11&12: "600 rim." should read --600 nm.--;

line 21:"200 $\mu$dg/ml was" should read --200 $\mu$g/ml was--

Column 25, lines 33-35: "5'GACTGCGGCCGCGTCGAC TrA ACG TGT AT(A or T)CG (C or G)TT T TAA TTT (T or A)GA(C or T)TC-3'" should read -- 5'GACTGCGGCCGCGTCGACTTAACG TGTAT(A or T)CG( C or G)TTT TAA TTT (T or A)GA( C or T)TC-3'.--

Column 26, line 10: "KW25 1 cells." should read --KW251 cells.--;

line 19: "KW25 1 cells." should read --KW251 cells.--;

line 37: "gene thin is" should read --gene that is--;

line 47: "*thudngiensis* Strain" should read --*thuringiensis* Strain--;

lines 50&51"thudngiensis" should read --*thuringiensis*--.

Column 27, line 10: "KW25 1" should read --KW251--;

line 44: "fi-exotoxin" should read --β-exotoxin--.

Column 28, line 57: "forward pruners." should read --forward primers--

UNITED STATES PATENT AND TRADEMARK OFFICE
CERTIFICATE OF CORRECTION

PATENT NO. : 5,596,071
DATED : January 21, 1997
INVENTOR(S) : Jewel M. Payne, et al.

It is certified that error appears in the above-indentified patent and that said Letters Patent is hereby corrected as shown below:

Column 28, line 67 & Col. 29, lines 1-2: "(TFTAGATCGT(A or C)TTGA (G or A)TTT(A or G)T(A or T)CC (SEQ ID NO. 35)." should read --(TTTAGAT-CGT(A or C)TTGA(G or A)TTT(A or G)T(A or T)CC (SEQ ID NO 35).--

Column 30, line 14: "a inker or" should read --a linker or--

Column 32, line 1: "in the an" should read --in the art--

Signed and Sealed this

Fourth Day of November, 1997

Attest:

BRUCE LEHMAN

*Attesting Officer*      *Commissioner of Patents and Trademarks*